(12) United States Patent
Tarleton

(10) Patent No.: US 7,892,555 B2
(45) Date of Patent: Feb. 22, 2011

(54) PROPHYLACTIC AND THERAPEUTIC IMMUNIZATION AGAINST PROTOZOAN INFECTION AND DISEASE

(75) Inventor: Rick L. Tarleton, Watkinsville, GA (US)

(73) Assignee: University of Georgia Research Foundation, Inc., Athens, GA (US)

(*) Notice: Subject to any disclaimer, the term of this patent is extended or adjusted under 35 U.S.C. 154(b) by 0 days.

(21) Appl. No.: 12/830,063

(22) Filed: Jul. 2, 2010

(65) Prior Publication Data

US 2010/0297173 A1 Nov. 25, 2010

Related U.S. Application Data

(60) Continuation of application No. 11/893,951, filed on Aug. 17, 2007, now abandoned, which is a division of application No. 11/015,578, filed on Dec. 17, 2004, now Pat. No. 7,309,784, which is a division of application No. 09/518,156, filed on Mar. 2, 2000, now Pat. No. 6,875,584.

(60) Provisional application No. 60/122,532, filed on Mar. 2, 1999.

(51) Int. Cl.
  *A61K 39/00* (2006.01)
  *A61K 39/002* (2006.01)
  *C07K 14/00* (2006.01)

(52) U.S. Cl. .............. 424/184.1; 424/265.1; 424/269.1; 530/350

(58) Field of Classification Search ........................ None
See application file for complete search history.

(56) References Cited

U.S. PATENT DOCUMENTS

| | | |
|---|---|---|
| 5,304,371 A | 4/1994 | Reed |
| 5,646,114 A | 7/1997 | Lambert et al. |
| 6,419,933 B1 | 7/2002 | Reed et al. |
| 6,875,584 B1 | 4/2005 | Tarleton et al. |
| 7,309,784 B2 | 12/2007 | Tarleton et al. |
| 2004/0241729 A1 | 12/2004 | Liew |
| 2005/0158347 A1 | 7/2005 | Tarleton et al. |
| 2005/0244505 A1 | 11/2005 | Higbee et al. |
| 2006/0228300 A1 | 10/2006 | Chang et al. |
| 2007/0178100 A1 | 8/2007 | Tarleton et al. |

FOREIGN PATENT DOCUMENTS

| | | |
|---|---|---|
| WO | WO 2005/111622 A2 | 11/2005 |
| WO | WO 2005/111622 A3 | 10/2006 |

OTHER PUBLICATIONS

Armah et al., "S-Myristoylation of a Glycosylphosphatidylinositol-specific Phospholipase C in *Trypanosoma brucei*," *J. Biol. Chem.*, 274(9):5931-5938 (Feb. 26, 1999).
Abrahamsohn, "Cytokines in innate and acquired immunity to *Trypanosoma cruzi* infection," *Braz. J Med. Biol. Res.*, 31(1):117-121 (Jan. 1998).
Alberti et al., "Specific cellular and humoral immune response in Balb/c mice immunised with an expression genomic library of *Trypanosoma cruzi*," *Vaccine*, 16(6):608-612 (Apr. 1998).
Al-Qahtani et al., "A 5' untranslated region which directs accurate and robust translation by prokaryotic and mammalian ribosomes," *Nuc. Acids Res.*, 24(6):1173-1174 (1996).
Andrews et al., "Presence of antibodies to the major surface glycoprotein of *Trypanosoma cruzi* amastigotes in sera from chagasic patients," *Am. J. Trop. Med. Hyg.*, 40(1):46-49 (1989).
Andrews, "The Acid-Active Hemolysin of *Trypanosoma cruzi*," *Exp. Parasitol.*, 71:241-244 (1990).
Barry et al., "Protection against mycoplasma infection using expression-library immunization," *Nature*, 377(6550):632-635 (1995).
Barry et al., "Biological features of genetic immunization," *Vaccine*, 15(8):788-791 (1997).
Basombrio, "*Trypanosoma cruzi*: Partial Prevention of the Natural Infection of Guinea Pigs with a Killed Parasite Vaccine," *Exp. Parasitol.*, 71:1-8 (1990).
Bharadwaj et al., "Induction of Protective Immune Responses by Immunization with Linear Multiepitope Peptides Based on Conserved Sequences from *Plasmodium falciparum* Antigens," *Infect. Immun.*, 66(7):3232-3241 (Jul. 1998).
Biebinger et al., "A Plasmid Shuttle Vector Bearing an rRNA Promoter is Extrachromosomally Maintained in *Crithidia fasciculata*," *Exp. Parasitol.*, 83(2):252-258 (1996).
Bliss et al., "IL-12, as an Adjuvant, Promotes a T Helper 1 Cell, but Does Not Suppress a T Helper 2 Cell Recall Response," *J. Immunol.*, 156:(3):887-894 (1996).
Brener, "Why Vaccines do not work in Chagas Disease," *Parasitol. Today*, 2(7):196-197 (1986).
Carpenter et al., "Linearized free maxicircle DNA in *Crithidia fasciculata* is a product of topoisomerase II-mediated cleavage," *Mol. Biochem. Parasitol.*, 76:115-123 (1996).
Chow et al., "Development of Th1 and Th2 Populations and the Nature of Immune Responses to Hepatitis B Virus DNA Vaccines Can Be Modulated by Codelivery of Various Cytokine Genes," *J. Immunol.*, 160(3):1320-1329 (Feb. 1, 1998).
Clayton et al., "Protein Trafficking in Kinetoplastid Protozoa," *Microbiol. Rev.*, 59(3):325-344 (1995).

(Continued)

*Primary Examiner*—Mark Navarro
(74) *Attorney, Agent, or Firm*—Mueting Raasch & Gebhardt, P.A.

(57) ABSTRACT

Polypeptide and polynucleotide vaccines effective to treat or prevent infection of a mammal, such as a dog, a cat, or a human, by a protozoan. Methods of treatment and prevention are also provided, including therapeutic administration of the vaccine to an infected mammal to prevent progression of infection to a chronic debilitating disease state. Preferred embodiments of the polynucleotide vaccine contain nucleotide coding regions that encode polypeptides that are surface-associated or secreted by *T. cruzi*. Optionally the efficacy of the polynucleotide vaccine is increased by inclusion of a nucleotide coding region encoding a cytokine. Preferred embodiments of the polypeptide vaccine include immunogenic peptides that contain membrane transducing sequences that allow the polypeptides to translocate across a mammalian cell membrane.

13 Claims, 21 Drawing Sheets

OTHER PUBLICATIONS

Coburn et al., "Stable DNA transfection of a wide range of trypanosomatids," Mol. Biochem. Parasitol., 46:169-179 (1991).

Corny et al., "Polynucleotide-Mediated Immunization Therapy of Cancer," Seminars Oncol., 23(1):135-147 (1996).

Costa et al., "Immunization with a plasmid DNA containing the gene of trans-sialidase reduces Trypanosoma cruzi infection in mice," Vaccine, 16(8):768-774 (May 1998).

Cross et al., "The Surface Trans-Sialidase Family of Trypanosoma cruzi," Ann. Rev. Microbiol., 47:385-411 (1993).

Denkers et al., "Regulation and Function of T-Cell-Mediated Immunity during Toxoplasma gondii Infection," Clin Microbiol Rev. 1998, vol. 11, pp. 569-588.

DeRisi et al., "Use of a cDNA microarray to analyse gene expression patterns in human cancer," Nature Genet., 14(4):457-460 (1996).

DeRisi et al., "Exploring the Metabolic and Genetic Control of Gene Expression on a Genomic Scale," Science, 278(5338):680-686 (1997).

Donnelly et al., "DNA Vaccines," Ann. Rev. Immunol., 15:617-648 (1997).

Ellis et al., "New Technologies for Making Vaccines," Chapter 29, p. 571 second paragraph of book entitled Vaccines, Authors: S.A. Plotkin and E.A. Mortimer (with 40 contributors), Published by W.B. Saunders Company (Philadelphia), 1988.

Endresz et al., "Induction of human cytomegalovirus (HCMV)-glycoprotein B (gB)-specific neutralizing antibody and phosphoprotein 65 (pp65)-specific cytotoxic T lymphocyte responses by naked DNA immunization," Vaccine, 17(1):50-58 (Jan. 1999).

Englund, "The structure and biosynthesis of glycosyl phosphatidylinositol protein anchors," Annu. Rev. Biochem., 62:121-138 (1993).

Freedman et al., "Two more independent selectable markers for stable transfection of Leishmania," Mol. Biochem. Parasitol., 62:37-44 (1993).

Fontt et al., "Relationship between granulocyte macrophage-colony stimulating factor, tumour necrosis factor-α and Trypanosoma cruzi infection of murine macrophages," Parasite Immunol., 17(3):135-141 (1995).

Fontt et al., "Granulocyte-Macrophage Colony-Stimulating Factor: Involvement in Control of Trypanosoma cruzi Infection in Mice," Infect. Immun., 64(8):3429-3434 (1996).

Fontt et al., "Effects of Granulocyte-Macrophage Colony-Stimulating Factor and Tumor Necrosis Factor Alpha on Trypanosoma cruzi Trypomastigotes," Infect. Immun., 66(6):2722-2727 (Jun. 1998).

Fouts et al., "Nucleotide sequence and transcription of a trypomastigote surface antigen gene of Trypanosoma cruzi," Mol. Biochem. Parasitol., 46:189-200 (1991).

Fouts et al., "Trypanosoma cruzi trypomastigote surface glycoprotein (TSA-1) mRNA, GenBank Accession No. M58466," (1993).

Garg et al., "Proteins with Glycosylphosphatidylinositol (GPI) Signal Sequences Have Divergent Fates during a GPI Deficiency," J. Biol. Chem., 272(19):12482-12491 (1997).

Garg et al., "Delivery by Trypanosoma cruzi of Proteins into the MHC Class I Antigen Processing and Presentation Pathway," J. Immunol., 158:3293-3302 (1997).

Garg et al., "Elicitation of protective immunity to Trypanosoma cruzi using DNA vaccines," Proceedings of the 10th International Congress of Immunology, New Delhi, India, Monduzzi, Bologna pp. 1421-1426 (Nov. 1-6, 1998).

Geissler et al., "Enhancement of Cellular and Humoral Immune Responses to Hepatitis C Virus Core Protein Using DNA-Based Vaccines Augmented with Cytokine-Expressing Plasmids," J. Immunol., 158(3):1231-1237 (1997).

Gomes, "PCR and Sero-Diagnosis of Chronic Chagas' Disease," Appl. Biochem. Biotechnol., 66(2):107-119 (1997).

Gurunathan et al., "Vaccination with DNA Encoding the Immunodominant LACK Parasite Antigen Confers Protective Immunity to Mice Infected with Leishmania major," J. Exp. Med., 186(7):1137-1147 (1997).

Ha et al., "Use of the green fluorescent protein as a marker in transfected Leishmania," Mol. Biochem. Parasitol., 77:57-64 (1996).

Hartikka et al., "An Improved Plasmid DNA Expression Vector for Direct Injection into Skeletal Muscle," Human Gene Ther., 7(10):1205-1217 (1996).

Higuchi et al., "The Role of Active Myocarditis in the Development of Heart Failure in Chronic Chagas' Disease: A Study Based on Endomyocardial Biopsies," Clin. Cardiol. 10(11):665-670 (1987).

Hoffman et al., "Toward clinical trials of DNA vaccines against malaria," Immunol. Cell Biol., 75(4):376-381 (1997).

Hsu et al., "Immunoprophylaxis of allergen-induced immunoglobulin E synthesis and airway hyperresponsiveness in vivo by genetic immunization," Nat. Med., 2(5):540-544 (1996).

Hudson et al., "Immune response to South American trypanosomiasis and its relationship to Chagas' disease," Brit. Med. Bull., 41(2):175-180 (1985).

Iida et al., "Amastigotes of Trypanosoma cruzi escape destruction by the terminal complement components," J. Exp. Med., 169:881-891 (1989).

Inverso et al., "Crithidia fasciculata contains a transcribed leishmanial surface proteinase (gp63) gene homologue," Mol. Biochem. Parasitol., 57:47-54 (1993).

Irvine et al., "Cytokine Enhancement of DNA Immunization Leads to Effective Treatment of Established Pulmonary Metastases," J. Immunol., 156(1):238-245 (1996).

Jones et al., "Amplification of a Trypanosoma cruzi DNA sequence from inflammatory lesions in human chagasic cardiomyopathy," Am. J. Trop. Med. Hyg., 48(3):348-357 (1993).

Jones et al., "Synthetic oligodeoxynucleotides containing CpG motifs enhance immunogenicity of a peptide malaria vaccine in Aotus monkeys," Vaccine, 17(2324):3065-3071 (Aug. 6, 1999).

Kelly et al., "A shuttle vector which facilitates the expression of transfected genes in Trypanosoma cruzi and Leishmania," Nuc. Acids Res., 20(15):3963-3969 (1992).

Kelly, "Trypanosomatid Shuttle Vectors: New Tools for the Functional Dissection of Parasite Genomes," Parasitol. Today, 11(12):447-450 (1995).

Kidder et al., "The Growth and Nutrition of Crithida fasciculata," J. Gen. Microbiol., 18:621-638 (1958).

Kierszenbaum and Hudson, "Autoimmunity in Chagas Disease: Cause or Symptom?" Parasitol. Today, 1(1):4-9 (1985).

Kierszenbaum, "Autoimmunity in Chagas' disease," J. Parasitol., 72(2):201-211 (1986).

Kim et al., "In Vivo Engineering of a Cellular Immune Response by Coadministration of IL-12 Expression Vector with a DNA Immunogen," J. Immunol., 158(2):816-826 (1997).

Kim et al., "Cytokine Molecular Adjuvants Modulate Immune Responses Induced by DNA Vaccine Constructs for HIV-1 and SIV," J. Interferon Cytokine Res., 19(1):77-84 (Jan. 1999).

Kozak, "Features in the 5' Non-coding Sequences of Rabbit α and β-Globin mRNAs that Affect Translational Efficiency," J. Mol. Biol., 235:95-110 (1994).

Krettli et al., "Resistance against Trypanosoma cruzi associated to anti-living trypomastigote antibodies," J. Immunol., 128(5):2009-2012 (1982).

La Flamme et al., "Expression of mammalian cytokines by Trypanosoma cruzi indicates unique signal sequence requirements and processing," Mol. Biochem. Parasitol., 75:25-31 (1995).

Lane et al., "Detection of Trypanosoma cruzi with the polymerase chain reaction and in situ hybridization in infected murine cardiac tissue," Am. J. Trop. Med. Hyg., 56(6):588-595 (1997).

Le Borgne et al., "In Vivo Induction of Specific Cytotoxic T Lymphocytes in Mice and Rhesus Macaques Immunized with DNA Vector Encoding an HIV Epitope Fused with Hepatitis B Surface Antigen," Virology, 240(2):304-315 (Jan. 20, 1998).

LeBowitz et al., "Development of a stable Leishmania expression vector and application to the study of parasite surface antigen genes," Proc. Natl. Acad. Sci. USA, 87:9736-9740 (1990).

LeBowitz et al., "Simultaneous transient expression assays of the trypanosomatid parasite Leishmania using β-galactosidase and β-glucuronidase as reporter enzymes," Gene, 103:119-123 (1991).

Ley et al., "The exit of *Trypanosoma cruzi* from the phagosome is inhibited by raising the pH of acidic compartments," *J. Exp. Med.*, 171:401-413 (1990).

Low et al., "*Trypanosoma cruzi* amastigote surface protein-2 (ASP-2) mRNA, GenBank Accession No. U77951," submitted to Gen Bank on Nov. 11, 1996.

Low et al., "Molecular cloning of the gene encoding the 83 kDa amstigote surface protein and its identification as a member of the *Trypanosoma cruzi* sialidase superfamily," *Mol. Biochem. Parasitol.*, 88(1-2):137-149 (1997).

Low et al.,"Amastigote Surface Proteins of *Trypanosoma cruzi* Are Targets for CD8+CTL," *J. Immunol.*, 160:1817-1823 (Feb. 15, 1998).

Low et al., "Identification of the 83-kDa Amastigote Surface Protein of *Trypanosoma cruzi* as a Member of the Sialidase Family and a Target of CTL Responses," Abstract and Poster, *Joint Meeting of the Amer. Soc. Tropical Med Hyg., Amer. Soc. Parasitologists*, Baltimore, MD 6 pages (1996).

Lowrie et al., "Protection against tuberculosis by a plasmid DNA vaccine," *Vaccine*, 15(8):834-838 (1997).

McCluskie et al., "Route and Method of Delivery of DNA Vaccine Influence Immune Responses in Mice and Non-Human Primates," *Mol. Med.*, 5(5):287-300 (May 1999).

Mensa-Wilmot et al., "A Glycosylphosphatidylinositol (GPI)-Negative Phenotype Produced In *Leishmania major* by GPI Phospholipase C from *Trypanosoma brucei*: Topography of Two GPI Pathways," *J. Cell Biol.*, 124(6):935-947 (1994).

Mensa-Wilmot et al., "Purification and Use of Recombinant Glycosylphosphatidylinositol-Phospholipase C," *Methods Enzymol.*, 250:641-655 (1995).

Meyer zum Büschenfelde et al., "*Trypanosoma cruzi* induces strong IL-12 and IL-18 gene expression in vivo: correlation with interferon-gamma (IFN-γ) production," *Clin. Exp. Immunol.*, 110(3):378-385 (1997).

Monaco, "A molecular model of MHC class-I-restricted antigen processing," *Immunol. Today*, 13(5):173-179 (1992).

Muller et al., "*Trypanosoma cruzi*: Isolate Dependence in the Induction of Lytic Antibodies in the Mouse and Rabbit," *Exp. Parasitol.*, 61:284-293 (1986).

Nabors et al., "Differential control of IFN-γ and IL-2 production during *Trypanosoma cruzi* infection," *J. Immunol.*, 146(10):3591-3598 (1991).

Nagahara et al., "Transduction of full-length TAT fusion proteins into mammalian cells: TAT-p27$^{kip1}$ induces cell migration," *Nature Med.*, 4(12):1449-1452 (Dec. 1998).

Office Action dated Feb. 2, 2010, issued in U.S. Appl. No. 11/893,951.

Pan et al., "Amastigote and Epimastigote Stage-Specific Components of *Trypanosoma cruzi* Characterized by Using Monoclonal Antibodies: Purification and Molecular Characterization of an 83-kilodalton Amastigote Protein," *J. Immunol.*, 143(3):1001-1008 (1989).

Peterson et al., "Cloning of a major surface-antigen gene of *Trypanosoma cruzi* and identification of a nonapeptide repeat," *Nature*, 322:(6079):566-568 (1986).

Rashid et al., "Roles of Gln81 and Cys80 in catalysis by glycosylphosphatidylinositol-phospholipase C from *Trypanosoma brucei*," *Eur. J. Biochem.*, 264:914-920 (Sep. 1999).

Raz et al., "Preferential induction of a Th$_1$ immune response and inhibition of specific IgE antibody formation by plasmid DNA immunization," *Proc. Nat'l. Acad. Sci. USA.*, 93(10):5141-5145 (1996).

Reed, "In vivo administration of recombinant IFN-γ induces macrophage activation, and prevents acute disease, immune suppression, and death in experimental *Trypanosoma cruzi* infections," *J. Immunol.*, 140(12):4342-4347 (1988).

Reis et al., "An in Situ Quantitative Immunohistochemical Study of Cytokines and IL-2R+ in Chronic Human Chagasic Myocarditis: Correlation with the Presence of Myocardial *Trypanosoma cruzi* Antigens," *Clin. Immunol. Immunopathol.*, 83(2):165-172 (1997).

Rodriguez et al., "*Trypanosoma cruzi* Infection in B-Cell-Deficient Rats," *Infect. Immun.*, 31(2):524-529 (1981).

Rötzschke et al., "Exact prediction of a natural T cell epitope," *Eur. J. Immunol.*, 21(10):2891-2894 (1991).

Ruiz et al., "Monoclonal antibodies against the flagellar fraction of epimastigotes of Trypanosoma cruzi: immunoprotection against metacyclic trypomastigotes obtained by immunization of mice with an affmity-purified antigen," *Mol. Biochem. Parasitol.* 39:117-125 (1990).

Santos-Buch et al., "Chapter 8: Pathology of Chagas' Disease," in *Immunology and Pathogenesis of Trypanosonziasis*, Tizard, ed., CRC Press, Boca Raton, Title page, publication page and pp. 145-183 (1985).

Santos et al., "*Trypanosoma cruzi* surface protein-1 mRNA, GenBank Accession No. U74494," submitted to GenBank on Oct. 15, 1996.

Santos et al., "The Identification and Molecular Characterization of a *Trypanosoma cruzi* Amastigote Surface Protein, Asp-1, a Member of the Trans-Sialidase Gene Superfamily," Abstract and Poster, Joint Meeting of the Amer. Soc. Biochemistry and Molecular Biology, Amer. Soc. Investigative Pathology, and Amer. Assoc. Immunologists, Jun. 1-6, New Orleans, LA, *FASEB J.*, 10(6):A1083 9 pages (1996).

Santos et al., "The identification and molecular characterization of *Trypanosoma cruzi* amastigote surface protein-1, a member of the *trans*-sialidase gene super-family," *Mol. Biochem. Parasitol.*, 86:1-11 (1997).

Schenkman et al., "Mucin-like glycoproteins linked to the membrane by glycosylphosphatidylinositol anchor are the major acceptors of sialic acid in a reaction catalyzed by trans-sialidase in metacyclic forms of *Trypanosoma cruzi*," *Mol. Biochem. Parasitol.*, 59:293-303 (1993).

Schirmbeck et al., "DNA Vaccine Primes MHC Class I-Restricted, Simian Virus 40 Large Tumor Antigen-Specific CTL in H-2$^d$ Mice That Reject Syngeneic Tumors," *J. Immunol.*, 157(8):3550-3558 (1996).

Schofield, "Control of Chagas' disease vectors," *Brit. Med. Bull.*, 41(2):187-194 (1985).

Schutze-Redelmeier et al., "Introduction of Exogenous Antigens into the MHC Class 1 Processing and Presentation Pathway by *Drosophila* Antennapedia Homeodomain Primes Cytotoxic T Cells In Vivo," *J. Immunol.*, 157:650-655 (1996).

Schwarze et al., "In Vivo Protein Transduction: Delivery of a Biologically Active Protein into the Mouse," *Science*, 285(5433):1569-1572 (Sep. 3, 1999).

Scott et al., "$^{75}$Se-methionine labelled *Trypanosoma cruzi* blood trypomasitgotes: opsonization by chronic infection serum facilitates killing in spleen and liver," *Clin. Exp. Immunol.*, 48:754-757 (1982).

Sedegah et al., "Protection against malaria by immunization with plasmid DNA encoding circumsporozoite protein," *Proc. Nat'l Acad. Sci. USA*, 91(21):9866-9870 (1994).

Seifert et al., "Shuttle mutagenesis: A method of transposon mutagenesis for *Saccharomyces cerevisiae*," *Proc. Natl. Acad. Sci. USA*, 83:735-739 (1986).

Sheibani, "Prokaryotic gene fusion expression systems and their use in structural and functional studies of proteins," *Prep. Biochem. Biotechnol.*, 29(1):77-90 (Feb. 1999).

Shi et al., "Immunogenicity and in vitro protective efficacy of a recombinant multistage *Plasmodium falciparum* candidate vaccine," *Proc. Natl. Acad. Sci USA*, 96(4):1615-1620 (Feb. 16, 1999).

Silva et al., "Tumor Necrosis Factor Alpha Mediates Resistance to *Trypanosoma cruzi* Infection in Mice by Inducing Nitric Oxide Production in Infected Gamma Interferon-Activated Macrophages," *Infect. Immun.*, 63(12):4862-4867 (1995).

Silva et al., "The role of IL-12 in experimental *Trypanosoma cruzi* infection," *Braz. J. Med. Biol. Res.*, 31(1):111-115 (Jan. 1998).

Sin et al., "Enhancement of protective humoral (Th2) and cell-mediated (Th1) immune responses against herpes simplex virus-2 through co-delivery of granulocyte-macrophage colony-stimulating factor expression cassettes," *Eur. J. Immunol.*, 28(11):3530-3540 (Nov. 1998).

Swinkels et al., "A phosphoglycerate kinase-related gene conserved between *Trypanosoma brucei* and *Crithidia fasciculata*," *Mol. Biochem Parasitol*, 50:69-78 (1992).

Tackett et al., "Phase 1 safety and immune response studies of a DNA vaccine encoding hepatitis B surface antigen delivered by a gene delivery device," *Vaccine*, 17(22):2826-2829 (Jul. 16, 1999).

Tarleton, "Depletion of CD8+ T cells increases susceptibility and reverses vaccine-induced immunity in mice infected with *Trypanosoma cruzi*," *J. Immunol.*, 144(2):717-724 (1990).

Tarleton et al., ""Autoimmune rejection" of neonatal heart transplants in experimental Chagas disease is a parasite-specific response to infected host tissue," *Proc. Natl. Acad. Sci. USA*, 94(8):3932-3937 (1997).

Tarleton et al., "Chagas Disease Etiology: Autoimmunity or Parasite Persistence?" *Parasitol. Today*, 15(3):94-99 (Mar. 1999).

Tarleton et al., "Vaccine Discovery and Testing in a Murine Model of American Trypanosomiasis," Abstract C10 *Mem. Inst. Oswaldo Cruz, Rio de Janeiro*, 94 (Suppl. II):17 (Nov. 1999).

Teilhet et al., "Effect of short 5' *UTR*s on protein synthesis in two biological kingdoms," *Gene*, 222(1):91-97 (Nov. 5, 1998).

Tobin et al., "Transfected *Leishmania* Expressing Biologically Active IFN-γ," *J. Immunol.*, 150(11):5059-5069 (1993).

Torri et al., "A β-Like DNA Polymerase from the Mitochondrion of the Trypanosomatid *Crithidia fasciculata*," *J. Biol. Chem.*, 269(11):8165-8171 (1994).

Trischmann, "Role of cellular immunity in protection against *Trypanosoma cruzi* in mice," *Parasite Immunol.*, 6(6):561-570 (1984).

Udenfriend et al., "How Glycosyl-Phosphatidylinositol-anchored membrane proteins are made," *Ann. Rev. Biochem.*, 64:563-591 (1995).

Ulmer et al., "Heterologous Protection Against Influenza by Injection of DNA Encoding a Viral Protein," *Science*, 259(5102):1745-1749 (1993).

Ullu et al., "Chapter 7: *Trans*-splicing in trypanosomatid protozoa," in *Molecular Biology of Parasitic Protozoa*, Smith et al., eds., IRL Press, NY, Title page, publication page, and pp. 115-133 (1996).

Vanhamme et al., "Control of Gene Expression in Trypanosomes," *Microbiol. Rev.*, 59(2):223-240 (1995).

Villalta et al., "Effects of human colony-stimulating factor on the uptake and destruction of a pathogenic parasite (*Trypanosoma cruzi*) by human neutrophils," *J. Immunol.*, 137(5):1703-1707 (1986).

Voth et al., "Differentially expressed *Leishmania major gp63* genes encode cell surface leishmanolysin with distinct signals for glycosylphosphatidylinositol attachment," *Mol. Biochem. Parasitol.*, 93(1):31-41 (May 15, 1998).

Waisman et al., "Suppressive vaccination with DNA encoding a variable region gene of the T-cell receptor prevents autoimmune encephalomyelitis and activates Th2 immunity," *Nature Med.*, 2(8):899-905 (1996).

Wallace, "Flagellate parasites of mosquitos with special reference to *Crithidia fasciculata* léger 1902," *J. Parasitol.*, 29:196-205 (1943).

Wang et al., "Simultaneous Induction of Multiple Antigen-Specific Cytotoxic T Lymphocytes in Nonhuman Primates by Immunization with a Mixture of Four *Plasmodium falciparum* DNA Plasmids," *Infect. Immun.*, 66(9):4193-4202 (Sep. 1998).

Wang et al., "Induction of Antigen-Specific Cytotoxic T Lymphocytes in Humans by a Malaria DNA Vaccine," *Science*, 282:476-480 (Oct. 16, 1998).

Wirtz et al., "Inducible Gene Expression in Trypanosomes Mediated by a Prokaryotic Repressor," *Science*, 268:1179-1183 (1995).

Wirtz et al., "Regulated processive transcription of chromatin by T7 RNA polymerase in *Trypanosoma brucei*," *Nuc.Acids Res.*, 26(20):4626-4634 (Oct. 15, 1998).

Wirtz et al., "A tightly regulated inducible expression system for conditional gene knock-outs and dominant-negative genetics in *Trypanosoma brucei*" *Mol. Biochem. Parasitol.*, 99(1):89-101 (Mar. 15, 1999).

Wizel et al., "Induction of murine cytotoxic T lymphocytes against *Plasmodium falciparum* sporozoite surface protein 2," *Eur. J. Immunol.*, 24(7):1487-1495 (1994).

Wizel et al., "Identification of *Trypanosoma cruzi Trans*-Sialidase Family Members as Targets of Protective CD8+ TC1 Responses," *J. Immunol.*, 159(12):6120-6130 (1997).

Wizel et al., "Human Infection with *Trypanosoma cruzi* Induces Parasite Antigen-Specific Cytotoxic T Lymphocyte Responses," *J. Clin. Invest.*, 102(5):1062-1071 (Sep. 1998).

Wizel et al., "Vaccination with Trypomastigote Surface Antigen 1-Encoding Plasmid DNA Confers Protection against Lethal *Trypanosoma cruzi* Infection," *Infect. Immun.*, 66(11):5073-5081 (Nov. 1998).

World Health Organization, "Special programme for research and training in tropical diseases, Sixth Programme Report, Chapter Six: Chagas' Disease," TDR/PR-6/83.6-CHA, UNDP/World Bank/WHO (1983).

World Health Organization, "Special programme for research and training in tropical diseases; Meeting on the development of trypanocidal compounds for the sterilization of blood," Geneva, Dec. 13-14, TDR/CHA/BS/84.3, UNDP/World Bank/WHO (1984).

Wrightsman et al., "Identification of Immunodependent Epitopes in *Trypanosoma cruzi* Trypomastigone Surface Antigen-1 Protein That Mask Protective Epitopes," *J. Immunol.*, 153(7):3148-3154 (1994).

Xiang et al., "Vaccination with a Plasmid Vector Carrying the Rabies Virus Glycoprotein Gene Induces Protective Immunity against Rabies Virus," *Virology*, 199(1):132-140 (1994).

Xiang et al., "Manipulation of the Immune Response to a Plasmid-Encoded Viral Antigen by Coinoculation with Plasmids Expressing Cytokines," *Immunity*, 2(2):129-135 (1995).

Yokoyama et al., "DNA Immunization Confers Protection against Lethal Lymphocytic Choriomeningitis Virus Infection," *J. Virol.*, 69(4):2684-2688 (1995).

Zhang et al., "The expression of biologically active human p53 in *Leishmania* cells: a novel eukaryotic system to produce recombinant proteins," *Nuc. Acids Res.*, 23(20):4073-4080 (1995).

Zhang et al., "Identification and overexpression of the A2 amastigote-specific protein in *Leishmania donovani*," *Mol. Biochem. Parasitol.*, 78:79-90 (1996).

Zhang et al., "Loss of virulence in *Leishmania donovani* deficient in an amastigote-specific protein, A2," *Proc. Natl. Acad. Sci. USA*, 94:8807-8811 (1997).

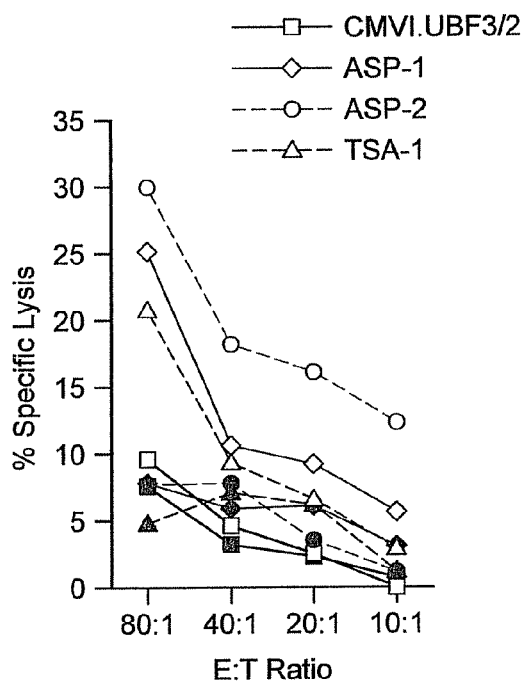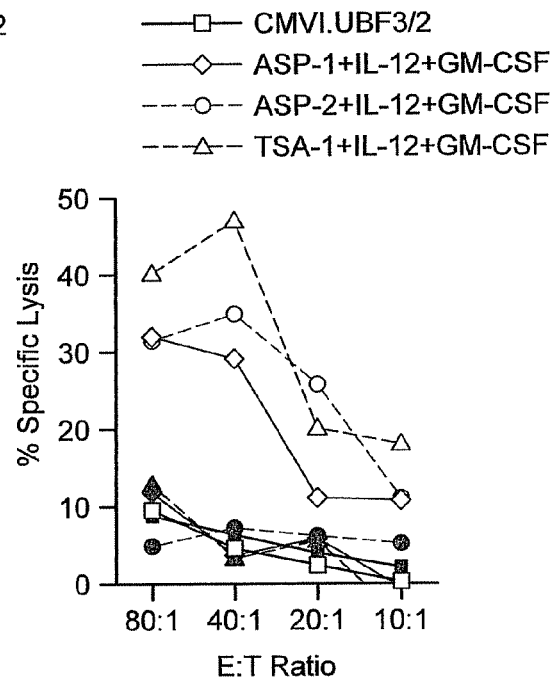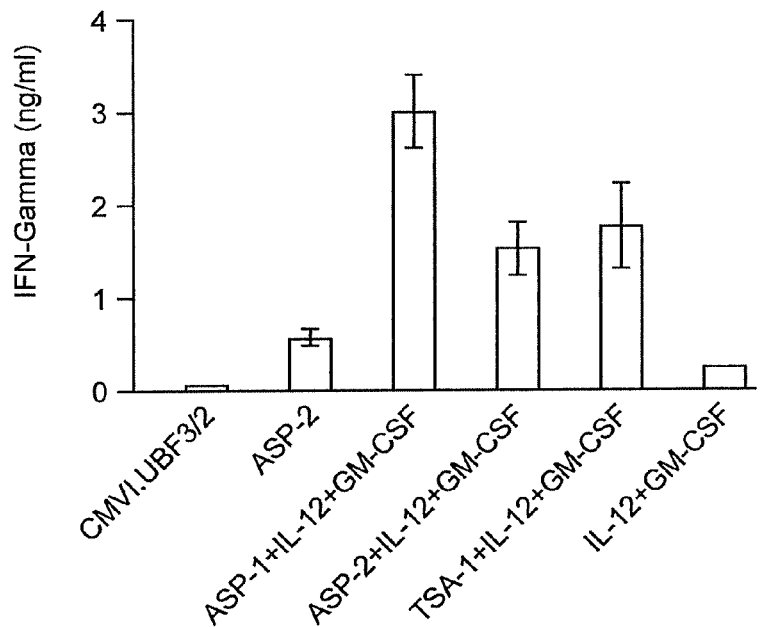

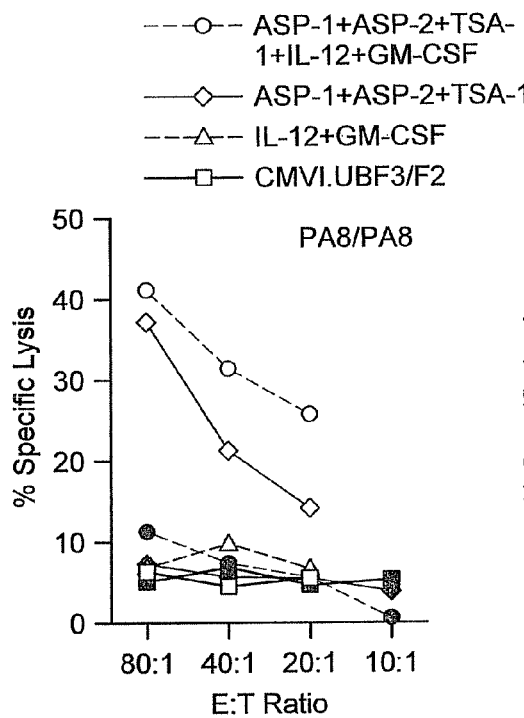
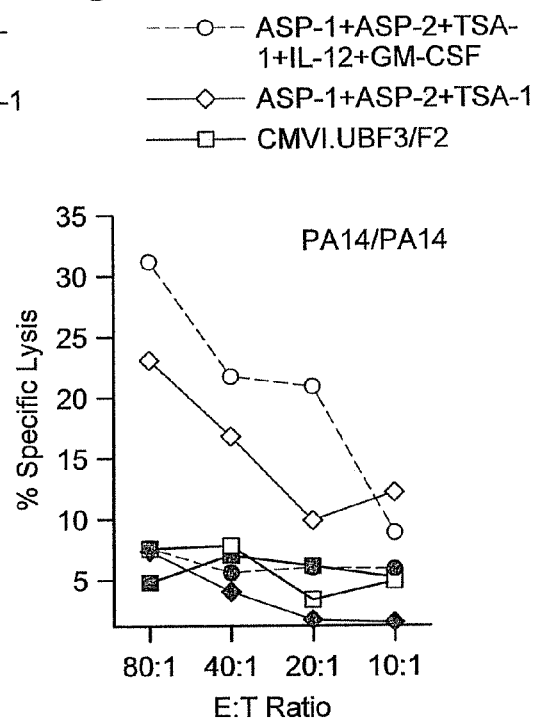
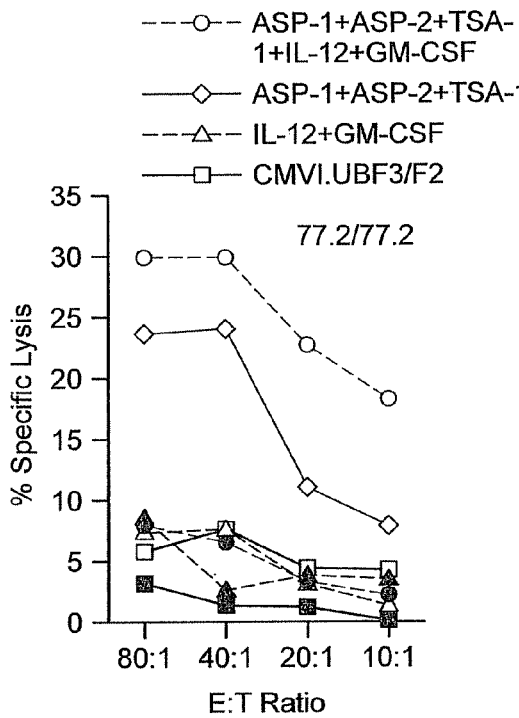
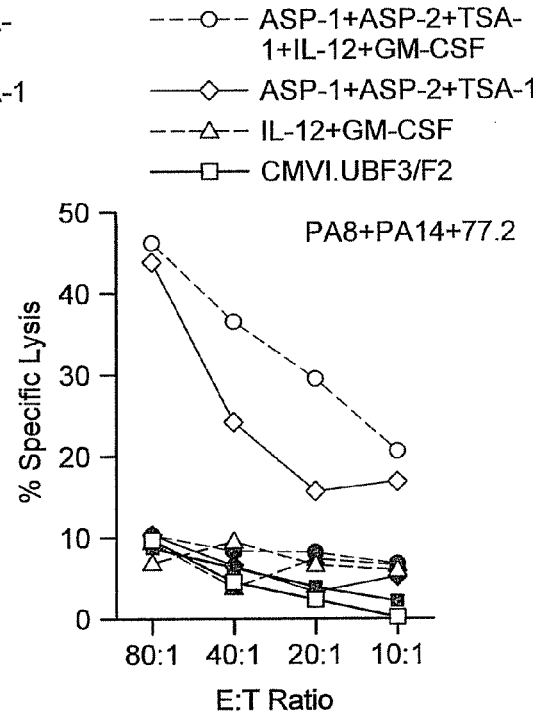

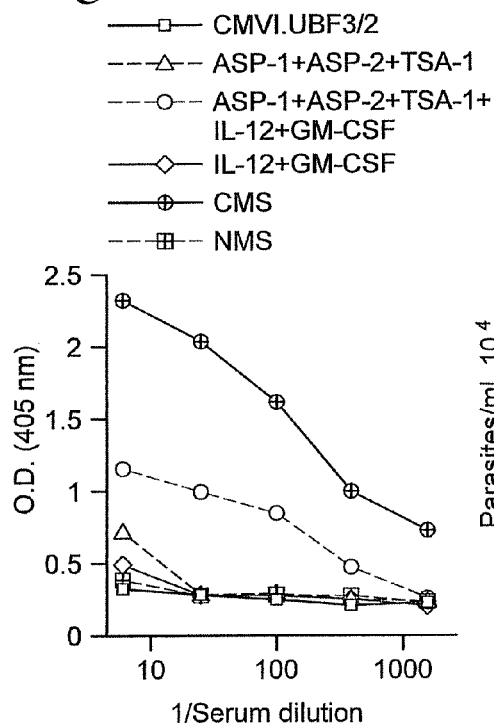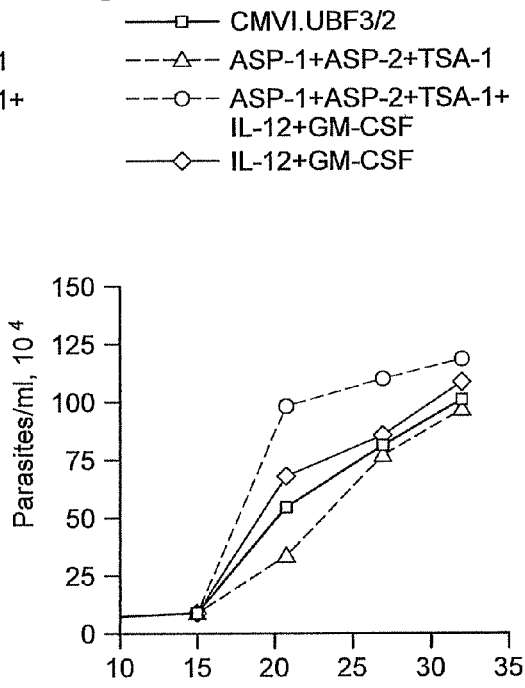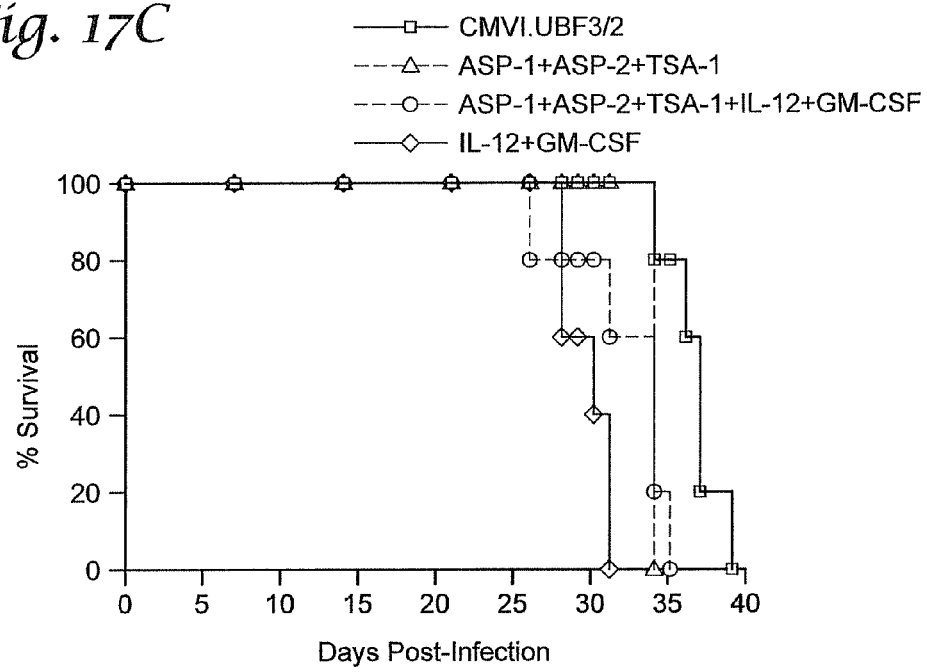

Fig. 19

The porin sequence

```
ATGCGGAAGAAAGCCGCAGCATTAGCAGCGCCCACAGCAGACACACGGCCGACGTGCCGCGGGGCTGCCATTGCCA
ATAAATTTATGGAACGTGCCGGCCCCCGTGAGGGCGTTGGGAGATCAACGGAGATGCCGGCTGCTGGACCGACGGG
GTCTCAAAGAACTCAAACGCAACGGGAGGTGAAAGCGTCACAAGACGCCGACGCGGCGGCCATTAGTAGTTATTTC
CAGTCCGAATTGGTGACATCTCAGTCGCACGAGGGTGTGTCTCCTCTGGCAAAGACTAGGGCCAACGAACGGCGGA
ACGGGGAGCAGGAGCGGGAGAAGGAACTGCCGGCGGTTGGTGGCGCCGTTCCAACTGGGAAGGGGACGGACCCCAA
ACAGCGAGTGCTGCAGGATTTGCCAGCGATGCACGCGGAGGGACAAAACCAGCACGGTAGAGAGGGTGACAAGGGT
GTTTCCGTGAAGATGGACTCCCCTGGTCGCGTACAGGTGCTGGAGCAAATGTTGCTACACCTGGCTGCATTGAACA
GACAGCTAGAATTAGAACTTATAGAAACGCGACGGGAACTGACGATGTACAAGCAGCTTTTACCTGATGTGCAGCG
CCAGACCGAGGCCCATGCTTTGTCTCAGGAGCATCACAAAGCGAATAGTGCTGCTCCGCCACTGATGTCAGATGAG
AGGCGACGACAGATGCTCTTTACAGGGCAACAACAACAACAGCAACAAGTGGAAGATCTGCATGGCGGTATTAGCG
GGTGGGAAACGGCAGCGAGGAGAATGCGCTATGGTTACGAGGAGGGGGAGAGGGACGCCCTTTCAGATGGTGAGGG
CCGTCCACGTTGCGCAGGTCGTATGGGCTCCCCGAAGAGATTCCTTTCAACACAACCGCCTCGAAGCAGCAGGAAC
CATCGGAACCCTCACGCTGCTAACGGGACAAATGGCAATAGTCATGTTCCCCATTCGTCCAGACAAAAAAGTCACC
CGACAAGAGGAGCTGCTGTAACTTCCGTACCGTTGGCGGCGTCCGCAACCAATCGCCGAGGTCGTTCCATGCGACA
ACATACCCGACCCCGCGGACCTTCTTATCTTTTCGAACGCCTCGACGCTGAGGATGCAATTGATATGCTGGAGACG
CTGAAGCGCTCTCTCATGTATCGCTGCAACCACTCGCATCATCGATCAACAGAAGGAGATGTTGTGCGGCCCGCCG
CGAAGCCCCGGAAAGGCACGCGGTCTGTTCCACCACCACCGCCACCACCGCCCATGTCATCATCGTCACAAAGAAA
GCTTGCCGCCGCAGTTGCTGGAGCGCCGGCATGCAGCGTCTCAGCACGACACGGAAGGAACCATGGCGTTTCTGCG
GTGGGAGATCCGTCAAGGGGCAATCGAGTTTCAGAAACAGCTCGCATAGCTCATGCTCCTTCTTTTGGGGGGAAGA
AATGCGCGCCGGGCCTAACCCAACTCCATTTCTCTTCCCCTTCCAGAAGGGCTACGCCGATGAAAAAAGACACGCC
ATTGTCACGTGGTCAAGCGGCTGGAGTAGCAGCAGTAGCGGTGGGCGGTGACGGGCAGCTAGAGGCACTGCAGAGG
CGTTACTGGGAACAGTCCCGTGCGATATTGGAGCAGCTTGAAAACATGCTGGCAGCTGAT
```

PROPHYLACTIC AND THERAPEUTIC IMMUNIZATION AGAINST PROTOZOAN INFECTION AND DISEASE

This application is a continuation of U.S. Ser. No. 11/893,951, filed on Aug. 17, 2007, which is a divisional patent application of U.S. Ser. No. 11/015,578, filed on Dec. 17, 2004, now U.S. Pat. No. 7,309,784, which is a divisional application of U.S. patent application Ser. No. 09/518,156, filed Mar. 2, 2000, now U.S. Pat. No. 6,875,584, which claims the benefit of U.S. Provisional Application Ser. No. 60/122,532, filed Mar. 2, 1999, each of which are incorporated herein by reference.

STATEMENT OF GOVERNMENT RIGHTS

This invention was made with government support under grant numbers RO1 AI22070 and AI33106 from the National Institutes of Health. The U.S. government has certain rights in this invention.

BACKGROUND

The etiologic agent of Chagas' disease is an obligate intracellular protozoan parasite, *Trypanosoma cruzi*. In mammalian hosts *T. cruzi* cycles between a trypomastigote stage which circulates in the blood and the amastigote stage which replicates in the cytoplasm of infected host cells (primarily muscle). Chagas' disease is prevalent in almost all Latin American countries including Mexico and Central America, where approximately 18 million people are infected with *T. cruzi* and roughly 50,000 children and adults die of chronic Chagas' disease every year due to lack of effective treatments. More than 90 million are at risk of infection in endemic areas. Additionally, 2-5% of fetus carried by infected mothers in endemic areas are either aborted or born with congenital Chagas' disease. Loss of revenue in terms of productivity lost due to sickness and medical costs have an overwhelming effect on economic growth of these countries. In the U.S., 50-100 thousand serologically positive persons progressing to the chronic phase of Chagas' disease are present, and the number of infected immigrants in developed countries is increasing. Therefore, the risk of transmission of *T. cruzi* to non-infected individuals through blood transfusion and organ transplants from the infected immigrant donors exists.

Attempts to control the vector have been made in an effort to control or prevent *T. cruzi* infection. Government funded programs for the reduviid vector control and blood bank screening in the developing South American countries have been effective in reducing the transmission of *T. cruzi*. However, the operational costs to maintain such control programs, behavioral differences among vector species, the existence of animal reservoirs, and the persistence of parasites in chronically infected patients prevent these control measures alone from completely controlling *T. cruzi* infection.

Chemotherapeutic treatments, a potential means by which parasite load in the acute or chronic phase of the disease development and thereby the severity of disease can be reduced, have been partially successful in controlling *T. cruzi* infection and Chagas' disease. However, the high toxicity of drugs and poor efficacy of available therapeutics have combined to limit the utility of chemotherapy for treatment of both acute and chronic patients. Further, drug therapy reduces the severity of disease in chronically infected individuals, but cannot reverse the damage already done by parasites.

Vaccines for prevention or treatment of *T. cruzi* infection are practically non-existent. Traditional vaccines constituted of heat-inactivated parasites, or subcellular fractions of *T. cruzi* provide a degree of protection from *T. cruzi* infection (M. Basombrio, *Exp. Parasitol.* 71:1-8 (1990); A. Ruiz et al., *Mol. Biochem. Parasitol.* 39:117-125. (1990)). However, these vaccines failed to elicit the protective level of immunity, probably due to loss of important epitopes during inactivation and/or the failure of the antigens to enter the MHC class I pathway of antigen processing and presentation and elicit cell mediated immune responses (J. Monaco, *Immunol. Today* 13:173-179 (1992)). Live attenuated vaccines are capable of entering the MHC class I pathway, and might elicit protective immune responses. However, the danger of reversion of attenuated parasites to virulent strains if attenuation is not complete renders these vaccines impractical. A DNA vaccine containing the gene encoding a trans-sialiadase has been shown to provide prophylactic protection against *T. cruzi* infection in mice (F. Costa et al., *Vaccine* 16:768-774 (1998)), but has not been shown to prevent or reverse disease or to stimulate a $CD8^+$ T cell response in the animal. In another report, specific cellular and humoral immune response in BALB/c mice immunized with an expression genomic library of *T. cruzi* was observed (E. Alberti et al., *Vaccine* 16:608-612 (1998)).

Most vaccine research has centered on attempts to develop prophylactic protein vaccines against *T. cruzi* infection, and has met with little success. The development of subunit vaccines composed of defined antigens which are capable of inducing strong humoral and type 1 T cell responses and reducing the parasite burden has been hindered by the lack of knowledge of the biology of the three developmental stages of *T. cruzi*, the lack of sufficient sequence information on genes expressed in the infective and intracellular stages, and the prevailing scientific view that chronic disease is not associated with persistent parasitic infection but is the result of a parasite-induced autoimmune response. The presence of polyclonal activation of B and T cells during the acute phase of infection, the difficulty in demonstrating the existence of *T. cruzi* in the hearts of hosts with severe cardiac inflammation, and the presence of antigens that are shared or cross-reactive between heart and parasites have been used to promote the idea that anti-heart autoimmune lymphocyte cytotoxicity or humoral immune reactions are responsible for the development of Chagas' disease. A corollary to this view is that vaccination against *T. cruzi* infection or boosting the immune response of infected individuals will exacerbate the disease. On the other hand, immunohistochemical detection of the *T. cruzi* antigens or detection of *T. cruzi* DNA by sensitive in situ PCR or reverse transcriptase (RT)-PCR techniques in chronic chagasic cardiopathy in murine models (Y. Gomes, *Appl. Biochem. Biotechnol.* 66:107-119 (1997); E. Jones et al., *Am. J. Trop. Med. Hyg.* 48:348-57 (1993); M. Reis et al., *Clin. Immunol. Immunopathol.* 83(2):165-172 (1997)) as well as humans (J. Lane et al., *Am. J. Trop. Med. Hyg.* 56:588-595 (1997)) has been reported. Also, a direct correlation between myocardial inflammatory infiltrates and the presence of parasites and development of chronic heart failure in a murine model using heart transplantation (R. Tarleton et al., *Proc. Natl. Acad. Sci. USA.* 94:3932-3937 (1997)), and in chagasic patients using endomyocardial biopsies (M. Higuchi et al., *Clin. Cardiol.* 10:665-670 (1987)) has been demonstrated. See R. Tarleton et al., *Parasitology Today* 15:94 (1999) for a review.

SUMMARY OF THE INVENTION

The present invention is directed to prophylactic and therapeutic immunization of mammals against protozoan infection and disease. Medical uses in humans to prevent or treat protozoan infection, and veterinary uses in other animals to prevent or treat protozoan infection or to control transmission of infection are examples of contemplated applications.

In one aspect, the invention provides a vaccine that is effective to treat or prevent infection of a mammal by a protozoan. Examples of protozoans against which a vaccine of the invention is effective include *Trypanosoma, Leishmania, Toxoplasma, Eimeria, Neospora, Cyclospora* and *Cryptosporidia*. In a particularly preferred embodiment, the vaccine is effective against *T. cruzi* infection and/or disease caused by *T. cruzi*. The vaccine can be a polypeptide vaccine or a polynucleotide vaccine, and can include one or more immunogenic components. A polynucleotide vaccine contains one or more polynucleotides containing a nucleotide coding region that encodes an immunogenic polypeptide derived from the protozoan. Analogously, a polypeptide vaccine contains one or more immunogenic polypeptides derived from the protozoan.

The immunogenic polypeptide included in the vaccine or encoded by a nucleotide coding region included in the vaccine is preferably a surface-associated polypeptide, such as a GPI-anchored polypeptide, or a secreted polypeptide. In embodiments of the vaccine targeted to *T. cruzi*, the immunogenic polypeptide is preferably one that is expressed in a *T. cruzi* amastigote.

The vaccine of the invention preferably stimulates an antibody response or a cell-mediated immune response, or both, in the mammal to which it is administered. More preferably the vaccine stimulate a Th1-biased $CD4^+$ T cell response or a $CD8^+$ T cell response; most preferably, especially in the case of a single component vaccine, the vaccine stimulates an antibody response, a Th1-biased $CD4^+$ T cell response and a $CD8^+$ T cell response. A particularly preferred embodiment of the polynucleotide vaccine of the invention includes a nucleotide coding region encoding a cytokine, to provide additional stimulation to the immune system of the mammal. A particularly preferred embodiment of the polypeptide vaccine of the invention includes an immunogenic polypeptide that contains a membrane translocating sequence, to facilitate introduction of the polypeptide into the mammalian cell and subsequent stimulation of the cell-mediated immune response.

Pharmaceutical compositions containing immunogenic polypeptides or polynucleotides encoding immunogenic polypepdtides together with a pharmaceutical carrier are also provided.

In another aspect, the invention provides a recombinant method of making a vaccine that is effective to treat or prevent infection of a mammal by a protozoan. For example, a multicomponent polynucleotide vaccine is made by inserting two or more nucleotide coding regions encoding an immunogenic polypeptide derived from the protozoan into two or more polynucleotide vectors, then combining the polynucleotide vectors to yield a polynucleotide vaccine. In another example, a multicomponent polypeptide vaccine is made using two or more expression vectors that contain a nucleotide coding region that encodes a membrane transducing sequence, into which nucleotide coding regions encoding an immunogenic polypeptide derived from the protozoan have been inserted in frame. This yields a construct encoding an immunogenic fusion protein that contains membrane transducing sequence linked to the immunogenic polypeptide. Suitable host cells are transformed with the resulting expression vectors, and expression of the immunogenic fusion proteins is initiated. The fusion proteins are purified, optionally destabilized with urea, then combined to yield a polypeptide vaccine.

In another aspect, the invention provides methods for treating or preventing infection of a mammal by a protozoan. A vaccine of the invention can, for example, be administered therapeutically to a mammal harboring a persistent protozoan infection. In one embodiment of the therapeutic administration of the vaccine, administration of the vaccine is effective to eliminate the parasite from the mammal; in another embodiment, administration of the vaccine is effective to prevent or delay chronic debilitating disease in the mammal. Alternatively, a vaccine of the invention can be administered prophylactically to a mammal in advance of infection by the protozoan. In one embodiment of the prophylactic administration of the vaccine, administration of the vaccine is effective to prevent subsequent infection of the mammal by the protozoan. In another embodiment, administration of the vaccine is effective to prevent the development of chronic debilitating disease the mammal after subsequent infection by the protozoan. In yet another embodiment, administration of the vaccine effective to prevent the death of the mammal after subsequent infection by the protozoan.

The method of treating or preventing protozoan infection of a mammal also envisions administering both polynucleotide and polypeptide vaccines prophylactically or therapeutically to a mammal in a protocol that includes multiple administrations of the vaccine. For example, the mammal can be first immunized with a polynucleotide vaccine of the invention, then boosted at a later time with a polypeptide vaccine. Different types of vaccines (i.e., polynucleotide or polypeptide vaccines), or vaccines of a single type containing different components (e.g., plasmid DNA, viral DNA, vaccines including or encoding different immunogenic polypeptides, with or without cytokines or adjuvants) can be administered in any order desired. An example of a serial protocol involves first administering to a mammal a plasmid DNA vaccine, then later administering a polypeptide vaccine or viral vector vaccine. Another example involves first administering to the mammal a viral vector vaccine, followed by administering a polypeptide vaccine.

In another aspect, the invention includes a method for identifying immunogenic protozoan polypeptides from a protozoan genomic library, for use in a polynucleotide vaccine. In one embodiment, the method utilizes expression library immunization (ELI) in mice to identify protozoan polypeptides that elicit an immune response in a mammal effective to prevent the death of the mammal or to arrest or delay the progression of disease in the mammal associated with infection of the mammal by the protozoan. Preferably, the method is used to identify immunogenic polypeptides derived from *T. cruzi*, and BALB/c or B6 mice are immunized. In another embodiment, the method involves (a) preparing a DNA microarray comprising open reading frames of *T. cruzi* genes;

(b) preparing a first probe comprising Cy3-labeled trypomastigote-derived *T. cruzi* cDNA;

(c) preparing a second probe comprising Cy5-labeled amastigote-derived cDNA;

(d) cohybridizing the first and second probes to the microarray to identify at least one gene whose expression is upregulated in *T. cruzi* during the intracellular amastigote stage of the infectious cycle, which gene encodes a candidate immunogenic *T. cruzi* polypeptide; and (e) immunizing mice with the gene to determine whether the gene encodes a *T. cruzi* polypeptide that elicits an immune response in a mammal effective to prevent the death of the mammal or to arrest or delay the progression of disease in the mammal associated with infection of the mammal by *T. cruzi*.

BRIEF DESCRIPTION OF THE FIGURES

FIG. 8 shows induction of cellular immunity by intramuscular immunization of B6 mice with *T. cruzi* antigen-encoding plasmids; (A) Percent specific lysis as an indicator of CTL activity in mice immunized with *T. cruzi* antigen-encoding vectors; (B) Induction of *T. cruzi* specific CTL activity by genetic vaccines is augmented by co-injection of cytokine encoding vectors; (C) Serum level of IFN-γ in DNA immunized mice.

FIG. 17 shows (A) *T. cruzi*-specific serum antibody levels in C3H mice vaccinated with antigen (ASP-1, ASP-2 and TSA-1) encoding vectors with and without cytokines (IL-12 and GM-CSF), together with (B) blood parasite levels and (C) mortality as a function of days post-infection.

FIG. 19 shows the coding region of *T. cruzi* Lyt protein (porin).

DETAILED DESCRIPTION OF THE PREFERRED EMBODIMENTS

Figure 1:
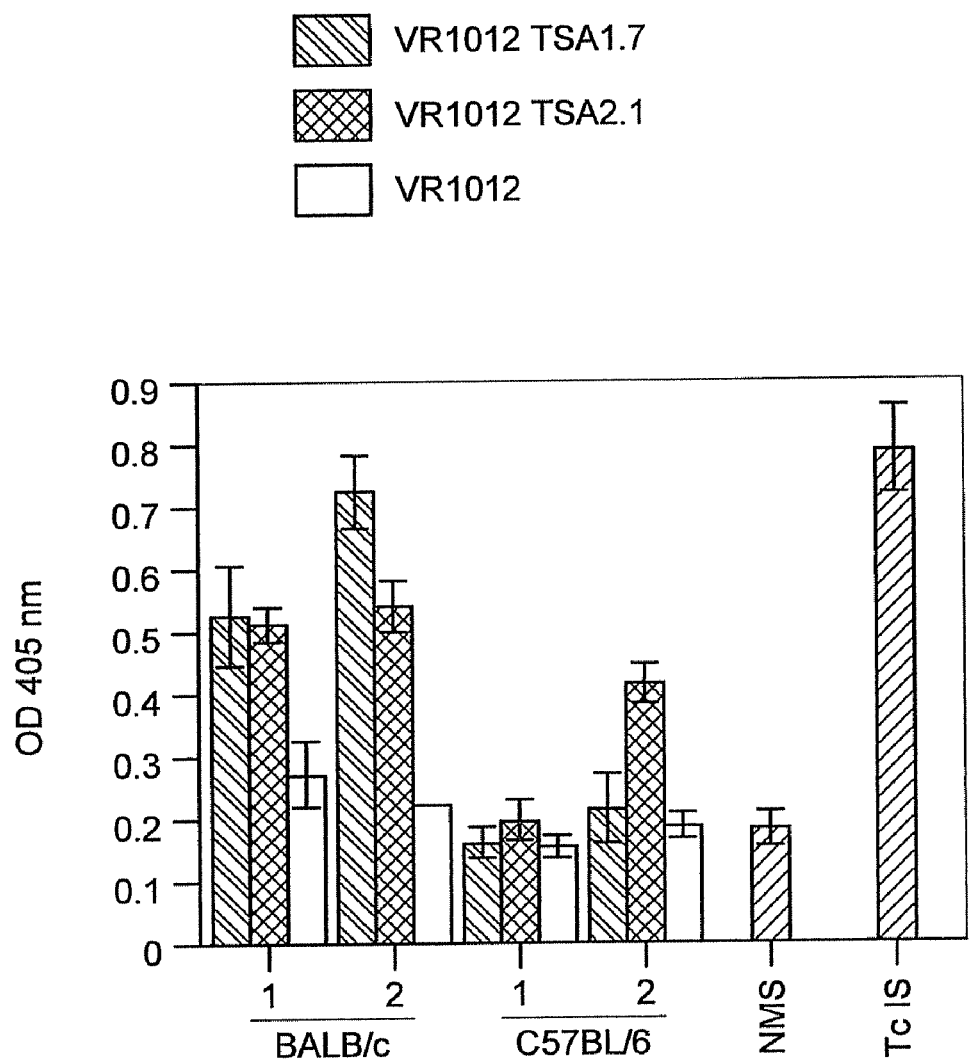
FIG. 1 shows *T. cruzi*-specific serum antibody response in TSA-1 DNA vaccinated BALB/c and B6 mice. The presence of parasite-specific antibodies was assessed by ELISA using a 1:100 dilution of sera pooled from individual tail blood samples (4 to 5 mice per group) and collected 3 and 2 weeks after first (1) and second (2) vaccination. Negative and positive controls were sera from normal mice (NMS) and from mice acutely infected with *T. cruzi* (TcIS).
Figure 2A:
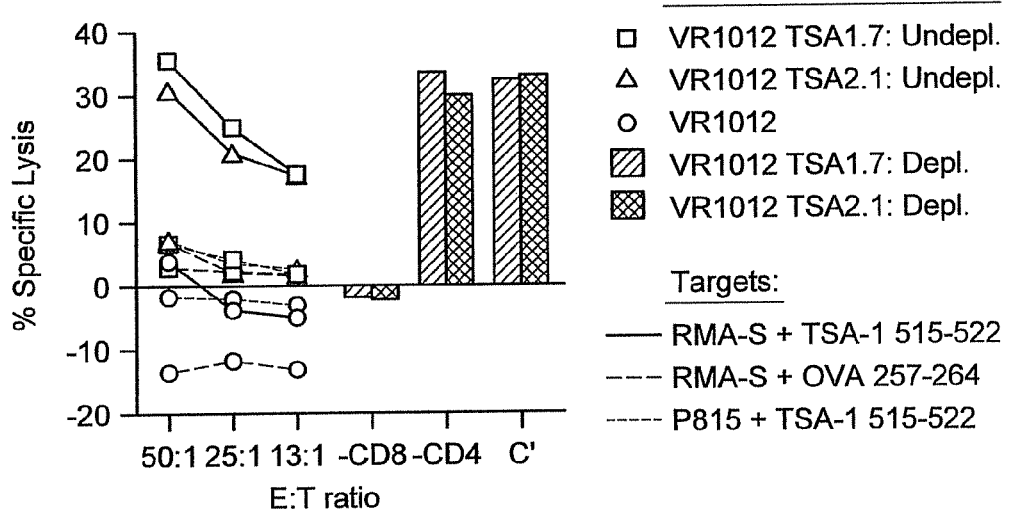
FIG. 2 shows induction of long-lasting TSA-$1_{515-522}$-specific, CD8$^+$ T cell-dependent, MHC class I-restricted CTL in TSA-1 DNA-immunized B6 mice; (A) Immune splenocytes obtained 2 weeks after the second vaccination; (B) Immune splenocytes from DNA vaccinated or *T. cruzi*-infected mice were obtained 7 and 6 months after the second vaccination or parasite challenge, respectively; E:T represents the ratio of effector cell to target cell.
Figure 2B:
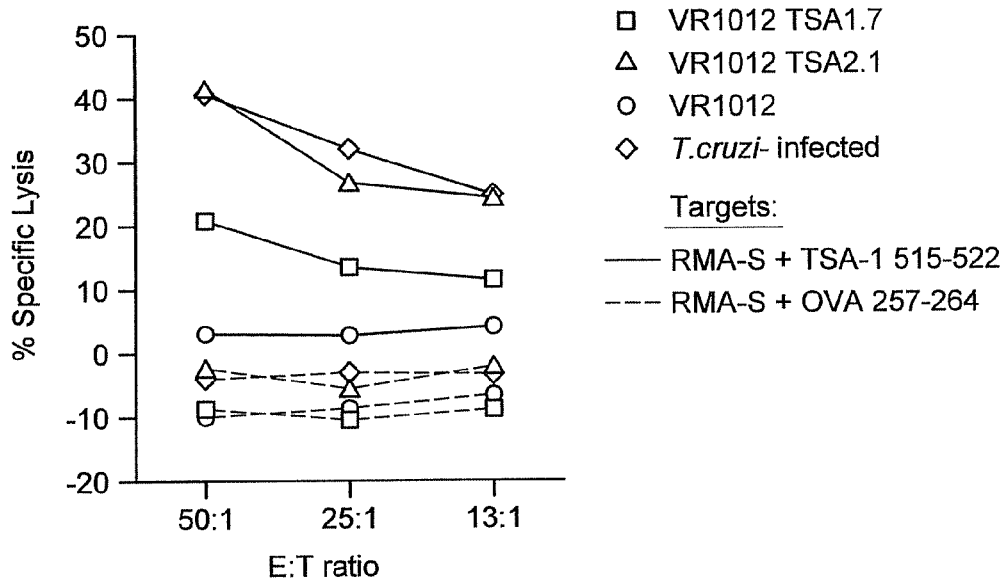
Figure 3A:
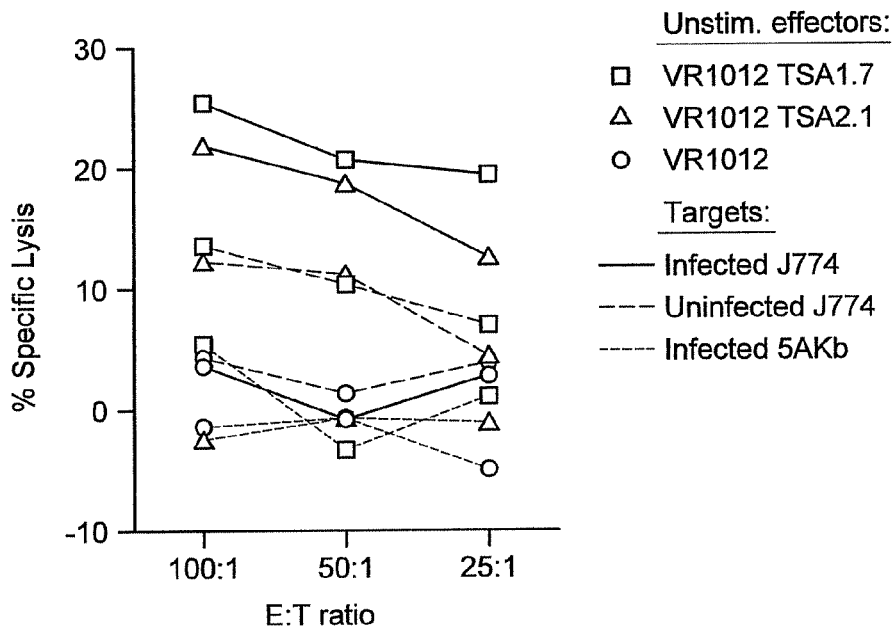
FIG. 3 shows induction of parasite-specific, MHC class I-restricted and CD8$^+$ T cell-dependent CTL response in TSA-1 DNA-immunized BALB/c mice; (A) unstimulated effectors and (B) infected J774-stimulated effectors.
Figure 3B:
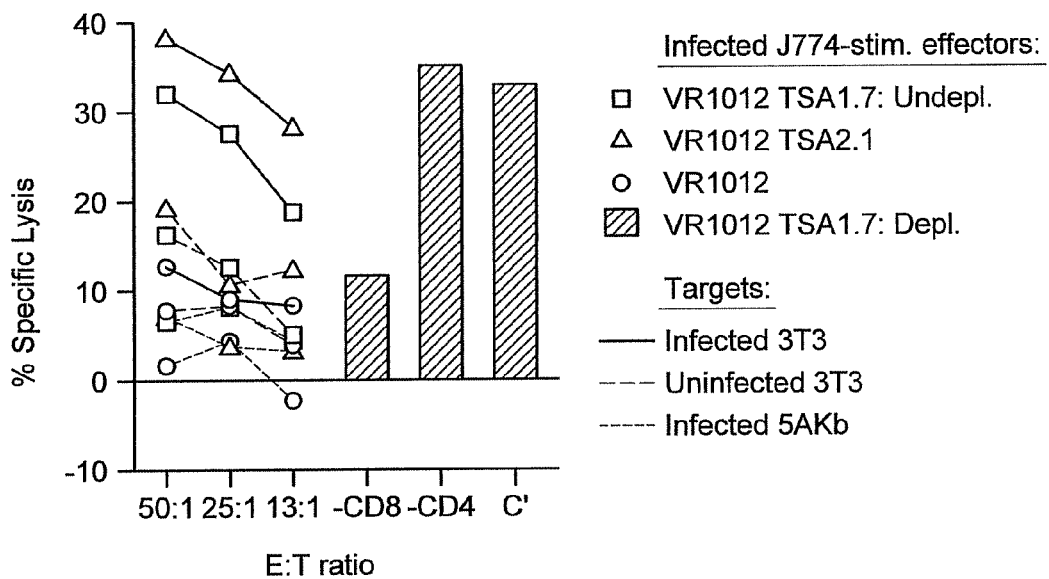

Over 100 natural mammalian hosts are known for *T. cruzi*, and *T. cruzi* can be transmitted to a human from another animal host. Any mammalian host can be immunized in accordance with the invention. Preferred vaccine recipients include humans, domestic animals such as dogs and cats, rodents and wildlife animals. Preferably, the mammal that is immunized is a dog, a cat, or a human.

Humoral (Antibody-Mediated) and Cell-Mediated Immunity to *T. cruzi*

In the mammalian host, *T. cruzi* cycles between a dividing intracellular stage (the amastigote) and a non-replicative extracellular trypomastigote than which circulates in the blood. The presence of two developmental stages of *T. cruzi* in mammalian hosts provides two anatomically and (to some degree) antigenically distinct targets of immune detection—the trypomastigotes in the bloodstream and the amastigotes in the cytoplasm of infected cells. The intracellular location of amastigotes of *T. cruzi* has long been considered a “hiding place” for the parasite wherein it is not susceptible to immune recognition and control. Thus, studies of immunity to *T. cruzi* have largely centered around the recognition and elimination of the extracellular stage.

The present invention challenges the conventional approach of vaccinating against trypomastigotes by providing, in a preferred embodiment, compositions and methods by which immune responses to amastigotes can be potentiated by therapeutic or prophylactic polynucleotide or polypeptide vaccines. To this end, the approach of the present invention involves stimulating or promoting immune recognition of the infected host cell and the antigens involved in this recognition. Convention is further challenged by the scientific basis of the present invention: that disease development following initial *T. cruzi* infection is not an autoimmune response but instead is dependent upon the persistent presence of parasites in tissues. Previous studies based on the autoimmune theory of disease development predicted that genetic immunization against *T. cruzi* would exacerbate disease development, however it is shown in Example II that genetic immunization of mice prior to exposure to *T. cruzi* reduces disease development.

The antibody response to *T. cruzi* trypomastigotes has been well-studied and numerous specific targets of this response described. However, attempts to vaccinate experimental hosts using these target molecules in protocols that elicit primarily antibody responses (accompanied by little to no cellular immune response) have not been very fruitful. Without intending to be bound by theory, it is proposed that although antibodies may be necessary for control of *T. cruzi* infection, their role is likely secondary in importance to cell-mediated immune responses. For example, mice lacking the ability to make antibodies by virtue of the muMT targeted deletion live significantly longer than do mice lacking either $CD4^+$ or $CD8^+$ T cells but do eventually die, even when infected with very low numbers of parasites. It is of course possible that vaccine-induced antibody responses fail to provide good protection because the wrong target molecules are used for the immunization or because non-protective isotypes of antibodies are elicited by the immunization. However, we believe it is more likely that protective immunity cannot be achieved by induction of parasite-specific antibodies alone; instead, this antibody response is preferably accompanied by a potent cell-mediated immune response.

Induction of T helper cell responses skewed toward the production of type 1 cytokines such as IL-2 and IFN-γ are also of substantial importance in immunity to *T. cruzi*. The Th1 set of cytokines enhance macrophage activation for killing of *T. cruzi* via a nitric oxide (NO) dependent mechanism (e.g., J. Silva et al., *Infect. Immun.* 63:4862-4867 (1997)) and are also likely to be important in the induction of protective antibody responses and as helper factors in the cytotoxic T-lymphocyte (CTL) response. Infections in mice depleted of Th1 cytokines and in gene-knockout mice provide solid evidence that Th1 responses associate with protection from *T. cruzi* and Th2 responses associate with susceptibility. In our hands, mice lacking the ability to produce type 1 cytokines by virtue of the absence of the STAT4 gene product are extremely susceptible to *T. cruzi* infection while STAT6 knockout mice which fail to make type 2 cytokines are more resistant to infection than are wild-type mice (R. Tarleton et al., *Parasitology Today* 15:94-99 (1999)).

It is demonstrated herein that a third effector mechanism is important to immune control of *T. cruzi*, i.e., the class I MHC-restricted $CD8^+$ T cell response. Cytoplasmic pathogens are recognized by the immune system via class I MHC-presented peptides. During the processes of differentiation, replication and metabolism, *T. cruzi* releases a variety of proteins into the host cell. All cytoplasmic proteins are susceptible to degradation by the proteasome and the resulting peptides can be transported into the endoplasmic reticulum via transporters associated with antigen processing (TAPs). In vertebrate cells, these peptides have the potential to associate with newly synthesized class I major histocompatibility complex (MHC) molecules and to be displayed as class I MHC-peptide complexes on the cell surface. This process allows essentially all vertebrate cells to sample the contents of the cytoplasm and to display to the immune system portions of the proteins being expressed within. In the case of normal cellular proteins, the peptides displayed in association with class I MHC are presumably ignored by the immune system. However when peptides from mutated self proteins or from proteins encoded by invading viruses, bacteria or protozoans are displayed, $CD8^+$ T cells capable of recognizing the foreign peptide-self MHC complex can initiate the responses capable of killing the infected cells or controlling the growth of the pathogen within. TSA-1, ASP-1 and ASP-2, GPI-anchored proteins expressed in *T. cruzi* primarily during the amastigote stage are examples of targets of the CTL response in *T. cruzi* infected mice (Example II). Humans with chronic *T. cruzi* infections recognize these same target antigens (B. Wizel et al., *J. Clin. Invest.* 102:1062-71 (1998)). It should be understood that although most $CD8^+$ T cells are cytotoxic T-cell lymphocytes (CTLs) some can, alternatively or in addition, produce cytokines, and this cytokine-producing activity may also be an important result of the stimulation of a $CD8^+$ T cell immune response.

Without intending to be bound by theory, it is believed that proteins anchored by glycosylphosphatidylinositol (GPI) in *T. cruzi* may stimulate all three of these distinct immune responses, thereby generating a broader protection against *T. cruzi* than was previously possible. The failure of previous attempts at vaccination in *T. cruzi* is likely due to the fact that investigators have largely focused on induction of only one or two of these responses, principally antibody production and, to a lesser extent, $CD4^+$ T cell responses. The majority of surface proteins in trypomastigotes and amastigotes of *T. cruzi* are GPI-anchored and many of these surface proteins both elicit and are bound by antibodies. In addition, the GPI anchoring mechanism in *T. cruzi* appears to be very sloppy with a significant portion of proteins targeted for GPI addition being secreted without the addition of a GPI anchor (N. Garg et al., *J. Biol. Chem.* 272:12482-12491 (1997)). In the case of amastigotes, these secreted proteins lacking GPIs enter the host cell cytoplasm, are presented by class I MHC molecules and elicit the production of CTL responses. On extracellular amastigotes and trypomastigotes, these same proteins in a surface-anchored form sensitize parasites to detection by antibodies specific for the proteins. Lastly, significant class II MHC-restricted, $CD4^+$ T cell reactivity is elicited by GPI-anchored proteins. Thus GPI anchored proteins appear to be excellent targets for stimulation of protective antibody, Th1-biased $CD4^+$ T cell responses, and $CD8^+$ T cell responses.

Types of Vaccine-Induced Immunity to *T. cruzi*

Vaccine-induced immunity to *T. cruzi* according to the present invention can take a variety of forms. In one embodiment, the vaccine induces sterilizing immunity against *T. cruzi* in the mammalian host. "Sterilizing immunity" means that a vaccinated, pathogen-free mammal will, when exposed to the pathogen, not develop a persistent infection but instead will totally clear the pathogen (prophylactic vaccination); and also that a pathogen-infected mammal will clear the pathogen and be free of the infection and disease following administration of the vaccine (therapeutic vaccination). However, because a high percentage—well over 50%—of people infected with *T. cruzi* fail to develop chronic disease symptoms even though they appear to remain infected for their entire lives, it is expected based on the results in the mouse model reported in the Examples, below, that a balance can be reached in an infected host between an effective immune response and parasite persistence without the development of clinical disease. Thus, in another embodiment, the vaccine elicits a set of responses that are sufficient to delay or, preferably, prevent disease development in *T. cruzi* infected individuals despite the persistence of parasites. Like a vaccine that induces "sterilizing immunity," this vaccine can be administered prophylactically, in advance of infection, or therapeutically, after infection but before the development of a chronic debilitating disease state. This embodiment of the vaccine is suitable for delivery to individuals who are infected and at risk of developing disease.

Prophylactic and Therapeutic Immunization

Accordingly, in a preferred embodiment, the present invention is directed to both prophylactic and therapeutic immunization against *T. cruzi* infection and the chronic disease state, known as Chagas' disease, that often eventually follows initial *T. cruzi* infection. Therapeutic administration of the polynucleotide or polypeptide vaccine to infected subjects is effective to delay or prevent the progression of the *T. cruzi* infection to a chronic disease state, and also to arrest or cure the chronic disease state that follows *T. cruzi* infection. Prophylactic administration of the polynucleotide or polypeptide vaccine to uninfected subjects is effective to reduce either or both if the morbidity and mortality associated with infection by *T. cruzi*. Further, if an uninfected, vaccinated subject is subsequently infected with *T. cruzi*, the vaccine is effective to prevent progression of the initial infection to a chronic disease state. As discussed in more detail hereinbelow, the vaccine can contain or encode a single immunogenic polypeptide or multiple immunogenic polypeptides.

In another preferred embodiment, the invention is directed to therapeutic immunization against other protozoans using a polynucleotide or polypeptide vaccine that preferably stimulates an antibody response, a cell-mediated $CD4^+$ immune response and a $CD8^+$ immune response. The vaccine is administered to a mammal infected with a protozoan in the form of a persistent intracellular presence or state. It is contemplated that the vaccine can cause the mammal to either clear the parasite (thereby effecting a "cure"), or at least arrest development of disease, thereby preventing or delaying progression of the disease to a chronic debilitating state. For example, the multicomponent vaccine of the invention is expected to be effective against *Leishmania, Toxoplasma, Eimeria, Neospora, Cyclospora* and *Cryptosporidia* as well as *T. cruzi*. It is to be understood that the immunogenic polypeptides used in the vaccine, or the nucleotide sequences encoding them, are derived from the protozoan against which the vaccine is directed. Methods for identifying nucleotide sequences encoding such polypeptides from a protozoan genomic library using, for example, expression library immunization (ELI) or DNA microarray analysis are described below for *T. cruzi* but are equally applicable to other protozoans.

Advantages of a Genetic Vaccine

The choice of polynucleotide delivery as an immunization technique offers several advantages over other vaccine or antigen delivery systems. Vaccines containing genetic material are favored over traditional vaccines because of the ease of construction and production of the vectors, the potential for modification of the sequences by site-directed mutagenesis to enhance the antigenic potency of the individual epitopes or to abolish epitopes that may trigger unwanted response, in the case of DNA vaccines, the stability of DNA, the lack of the dangers associated with live and attenuated vaccines, their ability to induce both humoral and cell mediated immunity and, in particular, $CD8^+$ T cell responses, and the persistence of the immune responses. Successful induction of humoral and/or cellular immune responses to plasmid-encoded antigens using various routes of gene delivery have been shown to provide partial or complete protection against numerous infectious agents including influenza virus, bovine herpes virus I, human hepatitis B virus, human immunodeficiency virus-1, as well as parasitic protozoans like *Plasmodium* and *Leishmania* (J. Donnelly et al., *Ann. Rev. Immunol.* 15:617-648 (1997)). Representative papers describing the use of DNA vaccines in humans and primates include V. Endresz et al. (*Vaccine* 17:50-58 (1999)), M. McCluskie et al. (*Mol. Med.* 5:287-300 (1999)), R. Wang et al. (*Infect. Immun.* 66:4193-202 (1998)), S. Le Borgne et al. (*Virology* 240:304-315 (1998)), C. Tacket et al. (*Vaccine* 17:2826-9 (1999)), T. Jones et al. (*Vaccine* 17:3065-71 (1999)) and R. Wang et al. (*Science* 282(5388):476-80 (1998)). The ability to enhance the immune response by the co-delivery of genes encoding cytokines is also well-established.

Polynucleotide Vaccine

The polynucleotide vaccine of the invention includes at least one, preferably at least two, nucleotide coding regions, each coding region encoding an immunogenic polypeptide component from *T. cruzi*. When it contains two or more nucleotide coding regions, the polynucleotide vaccine is referred to herein as a "multicomponent" polynucleotide vaccine. It is desirable to minimize the number of different immunogenic polypeptides encoded by the nucleotide coding regions in the polynucleotide vaccine; however, it is nonetheless contemplated that a polynucleotide vaccine that generates the highest level of protection will encode 10 or more immunogenic polypeptides. The polynucleotide vaccine can contain DNA, RNA, a modified nucleic acid, or any combination thereof. Preferably, the vaccine comprises one or more cloning or expression vectors; more preferably, the vaccine comprises a plurality of expression vectors each capable of autonomous expression of a nucleotide coding region in a mammalian cell to produce at least one immunogenic polypeptide or cytokine, as further described below. An expression vector preferably includes a eukaryotic promoter sequence, more preferably the nucleotide sequence of a strong eukaryotic promoter, operably linked to one or more coding regions. A promoter is a DNA fragment that acts as a regulatory signal and binds RNA polymerase in a cell to initiate transcription of a downstream (3' direction) coding sequence; transcription is the formation of an RNA chain in accordance with the genetic information contained in the DNA. A promoter is "operably linked" to a nucleic acid sequence if it is does, or can be used to, control or regulate transcription of that nucleic acid sequence. The invention is not limited by the use of any particular eukaryotic promoter, and a wide variety are known; preferably, however, the expression vector contains a CMV or RSV promoter. The promoter can be, but need not be, heterologous with respect to the host cell. The promoter used is preferably a constitutive promoter.

A vector useful in the present invention can be circular or linear, single-stranded or double stranded and can be a plasmid, cosmid, or episome but is preferably a plasmid. In a preferred embodiment, each nucleotide coding region (whether it encodes an immunogenic polypeptide or a cytokine) is on a separate vector; however, it is to be understood that one or more coding regions can be present on a single vector, and these coding regions can be under the control of a single or multiple promoters.

There are numerous plasmids known to those of ordinary skill in the art useful for the production of polynucleotide vaccines. Preferred embodiments of the polynucleotide vaccine of the invention employ constructs using the plasmids VR1012 (Vical Inc., San Diego Calif.), pCMVI.UBF3/2 (S. Johnston, University of Texas) or pcDNA3.1 (InVitrogen Corporation, Carlsbad, Calif.) as the vector. Plasmids VR1012 and pCMVI.UBF3/2 are particularly preferred. In addition, the vector construct can contain immunostimulatory sequences (ISS), such as unmethylated dCpG motifs, that stimulate the animal's immune system. Other possible additions to the polynucleotide vaccine constructs include nucleotide sequences encoding cytokines, such as granulocyte macrophage colony stimulating factor (GM-CSF), interleukin-12 (IL-12) and co-stimulatory molecules such B7-1, B7-2, CD40. The cytokines can be used in various combinations to fine-tune the response of the animal's immune system, including both antibody and cytotoxic T lymphocyte responses, to bring out the specific level of response needed to control or eliminate the $T.$ $cruzi$ infection. The polynucleotide vaccine can also encode a fusion product containing the antigenic polypeptide and a molecule, such as CTLA-4, that directs the fusion product to antigen-presenting cells inside the host. Plasmid DNA can also be delivered using attenuated bacteria as delivery system, a method that is suitable for DNA vaccines that are administered orally. Bacteria are transformed with an independently replicating plasmid, which becomes released into the host cell cytoplasm following the death of the attenuated bacterium in the host cell. An alternative approach to delivering the polynucleotide to an animal involves the use of a viral or bacterial vector. Examples of suitable viral vectors include adenovirus, polio virus, pox viruses such as vaccinia, canary pox, and fowl pox, herpes viruses, including catfish herpes virus, adenovirus-associated vector, and retroviruses. Exemplary bacterial vectors include attenuated forms of *Salmonella, Shigella, Edwardsiella ictaluri, Yersinia ruckerii*, and *Listeria monocytogenes*. Preferably, the polynucleotide is a vector, such as a plasmid, that is capable of autologous expression of the nucleotide sequence encoding the immunogenic polypeptide.

Plasmids and other delivery systems are made using techniques well-known in the art of molecular biology, as exemplified in the following examples. The invention should be understood as including methods of making and using the polynucleotide vaccine.

Polypeptide Vaccine

The polypeptide vaccine of the invention includes at least one, preferably at least two, immunogenic polypeptides from *T. cruzi*. As with the polynucleotide vaccine, it is desirable to minimize the number of different immunogenic polypeptides supplied in the vaccine; however, it is nonetheless contemplated that a polypepetide vaccine that generates the highest level of protection will contain 10 or more immunogenic polypeptides.

Because a $CD8^+$ T cell response cannot normally be directly triggered by the administration of a conventional protein subunit vaccine, the immunogenic polypeptides contained in the polypeptide vaccine preferably include one or more membrane transporting sequences (MTS) fused to their N-terminus or C-terminus or both. A membrane transporting sequence allows for transport of the immunogenic polypeptide across a lipid bilayer, allowing it to be delivered to the inside of a mammalian cell. In a particularly preferred embodiment, the immunogenic polypeptides are shocked with urea, as described further in Example VIII, prior to administration as a vaccine. From there, portions of the polypeptide can be degraded in the proteasome, and the resulting peptides can be displayed as class I MHC-peptide complexes on the cell surface. In this way, a polypeptide vaccine can stimulate a CD8+ T cell immune response. A polypeptide vaccine of the invention is optionally adjuvanted using any convenient and effective adjuvant, as known to one of skill in the art.

The invention should be understood as including methods of making and using the polypeptide vaccine.

Immunogenic Polypeptide

An "immunogenic polypeptide" from a protozoan is a polypeptide derived from the protozoan that elicits in a mammalian host an antibody-mediated immune response (i.e., a "B cell" response or humoral immunity), a cell-mediated immune response (i.e., a "T cell" response), or a combination thereof. A cell-mediated response can involve the mobilization helper T cells, cytotoxic T-lymphocytes (CTLs), or both. Preferably, an immunogenic polypeptide elicits one or more of an antibody-mediated response, a $CD4^+$ Th1-mediated response (Th1: type 1 helper T cell), and a $CD8^+$ T cell response. It should be understood that the term "polypeptide" as used herein refers to a polymer of amino acids and does not refer to a specific length of a polymer of amino acids. Thus, for example, the terms peptide, oligopeptide, and protein are included within the definition of polypeptide.

An immunogenic polypeptide for use in a *T. cruzi* vaccine according to the invention can be one that is expressed by *T. cruzi* in the extracellular (trypomastigote) stage, in the intracellular (amastigote) stage, or during both stages of the life cycle. Preferably, the immunogenic polypeptide is expressed by a *T. cruzi* amastigote; more preferably, it is expressed by the amastigote in the early stage of infection, within about 24 hours from initial infection. Also preferably, the immunogenic polypeptide is a membrane surface-associated polypeptide or a secreted polypeptide. Surface associated-immunogenic polypeptides include, for example, *T. cruzi* proteins that are anchored to the plasma membrane by glycosylphosphotidylinositols, or GPIs, and those that have transmembrane domains or are otherwise embedded in the plasma membrane. One class of polypeptides that exemplifies immunogenic polypeptides according to the invention is the trans-sialidase family of proteins, such as TSA-1 (*T. cruzi* Peru; D. Fouts et al., *Mol. Biochem. Parasitol.* 46:189-200 (1991); GenBank Acc. Number M58466), ASP-1 and ASP-2 (*T. cruzi* Brazil; M. Santos et al., *Mol. Biochem. Parasitol.* 86:1-11 (1997); GenBank Ace. Number U74494)) and ASP-2 (*T. cruzi* Brazil; H. Low et al., *Mol. Biochem. Parasitol.* 88:137-149 (1997); GenBank Acc. Number U77951), which are found in both secreted and surface-displayed forms; other examples are proteins that are secreted upon entry of the host cells by *T. cruzi*, such as the hemolysin, and the Lyt1 protein (porin).

In a preferred embodiment, the polynucleotide vaccine of the invention contains at least one nucleotide coding region that encodes an immunogenic polypeptide that constitutes in an amastigote-expressed $CD8^+$ T cell target molecule. Analogously, the polypeptide vaccine of the invention contains at least one immunogenic polypeptide that constitutes in an amastigote-expressed $CD8^+$ T cell target molecule As noted above, the induction of T helper cell responses skewed toward the production of type 1 cytokines such as IL-2 and IFN-γ, which presumably potentiate antibody responses and macrophage activation, is also of substantial importance in immunity to *T. cruzi*, as is antibody production. Thus, in a particularly preferred embodiment, the vaccine of the invention contains a plurality of immunogenic polypeptides (or, in the case of a polynucleotide vaccine, a plurality of nucleotide coding regions encoding immunogenic polypeptides), such that in combination the immunogenic polypeptides stimulate all three immune responses identified herein, namely a protective antibody response, a Th1-biased CD4$^+$ T cell response, and a CD8$^+$ T cell responses.

An immunogenic polypeptide used in the compositions of the invention is not limited to a naturally occurring immunogenic protozoan polypeptide; it can include an immunogenic fragment or immunogenic analog of a protozoan polypeptide. Likewise the immunogenic polypeptide can be a multivalent polypepdtide that has been engineered to include epitopes obtained from different immunogenic polypeptides of the protozoan. An immunogenic analog of an immunogenic protozoan polypeptide is a polypeptide having one or more amino acid substitutions, insertions, or deletions relative to an immunogenic protozoan polypeptide, such that immunogenicity is not entirely eliminated. Substitutes for an amino acid are preferably conservative and are selected from other members of the class to which the amino acid belongs. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Examples of preferred conservative substitutions include Lys for Arg and vice versa to maintain a positive charge; Glu for Asp and vice versa to maintain a negative charge; Ser for Thr so that a free —OH is maintained; and Gln for Asn to maintain a free $NH_2$. Immunogenic fragments of an immunogenic protozoan polypeptide are immunogenic protozoan polypeptides that are truncated at either or both of the N-terminus or C-terminus, without eliminating immunogenicity. Preferably, an immunogenic fragment contains an epitope recognized by a host T cell. Fragments of an immunogenic *T. cruzi* protein contain at least about eight amino acids, preferably at least about 12 amino acids, more preferably at least about 20 amino acids.

Cytokines

Preferably, the polynucleotide vaccine further includes at least one nucleotide coding region encoding a cytokine. Preferred cytokines include interleukin-12 (IL-12), granulocyte-macrophage colony-stimulating factor (GM-CSF), interleukin-6 (IL-6), interleukin-18 (IL-18), γ-interferon, α,β-interferons, and chemokines. Especially preferred cytokines include IL-12 and GM-CSF.

Pharmaceutical Compositions

The polynucleotide and polypeptide vaccines of the invention are readily formulated as pharmaceutical compositions for veterinary or human use. The pharmaceutical composition optionally includes excipients or diluents that are pharmaceutically acceptable as carriers and compatible with the genetic material. The term "pharmaceutically acceptable carrier" refers to a carrier(s) that is "acceptable" in the sense of being compatible with the other ingredients of a composition and not deleterious to the recipient thereof. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, salts, and/or adjuvants which enhance the effectiveness of the immune-stimulating composition. Methods of making and using such pharmaceutical compositions are also included in the invention.

Administration of the Polynucleotide Vaccine

The polynucleotide vaccine of the invention can be administered to the mammal using any convenient method, such as intramuscular injection, topical or transdermal application to the mammal's skin, or use of a gene gun, wherein particles coated with the polynucleotide vaccine are shot into the mammal's skin. The amount of polynucleotide administered to the mammal is affected by the nature, size and disease state of the mammal as well as the delivery method; for example, typically less DNA is required for gene gun administration than for intramuscular injection. Further, if a polynucleotide encoding a cytokine is co-delivered with nucleotide coding regions encoding the immunogenic polypeptide from *T. cruzi*, the amount of polynucleotide encoding the immunogenic polypeptide from *T. cruzi* in the vaccine is optionally reduced.

Hundreds of publications have now reported the efficacy of DNA vaccines in small and large animal models of infectious diseases, cancer and autoimmune diseases (J. Donnelly et al., *Rev. Immunol.* 15:617 (1997). Vaccine dosages for humans can be readily extended from the murine models by one skilled in the art of genetic immunization, and a substantial literature on genetic immunization of humans is now available to the skilled practitioner. For example, Wang et al. (*Science* 282:476-480 (1998)) vaccinated humans with plasmid DNA encoding a malaria protein, and the same group has developed a plan for manufacturing and testing the efficacy of a multigene *Plasmodium falciparum* liver-stage DNA vaccine in humans (Hoffman et al., *Immunol. Cell Biol.* 75:376 (1997)). In general, the polynucleotide vaccine of the invention is administered in dosages that contain the smallest amount of polynucleotide necessary for effective immunization. It is typically administered to human subjects in dosages containing about 20 μg to about 2500 μg plasmid DNA; in some instances 500 μg or more of plasmid DNA may be indicated. Typically the vaccine is administered in two or more injections at time intervals, for example at four week intervals.

Administration of the Polypeptide Vaccine

Like the polynucleotide vaccine, the polypeptide vaccine can be administered to the mammal using any convenient method, such as intramuscular or intraperitoneal injection, topical administration, oral or intranasal administration, inhalation, perfusion and the like. The amount of polypeptide administered to the mammal is affected by the nature, size and disease state of the mammal, as well as by the delivery method. Intraperitoneal injection of 25 to 50 ug of polypeptide containing a membrane transducing sequence has been shown to result in import of the protein into nearly 100% of murine blood and spleen cells within 20 minutes (Schwarze et al., *Science* 285:1569-1572 (1999)) and the sensitization of cytotoxic T cells (M.-P. Schutze-Redelmeier et al., *J. Immunol.* 157:650-655 (1996)). Useful dosages of the polypeptide vaccine for humans can be readily determined by evaluating its activity in vivo activity in mice.

Administration of a Combination of Polynucleotide Vaccine and Polypeptide Vaccine The invention contemplates administration of both a polynucleotide vaccine and a polypeptide vaccine to a mammal in a serial protocol. For example, a plasmid-based DNA vaccine may be administered to a mammal to "prime" the immune system, followed by the one or more administrations of a polypeptide vaccine or a viral vaccine (e.g., vaccinia vector carrying the genes that encode the immunogenic polypeptides and, optionally, cytokines) to further stimulate the mammal's immune system. The order of administration of the different types of vaccines, and the nature of the vaccines administered in any given dose (e.g., polypeptide vaccine, plasmid vaccine, viral vector vaccine) can be readily determined by one of skill in the art to invoke the most effective immune response in the mammal.

Methods of Screening for *T. cruzi* Nucleotide Sequences Encoding Candidate Immunogenic Polypeptides As noted above, the polynucleotide vaccine of the invention can include one or more nucleotide coding regions encoding a polypeptide from the trans-sialidase family of proteins, such as TSA-1, ASP-1 and ASP-2, or a polypeptide that is secreted upon entry of the host cells by *T. cruzi*, such as the hemolysin or Lyt1 protein. Likewise, the polypeptide vaccine of the invention can contain one or more of these polypeptides. It is contemplated that other polypeptides, as yet unidentified, may also be included in (or encoded by nucleotide sequences included in) these vaccines in order to produce the desired type and level of immune response in the mammal. To identify candidate polypeptides, the invention provides a genome-based method for evaluating the ability of protozoan polypeptides to stimulate a mammal's immune response.

The classical approach to vaccine development, particularly with parasites, has been to use somewhat rational approaches to identify potential vaccine candidates, clone the genes and express the candidate proteins, and finally to test the ability of the proteins to induce an effective immune response. This approach has a number of serious drawbacks. First, the rational identification of candidates is not always so easy to do "rationally." Second, this approach makes assumptions about the type of immune response that should be protective, sometimes on the basis of not so firm data. Third it is extremely time consuming and with no real guarantee that at the end of the 3-5 years it might take to accomplish, the single candidate which is the focus of the work will be even marginally effective as a vaccine. Fourth, it is expensive. And fifth, in many cases the proteins cannot be delivered in a way that will generate sufficient and appropriate (i.e. protective) immune responses.

The novel method for identifying additional immunogenic polypeptides that is provided by the present invention relies upon genome-based approaches that utilize both rational and unbiased techniques for vaccine discovery and genetic immunization for vaccine delivery. These approaches integrate the current understanding of immunity and disease in protozoan infection with, in the case of *T. cruzi*, information emerging from genome projects with trypanosomitids, as well as new technical developments for genome analysis and vaccine delivery, while continuing to make use of the strength of the mouse model of protozoan infection.

In one embodiment of the method for screening for vaccine candidates in *T. cruzi*, the invention utilizes expression library immunization (ELI) (M. Barry et al, Nature. 377:632-5 (1995). ELI provides an unbiased method (i.e. makes no assumptions about what types of molecules or what types of immune responses are necessary for protection) for screening potentially the entire genome of a protozoan. A genetic immunization technique is used to select protective antigen encoding genes from the pathogen DNA. For this, a eukaryotic expression library of the pathogen DNA is constructed in a genetic immunization vector. Animals are immunized with fractions of the library, and then monitored for the induction of immune responses and protection from challenge infection. Sub-groups of the genomic library which provide protection are then "sibbed" in stages into smaller fractions and tested for elicitation of protective immune responses and resistance to infection. A series of immunization/challenge studies are done until individual protective genes are identified. Advantages associated with ELI include: (i) instead of cloning gene by gene and testing the immunogenic properties of each gene product, ELI screens the whole genome and selects for the protective genes, (ii) candidate genes are selected by ELI based upon the immune system itself, therefore knowledge of the parasite biology or the immunogenic properties of individual antigens is not required, (iii) ELI is not only a cheaper, faster and more effective method for gene discovery, it might prove to be the only avenue for the generation of an effective vaccine for pathogens like *T. cruzi* which are difficult to grow, maintain and attenuate for their use as vaccine, and (iv) ELI utilizes a vaccine delivery method for the discovery of immunogenic genes. Conveniently, with the identification of new genes which can be used to constitute the anti-*T. cruzi* genetic vaccine, the vaccine delivery method is established as well.

Another embodiment of the screening method of the invention utilizes DNA microarrays. DNA microarrays provide a tool to monitor the expression of many (or all, if one chooses) of the genes in the genome of a protozoan. Genes whose expression is upregulated in the parasite soon after infection of the host cell are identified, since the protein products of such genes would be among the first to reach the class I MHC processing and presentation pathway and thus the early indicators to the immune system of the infection status of host cells.

Vaccine candidates are tested singly and in combination under various conditions in murine models for protection of mice from both lethal infection and from development of severe disease. Whether or not these molecules are recognized by humans infected with the protozoan can be readily determined using ELISA and CTL assays as described in the following examples.

Murine Model for Chagas' Disease

The most widely characterized animal model for Chagas' disease is the mouse. The mouse model parallels human infection in that 1) both acute and chronic stages of infection are generally present, 2) recovery from the acute infection is dependent on the development of a non-sterilizing immune response, 3) chronically infected mice develop pathological and electrocardiographic changes similar to those seen in human Chagas' disease and 4) many of the immune mechanisms thought to be important in immune control of the parasite in humans are also present in the mouse model. During *T. cruzi* infection, both chagasic patients and experimental animals produce strong immune responses to molecules expressed in the infective non-replicative trypomastigote stage and the replicative amastigote forms (N. Andrews et al., *Am. J. Trop. Med. Hyg.* 40:46-9 (1989); A. Krettli, *J. Immunol.* 128:2009-2012 (1982)). A World Health Organization (WHO) working group concluded that the mouse best model system for studying the various aspects of Chagas' disease (WHO Report, 1984).

Genetic immunization has been demonstrated herein for BalbC mice (single component genetic vaccine, TSA-1) and B6 mice (multiple component genetic vaccine, TSA-1, ASP-1 and ASP-2) using infection with Brazil *T. cruzi*. Standard polynucleotide vaccine dosages for mice range from 1 ng to 100 μg of polynucleotide. Both murine systems make good human models since initial infection with *T. cruzi* is not generally lethal, and a chronic disease state typically develops following initial infection. Prophylactic genetic immunization was also tested in C3H mice (multiple component genetic vaccine), but with less promising results. However, C3H mice represent a murine mode that is extremely susceptible to infection with *T. cruzi* (typically 100% mortality is observed upon initial infection) and thus is not as representative of *T. cruzi* infection and subsequent disease progression in humans.

EXAMPLES

The present invention is illustrated by the following examples. It is to be understood that the particular examples, materials, amounts, and procedures are to be interpreted broadly in accordance with the scope and spirit of the invention as set forth herein.

Example I

Vaccination with Trypomastigote Surface Antigen-1-encoding Plasmid DNA Confers Protection Against Lethal *Trypanosoma cruzi* Infection Mice and parasites. Six- to 8-wk-old female C57BL/6J (B6) and BALB/cByJ (BALB/c) mice (breeding pairs obtained from The Jackson Laboratory (Bar Harbor, Me.) were used in all experiments. The Brazil strain of *T. cruzi* was maintained in vivo by serial biweekly passage of $10^3$ bloodform trypomastigotes (BFT) in C3H/HeSnJ mice and by continuous in vitro passages of tissue culture-derived trypomastigotes (TCT) in monolayers of Vero cells. B6 mice were infected intraperitoneally with $10^3$ BFT and challenged 3 months later challenged with $10^5$ TCT by subcutaneous injection at the base of the tail.

Cell lines and culture reagents. P815 ($H-2^d$; mastocytoma cells; ATCC TIB 64), J774 ($H-2^d$, macrophages, ATCC TIB 67), 3T3 ($H-2^d$, fibroblasts, ATCC CCL 163), Vero (African Green monkey kidney cells, ATCC CCL 81) (all from American Type Culture Collection [ATCC], Rockville, Md.), RMA-S (peptide TAP.2 transporter-deficient, low $H-2^b$ expressor mutant of the RBL-5 Rauscher virus-induced T cell lymphoma; provided by Dr. H.-G. Ljundggren, Karolinska Institute, Stockholm, Sweden) and 5A.Kb. 3 cells ($H-2^k$ fibroblasts stably transfected with the $K^b$ gene; provided by Dr. S. Jameson, University of Minnesota, Minneapolis, Minn.) were maintained in complete RPMI-1640 (Mediatech, Herndon, Va.) medium (CR) containing 10% heat-inactivated fetal bovine serum (HyClone, Logan, Utah), 20 mM HEPES, 2 mM L-glutamine, 1 mM sodium pyruvate, 0.1 mM nonessential amino acids and 50 µg/ml gentamicin (all from Gibco BRL, Gaithersburg, Md.). COS-7 cells (SV40 transformed African Green monkey kidney cells; ATCC CRL 1651) were grown in similarly supplemented Dulbecco's modified Eagle's medium (Mediatech, Herndon, Va.). T cell medium (TCM) was prepared by supplementing CR with 50 µM 2-mercaptoethanol (Gibco BRL).

Peptides. The peptide TSA-$1_{515-522}$ (VDYNFTIV; SEQ ID NO:1), representing the $H-2K^b$-restricted *T. cruzi* Trypomastigote Surface Antigen-1 CTL epitope was produced using Fmoc-based solid phase chemistry on an ACT MPS 350 peptide synthesizer (Advanced Chem Tech, Louisville, Ky.) by Molecular and Genetic Instrumentation Facility at University of Georgia (Athens, Ga.). The H-2 $K^b$-restricted OVA CTL peptide OVA$_{257-264}$ (SIINFEKL; SEQ ID NO:2) was used as a control. Lyophilized peptides were dissolved at 20 mg/ml in DMSO and stored at −70° C. Before use, peptides were diluted with RPMI-1640. Peptides were not toxic to target cells or effector cell cultures.

Plasmid DNA constructs. The genomic DNA fragments of the TSA-1 gene (D. Fouts et al., *Mol Biochem Parasitol.* 46:189-200 (1991); D. Peterson et al., *Nature* 322:566-8 (1986)) encoding amino acid residues 78 to 652 and 78 to 790, excluding and including, respectively, the 5 nonapeptide tandem repeat unit, were amplified by PCR using pBluescript II SK (+)/TSA-1 (provided by Dr. David Fouts, University of California, Irvine, Calif.) as a template. Forward and reverse primers were designed to incorporate, respectively, SalI and XbaI restriction sites (underlined below) for directional cloning. Primers were constructed on an Applied Biosystems 394 DNA/RNA synthesizer (Foster City, Calif.) at the Molecular Genetics Instrumentation Facility. The forward oligonucleotide primer 5'-AGTCGACGGATCCATGATTGCATTTGTCGAAGGC-3' (SEQ ID NO:3) was used with reverse primers 5'-ATCTAGAAGCTTCATAGTTCACCGACACTCAGTGG-3' (SEQ ID NO:4) and 5'-ATCTAGAAGCTTCATGCCGCAGCATTTGCTTCCCC-3' (SEQ ID NO:5), to amplify a 1.7 kb (repeatless TSA-$1_{78-652}$) and a 2.1 kb (repeat-bearing TSA-$1_{78-790}$) product, respectively. The amplification products containing the A overhangs generated by Taq DNA polymerase during the PCR reaction were cloned into the HindIII site of pUC19-T vector. Following digestion with SalI and XbaI, the 1.7 kb and 2.1 kb TSA-1 fragments were gel purified and cloned into the SalI and XbaI sites of the eukaryotic expression vector VR1012 (Vical Inc., San Diego, Calif.) G. Hartikka et al., *Hum. Gene Ther.* 7:1205-1217 (1996)) to generate VR1012 TSA1.7 and VR1012 TSA2.1. In the VR1012 vector, expression of the encoded gene is driven by a CMV immediate-early gene promoter. Constructs were transformed into *Escherichia coli* DH5-competent cells and grown in Luria Bertani broth with 70 µg/ml kanamycin. Closed circular plasmid DNA was purified by anion exchange chromatography using the Qiagen maxi prep kit (Qiagen, Chatsworth, Calif.) according to manufacturer's specifications. Plasmid DNA was sterilized by ethanol precipitation and dissolved in sterile phosphate-buffered saline (PBS).

In vitro expression. Expression of the VR1012 TSA1.7 and VR1012 TSA2.1 in COS-7 cells was assessed in vitro by transient transfection. COS-7 cells were seeded in 6-well plates (Costar, Cambridge, Mass.) at $2 \times 10^5$ cells/well in 3 ml complete DMEM and incubated overnight at 37° C., 6% $CO_2$. In a final volume of 300 µl, 10 µg of plasmid DNA (unmodified VR1012 plasmid, TSA-1-encoding VR1012 TSA1.7 or VR1012 TSA2.1) were mixed with 30 µg of Lipofectin Reagent (Gibco BRL), and the mixture incubated for 15 minutes at room temperature before being diluted with 1.7 ml serum-free MEM. After washing COS-7 monolayers (50-70% confluent) with serum-free MEM, cells were overlayed with the mixture containing the DNA-Lipofectin complexes and incubated overnight at 37° C., 6% $CO_2$. Cell culture media was then replaced with 3 ml complete DMEM and incubated for an additional day. Transiently transfected COS-7 cells were harvested by gentle trypsinization, washed in PBS, and seeded in 8-well Lab Tek chamber slides (Nunc Inc., Naperville, Ill.) at $1 \times 10^4$ cells/well. After overnight incubation at 37° C., 6% $CO_2$, cells were washed with PBS, fixed in ice cold methanol for 15 minutes at 4° C. and washed 4 more times before blocking with PBS-1% bovine serum albumin (BSA) for 1 hour at 37° C. Cells were subsequently stained for 2 hours at 37° C. with a polyclonal anti-*T. cruzi* serum obtained from acutely infected C3H/HeSnJ mice or with normal mouse serum (1:200 dilution in PBS-1% BSA), washed 3 times, and finally incubated for 1 hour at room temperature with fluorescence isothiocyanate (FITC)-labeled F(ab')$_2$ goat anti-mouse IgG (1:50 dilution in PBS-1% BSA) (Southern Biotechnology, Birmingham, Ala.). Slides were then rinsed 4 times with PBS-1% BSA and mounted in 10% glycerol, 0.1 M sodium bicarbonate (pH 9), 2.5% 1,4-diazobicyclo-(2,2,2) octane for visualization by laser scanning confocal microscopy (MRC-600) (Bio-Rad Laboratories, Hercules, Calif.).

Genetic immunizations and challenges. Groups of B6 and BALB/c mice were injected intramuscularly into each tibialis anterior muscle with 50 µg of VR1012 TSA1.7, VR1012 TSA2.1 or control VR1012 suspended in 50 µl PBS using a 27-gauge needle. Mice were boosted 4 weeks later with an identical dose of plasmid (100 µg total) given by the same bilateral intramuscular injection. Tail blood samples were collected 3 and 2 weeks after the first and second dose, respectively, and sera stored at $-20°$ C. until assayed for anti-$T.$ $cruzi$ antibody. Two weeks after the second dose, animals were infected by intraperitoneal injection of $10^5$ (B6) or $10^3$ (BALB/c) $T.$ $cruzi$ BFT. Parasitemias were monitored periodically using hemacytometer counts of 10 µl tail-vein blood in an ammonium chloride solution. Mortality was recorded daily.

Determination of serum antibody levels. Antibody responses induced by the immunization of mice with plasmid DNA was evaluated by a solid-phase enzyme-linked Immunosorbant assay (ELISA). In brief, capture antigen was prepared by sonication of PBS-washed $5 \times 10^7$ $T.$ $cruzi$ parasites (80% trypomastigotes; 20% amastigotes) in 50 mM carbonate-bicarbonate buffer (pH 9.6). Sonicated material was spun for 1 hour at $100,000 \times g$ at $4°$ C. Wells of flexible polyvinyl chloride 96-well plates (Falcon, Becton Dickinson & Co., Oxnard, Calif.) were coated overnight at $4°$ C. with 100 µl of a predetermined optimal dilution ($5 \times 10^5$ parasites/well) of the soluble antigen. Washed wells were blocked with 1% BSA in PBS-0.05% Tween 20 (PBST) for 1 hour at $37°$ C. After blocking, 100 µl of pooled mouse sera (1:100 dilution in PBST) was added to the plates and incubated for 1 hour at $37°$ C. Plates were washed 6 times with PBST and incubated for an additional hour with 100 µl of a horseradish peroxidase-labeled goat anti-mouse immunoglobulin (A, G, M) (1:1000 dilution in PBST) (Cappel, Organon Teknika Corp., West Chester, Pa.). Washed wells were developed with 100 µl of the substrate 2,2'-azino-bis-(3-ethyl-benzthiazoline-6-sulfonic acid) and absorbance read at 405 nm using an automated ELISA microplate reader (Bio-Tek Instruments, Winooski, Vt.).

Generation of effector cells. Unless otherwise indicated, spleens from DNA-immunized mice were removed two weeks after the last dose and immune spleen cell (SC) suspensions prepared in TCM. In the case of B6 mice, spleen cells (SC) were cultured in 24-well plates at $5 \times 10^6$ cells/well. TSA-$1_{515-522}$ peptide was included in each 2-ml culture at 1 µM final concentration. In the case of BALB/c mice, $35 \times 10^6$ SC in 10 ml TCM were cultured in upright 25-cm$^2$ tissue culture flasks containing irradiated monolayers of stimulator $T.$ $cruzi$-infected J774 cells. After 2 days of incubation at $37°$ C., 6% $CO_2$, cultures were made to 5% Rat T-STIM without Con A (Collaborative Biomedical Products, Bedford, Mass.) and incubated for 4 additional days. Effector cells from BALB/c mice were also unstimulated immune SC without undergoing secondary in vitro stimulation. SC from B6 mice chronically infected with $T.$ $cruzi$ were obtained 6 months after parasite challenge and stimulated as described for SC from DNA-immunized animals.

Preparation of Peptide-Pulsed Target Cells. Peptide-Pulsed Targets were used to measure CTL activity of peptide-stimulated effector cells generated from plasmid DNA-immunized B6 mice. RMA-S(H-$2^b$) cells preincubated for 24 h at $26°$ C., 6% $CO_2$, were seeded into 24-well plates (Costar, Cambridge, Mass.) at $10^6$ cells/well in 2 ml CR and incubated overnight under the same conditions in the presence of 0.05 µm of TSA-$1_{515-522}$ peptide or OVA$_{257-264}$ negative control peptide and 100 µCi of a sterile Na$_2^{51}$CrO$_4$ solution ($^{51}$Cr) (Amersham Life Science Corporation, Arlington Heights, Ill.). Two hours prior to their processing for CTL assays, cells were shifted $37°$ C., 6% $CO_2$. P815 (H-$2^d$) target cells were also prepared in 24-well plates by overnight incubation at $37°$ C., 6% $CO_2$, with $^{51}$Cr and TSA-$1_{515-522}$ peptide.

Preparation of $T.$ $cruzi$-infected stimulator and target cells. $T.$ $cruzi$-infected cells were used to generate and measure the CTL activity of effector cells from plasmid DNA-immunized BALB/c mice. Monolayers of J774 cells (60% confluent) prepared in upright 25-cm$^2$ tissue culture flasks (Corning, N.Y.) were infected overnight with $T.$ $cruzi$ TCT (50:1 parasite to host cell ratio). After extensive washing with serum-free RPMI 1640 to remove noninvading parasites, infected monolayers were irradiated (14 Krad) (Gammacell 200, $^{60}$Co source) and then used as stimulators for immune SC. To prepare $T.$ $cruzi$-infected target cells used to ascertain the lytic activity of BALB/c-derived stimulated SC, monolayers (50% confluent in horizontal 25-cm$^2$ flasks) of MHC-matched 3T3 (H-$2^d$) and mismatched 5A.Kb. 3 (H-$2^k$ and H-$2K^b$) cells were incubated for 2 days at $37°$ C., 6% $CO_2$, in CR supplemented with 1000 U/ml of IFN-+β (Lee Biomolecular Laboratories, Inc., San Diego, Calif.), washed and then infected overnight with $T.$ $cruzi$ TCT (50:1 parasite to host cell ratio). After washing, $T.$ $cruzi$-infected monolayers were treated with PBS-1 mM EDTA to prepare single cell suspensions and washed once more before a 1-h $^{51}$Cr-labeling step at $37°$ C. To assess the lytic activity of unstimulated BALB/c-derived immune SC, monolayers of untreated J774 cells were infected and single cell suspensions for $^{51}$Cr labeling were prepared by moderate pipetting of the cell monolayer. Under the conditions described, stained (Leukostat, Fisher Scientific, Atlanta, Ga.) cytospin preparations of each culture indicated that 65-75% of the cells were infected.

CTL assay. Cytolytic activity was measured by the $^{51}$Cr release assay, as described in Wizel et al. ($Eur.$ $J.$ $Immunol.$ 24:1487-95 (1994)). In brief, $^{51}$Cr-labeled target cells were washed three times in CR and resuspended in TCM, and $5 \times 10^3$ targets (100 µl) were added to effector cells (100 µl) at various effector-cell-to-target-cell (E:T) ratios in 96-well round-bottom plates (Corning). After a 5 hour incubation at $37°$ C., 6% $CO_2$, supernatants were harvested with the Skatron SCS System (Skatron, Sterling, Va.) and radioactivity counted on a Cobra II Autogamma counter (Packard Instrument Company, Downers Grove, Ill.). Percent-specific lysis was calculated from the mean of triplicates as follows: 100× [(experimental release–spontaneous release)/(maximum release–spontaneous release)]. Maximum and spontaneous release were determined in wells containing no effectors in the presence or absence of 2% Triton X-100, respectively. In experiments where CTL activity of CD8$^+$ and CD4$^+$ T cells was tested, effector cells were depleted by incubation on ice for 30 minutes with predetermined dilutions of culture supernatants from hybridomas 3.155 (anti-CD8) (ATCC TIB 211), and RL172 (anti-CD4), followed by 30 minutes at $37°$ C. in the presence of 1:6 diluted rabbit complement (Pel-Freez, Brown Deer, Wis.). Spontaneous release did not exceed 20% of the maximum release. SE ranged between 0.02 to 6.1% of the mean.

Results

Expression of TSA-1 in transiently transfected cells. To study the effectiveness of genetic immunization against $T.$ $cruzi$, the TSA-1 gene was subcloned into the VR1012 mammalian expression vector containing the CMV promoter and the bovine growth hormone polyadenylation sequences. The constructs VR1012 TSA1.7 and VR1012 TSA2.1 were generated to drive the expression of two N-terminally truncated TSA-1 gene products lacking and bearing, respectively, the 5 nonapeptide repeats located near the C-terminal end of the TSA-1 protein. Both plasmid constructs expressed the inserted TSA-1 gene fragment upon transient transfection of COS-7 cells. The cytoplasmic expression of TSA-1 in VR1012 TSA1.7- and VR1012 TSA2.1-transfected cells was intense as detected by immunofluorescent staining with a polyclonal anti-*T cruzi* serum. In contrast, similarly transfected cells stained with normal mouse serum showed no evidence of immunofluorescence. No expression was detected in cells transfected with the unmodified VR1012 vector and stained with either sera.

Immunization with TSA-1 plasmid DNA elicits parasite-specific antibody response. A strong humoral immune response has been widely implicated as a major effector mechanism that participates in the immune control of *T. cruzi* and immunization of mice with a recombinant N-proximal portion of TSA-1 induces an antibody response which correlates with survival to a lethal challenge infection. To ascertain whether a *T. cruzi*-specific antibody response could be elicited by the expression of the TSA-1 protein fragments following intramuscular DNA immunization, BALB/c and B6 mice were injected with 100 μg VR1012 TSA1.7, VR1012 TSA2.1 or unmodified VR1012 control plasmid (50 μg of split in each tibialis anterior muscle). Mice were boosted after 4 weeks with the same dose of plasmid. The presence of parasite-specific antibodies in pooled sera prepared from each group of mice was assessed by ELISA (FIG. 1). Three weeks following the first dose, sera from BALB/c mice immunized with either VR1012 TSA1.7 or VR1012 TSA2.1 showed comparable antibody responses against the sonicated parasite material used as capture antigen. Two weeks after the second dose, while a boosting in the parasite-specific antibody level was detected in the sera from VR1012 TSA1.7-immunized group, the level of antibodies in the sera from the VR1012 TSA2.1-immunized animals remained essentially unchanged. When a similar analysis was conducted for the pooled sera from similarly immunized B6 mice, the antibody levels after the first dose did not exceed the level found in normal mouse serum. However, after the second dose, only the VR1012 TSA2.1-immunized group showed a parasite-specific antibody response. In all cases, the antibody levels detected in the sera from groups of mice immunized with unmodified VR1012 vector was no different than the level measured in normal mouse serum.

Induction of long-lasting TSA-1-specific CTL response in TSA-1 plasmid DNA-immunized B6 mice. TSA-$1_{515-522}$ is a target of H-2 $K^b$-restricted protective CTL responses induced in B6 mice infected with *T. cruzi*. We therefore wanted to determine whether immunization of this strain of mice with the TSA-1-encoding DNA vectors could induce a TSA-$1_{515-522}$-specific CTL response. Two weeks after the second intramuscular injection of either VR1012 TSA1.7 or VR1012 TSA2.1, immune Sc were stimulated with TSA-$1_{515-522}$ (1 μM). After 6 days, recall CTL activity of undepleted responder cultures was assessed in a 5 hour $^{51}$Cr release assay against RMA-S(H-$2^b$) and P815 (H-$2^d$) target cells sensitized with TSA-$1_{515-522}$ peptide (0.05 μM) at the indicated E:T ratios. RMA-S cells pulsed with $OVA_{257-264}$ peptide (0.05 μM) were used as negative control target cells. CTL activity of effector cells depleted of $CD4^+$ or $CD8^+$ T cells was measured at a 50:1 E:T ratio against TSA-$1_{515-522}$-sensitized (0.05 μM) target cells. CTL activity was antigen specific, MHC class I-restricted and dependent on $CD8^+$ T lymphocytes (FIG. 2A). The H-$2^b$ effector cells lysed matched RMA-S cells (H-$2^b$) sensitized with TSA-$1_{515-522}$ but were unable to lyse the same cells pulsed with control peptide $OVA_{257-264}$ or MHC-mismatched P815 cells (H-$2^d$) pulsed with TSA-$1_{515-522}$.

Detected lytic activity was abrogated by $CD8^+$ T cell depletion, but not by depletion of $CD4^+$ effectors. In no case did TSA-$1_{515-522}$-stimulated SC from mice immunized with unmodified VR1012 vector display CTL activity against peptide-sensitized target cells. Similar TSA-$1_{515-522}$-specific CTL activity was detected in the peptide-stimulated SC cultures established 7 mo after mice had received the second 100 μg dose of the TSA-1-encoding DNA vectors (FIG. 2B). The magnitude of such recall CTL response was comparable to the CTL activity detected for TSA-$1_{515-522}$-stimulated effectors from *T. cruzi*-infected mice. Hence, immunization of B6 mice with both TSA-1-encoding DNA constructs generates a long-lasting TSA-$1_{515-522}$-specific CTL response which closely resembles the recall response induced in *T. cruzi*-infected animals.

CTL response induced in BALB/c mice by TSA-1 plasmid DNA immunization is parasite-specific, MHC class I-restricted and $CD8^+$ T cell-dependent. Despite the fact that the target antigens recognized by CTL from *T. cruzi*-infected BALB/c mice (H-$2^d$) have not been identified, SC from these animals display genetically restricted CTL activity against *T. cruzi*-infected target cells. Thus, we used this system to determine whether parasite-specific CTLs could be induced in BALB/c mice following immunization with the TSA-1-encoding plasmid DNA constructs. Two weeks after the second vaccination, immune SC from BALB/c (H-$2^d$) mice were prepared and tested unstimulated for CTL recognition of *T. cruzi*-infected or uninfected J774 macrophages (H-$2^d$) and *T. cruzi-infected* 5A.Kb. 3 fibroblasts (H-$2^k$; H-$2K^b$) in a 5-h $^{51}$Cr release assay at the indicated E:T ratios (FIG. 3A). Following a 6-day stimulation period with irradiated *T. cruzi*-infected J774 macrophages, effector cells were assayed at the indicated E:T ratios for CTL activity on $^{51}$Cr labeled *T. cruzi*-infected or uninfected 3T3 fibroblasts (H-$2^d$) and *T. cruzi-infected* 5A.Kb. 3 cells. Effector cells depleted of $CD4^+$ or $CD8^+$ T cells were tested for CTL activity at a 50:1 E:T ratio against *T. cruzi-infected* 3T3 cells. Levels of infection in stimulator cells and target cells ranged from 65 to 75%. Infection of J774 cells (H-$2^d$) with *T. cruzi* efficiently targeted these macrophages for lysis by the H-$2^d$ effector cells harvested from either VR1012 TSA1.7- or VR1012 TSA2.1-immunized mice. In contrast, minimal or no lysis was detected against uninfected J774 cells and against mismatched *T. cruzi*-infected 5A.Kb. 3 fibroblasts (H-$2^k$; H-$2K^b$). None of the target cells tested was recognized by effector cells obtained from control VR1012-immunized animals. Then, CTL activity of immune SC that had been stimulated for 6 days with *T. cruzi*-infected J774 macrophages was assessed against uninfected and *T. cruzi*-infected fibroblasts (FIG. 3B). Again, the specificity and MHC class I-restricted nature of the recall CTL response was demonstrated by the ability of effector cells derived from VR1012 TSA1.7- and VR1012 TSA2.1-immunized mice to lyse infected but not uninfected 3T3 cells (H-$2^d$) and by their inability to recognize infected 5A.Kb. 3 cells (H-$2^k$; H-2 $K^b$). When the phenotype of the VR1012 TSA1.7-derived effectors was tested, it was found that they were $CD8^+CD4^-$ because the lytic activity of these cells was significantly reduced by the depletion of $CD8^+$ T cells and minimally affected by the depletion of $CD4^+$ T cells. Similarly stimulated VR1012 immune SC failed to lyse all the target cells tested. Altogether, these data indicated that immunization of BALB/c mice with TSA-1-encoding DNA plasmids efficiently primed parasite-specific CD8+ CTL precursors and that these in vivo expanded cells were in sufficient numbers that allowed the detection of their genetically-restricted lytic activity without in vitro restimulation.

Figure 4A:
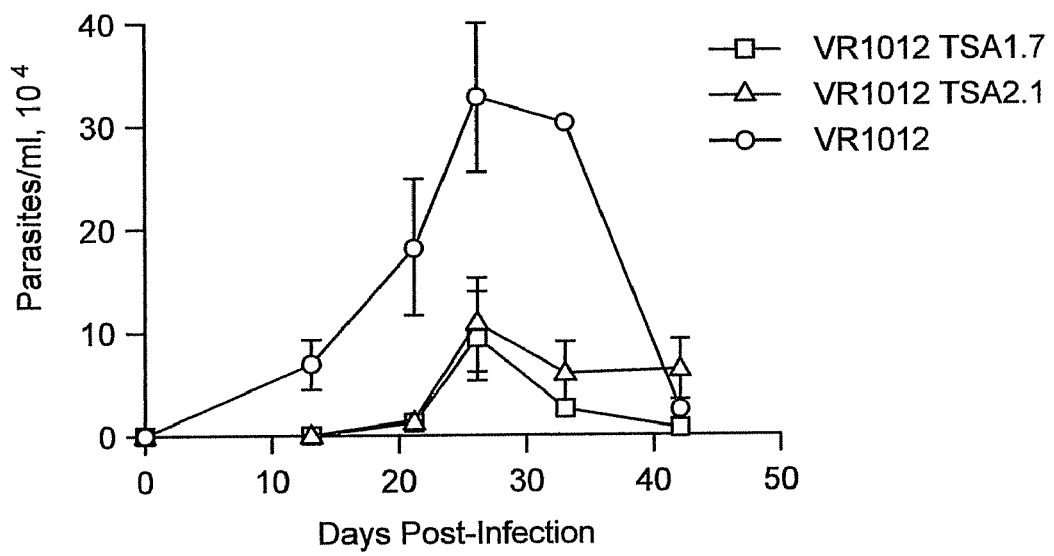
FIG. 4 shows (A) parasitemia and (B) mortality in TSA-1 plasmid DNA vaccinated B6 mice. Values represent mean±SEM in surviving mice.
Figure 4B:
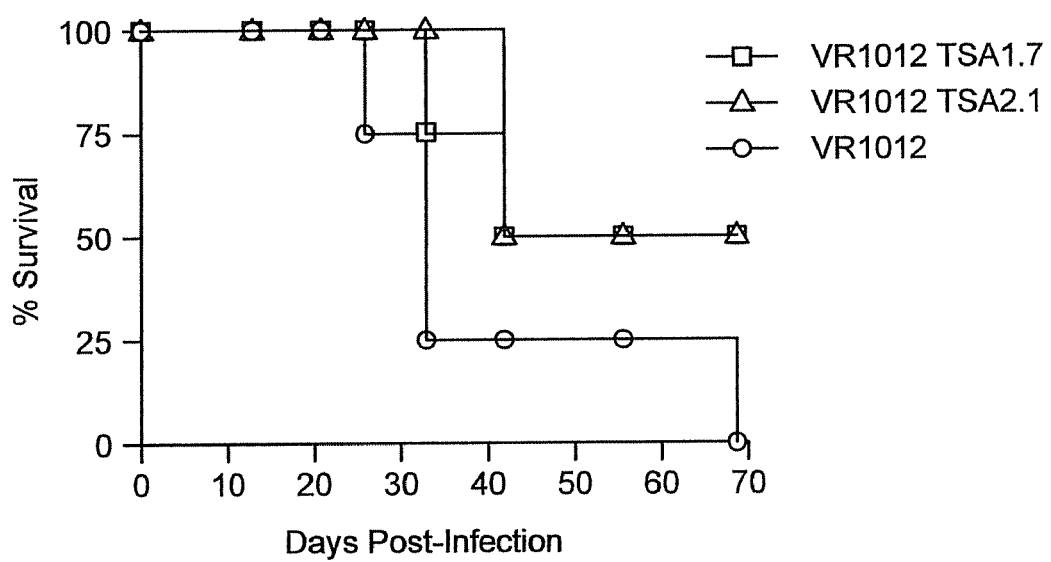
Figure 5A:
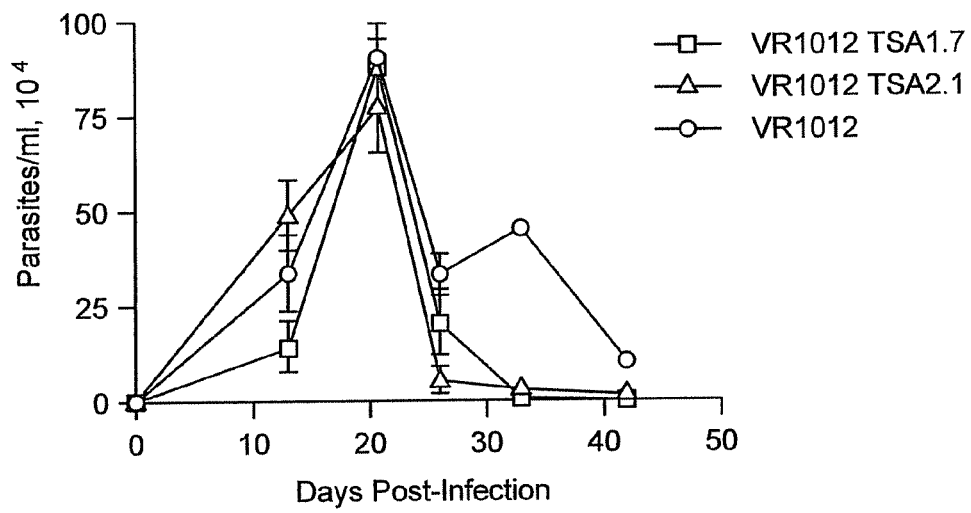
FIG. 5 shows (A) parasitemia and (B) mortality in TSA-1 plasmid DNA vaccinated BALB/c mice.
Figure 5B:
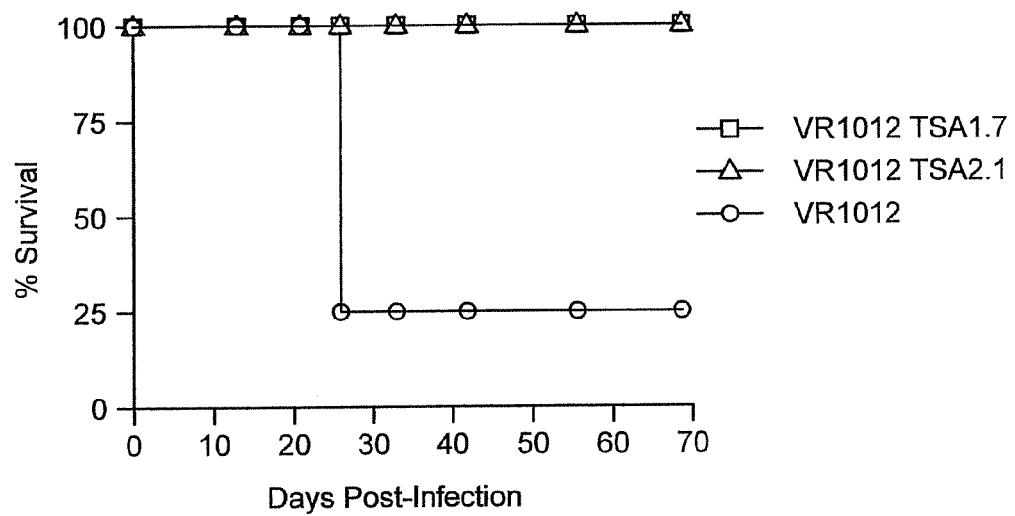

TSA-1 plasmid DNA-based vaccine significantly protects mice from *T. cruzi*-induced mortality. Having established that B6 and BALB/c mice generated *T. cruzi*-specific immune responses upon immunization with either of the TSA-1-expressing constructs, we next determined whether DNA vaccination could provide these animals with any degree of protection against challenge with *T. cruzi*. Two weeks after the second immunizing dose, groups of B6 and BALB/c mice were challenged with $10^5$ or $10^3$ *T. cruzi* BFT, respectively. The differences in the challenging dose was to compensate for the observed differences in susceptibility of each strain of mice. Both strains of mice showed a significant degree of protection against *T. cruzi*-induced mortality. As illustrated in one of 3 conducted experiments, B6 mice vaccinated with either of the TSA-1-encoding vectors showed a 7-day delay in the onset of parasitemia and a consistently reduced level of parasites compared to control animals immunized with the unmodified VR1012 vector (FIG. 4A). Moreover, all control animals died before 45 days post-infection, whereas 50% of mice in each of the test groups survived the infection (FIG. 4B). In the case of BALB/c mice, however, the steady increase in parasitemia noted in TSA-1 DNA vaccinated animals was strikingly similar to the kinetics of infection observed for mice immunized with the unmodified plasmid DNA (FIG. 5A). Despite similar levels of circulating parasites in test and control animals, none of the mice vaccinated with either of the TSA-1-encoding vectors succumbed to *T. cruzi* infection whereas 75% of control mice developed fatal infections within 27 days post-infection (FIG. 5B). Overall, protection against and otherwise lethal innoculum with trypomastigotes was observed in 73% and 55% of VR1012 TSA1.7- and VR1012 TSA2.1-vaccinated B6 mice, respectively, and in 91% and 86% of similarly vaccinated BALB/c mice (Table 1). In contrast, control VR1012-vaccinated remained highly susceptible to *T. cruzi-induced* lethality as only 9% overall survival was observed for both strains (Table 1).

TABLE 1

Protection against lethal *T. cruzi* challenge conferred by DNA vaccination

| Plasmid DNA | B6 mice | | BALB/c mice | |
|---|---|---|---|---|
| | Survivors/Challenged | Percent survival | Survivors/Challenged | Percent survival |
| VR1012 | 0/3 | | 0/3 | |
| | 0/4 | | 1/4 | |
| | 1/4 | | 0/4 | |
| Total VR1012 | 1/11 | 9 | 1/11 | 9 |
| VR1012 TSA1.7 | 3/3 | | 3/3 | |
| | 2/4 | | 4/4 | |
| | 3/4 | | 3/4 | |
| Total VR1012 TSA2.1 | 8/11 | 73 | 10/11 | 91 |
| | 2/3 | | 2/3 | |
| | 2/4 | | 4/4 | |
| | 2/4 | | nd | |
| Total | 6/11 | 55 | 6/7 | 86 | nd: not determined

Discussion

Thus far, the exploration of vaccines against *T. cruzi* has been widely avoided due to the fear that such intervention methods would exacerbate rather than prevent a disease that many still consider to have an autoimmune etiology. However, we believe that *T. cruzi* persists in the diseased tissue, and that it is the persistence of the parasite and not the parasite-induced immune responses to self molecules which correlates best with the induction and maintenance of the inflammatory disease process. This link between parasite load and severity of disease is further supported by the very important role that CD8+ T cells play in parasite control and survival to infection. CD8+ T cells constitute the major component in inflammatory foci of *T. cruzi*-infected tissues and, in their absence, infected mice have increased mortality rates and tissue parasite loads with a decreased or absent inflammatory response. The recent demonstration of CD8+CTL in *T. cruzi*-infected mice and humans with a specificity for defined trypomastigote and amastigote surface molecules and of the immunoprotective phenotype that these cells express prompted us to initiate the development of immunization strategies to further characterize the vaccine potential of parasite components known to be targets of protective anti-*T. cruzi* immune responses.

DNA-based immunization has been shown in animal models to easily, safely and effectively elicit and modulate the spectrum of immune responses necessary for the prevention of infectious diseases (S. Gurunathan et al., *J. Exp. Med.* 186:1137-1147 (1997); D. Lowrie et al., *Vaccine* 15:834-838 (1997): M. Sedegah et al., *Proc. Nat'l Acad. Sci. U.S.A.* 91:9866-70 (1994); J. Ulmer et al., *Science* 259:1745-1749 (1993); Z. Xiang et al., *Virology* 199:132-140 (1994); M. Yokoyama et al., *J. Virol.* 69:2684-2688 (1995)) and for the treatment of neoplastic (R. Corny et al., *Semin Oncol.* 23:135-147 (1996); K. Irvine et al., *J. Immunol.* 156:238-245 (1996)); R. Schirmbeck et al., *J. Immunol.* 157:3550-3558 (1996)), allergic ENRfu (C. Hsu et al., *Nat. Med.* 2:540-544 (1996); E. Raz et al., *Proc. Nat'l. Acad. Sci. USA.* 93:5141-45 (1996)) and autoimmune disorders (A. Waisman et al., *Nat. Med.* 2:899-905 (1996)). Thus, we chose this vaccination method to induce *T. cruzi*-specific antibody and class I-restricted CD8+CTL responses in two inbred mouse strains and to assess its protective efficacy against parasite challenge. Our recent demonstration of TSA-1 as a target of protective CTL made this parasite molecule a prime model antigen to evaluate this immunization method inasmuch as the N-proximal portion of TSA-1 had already been shown to induce antibody responses which correlate with survival to lethal *T. cruzi* infection and TSA-1 is a member of the large 85-kDa family of trypomastigote surface proteins which are recognized by human sera and rodent-derived protective antibodies.

Plasmid DNA vaccines VR1012 TSA1.7 and VR1012 TSA2.1 were constructed to drive the expression of products TSA-1$_{78-652}$ and TSA-1$_{78-790}$ truncated at the N-terminus by 77 residues and at the C-terminus by 183 and 45 amino acids, respectively. The main reasons for such a design were twofold: first, because removal of the N-terminal endoplasmic reticulum translocation signal sequence would ensure the cytoplasmic retention of de novo synthesized TSA-1 protein, their subsequent cytosolic degradation and an efficient priming of CTL responses; second, because conventional TSA-1 protein-based immunization of BALB/c mice has shown that the C-proximal portion encompassing residues 618 to 835 contains epitopes which interfere with the generation of antibodies to the protective determinants within residues 78 to 619 of the N-proximal portion.

Both VR1012 TSA-1 constructs directed the in vitro expression of cytoplasmically-retained products with immunoreactivity to sera from *T. cruzi*-infected mice and in BALB/c mice, both TSA-1-encoding vectors, with and without repeat sequence, elicited parasite-specific antibody responses. Such responses were detected after the priming dose, and a modest boosting was achieved after the second dose with the VR1012 TSA2.1 vector. In B6 mice, parasite-specific antibodies were detected only after the second dose of the VR1012 TSA2.1 vector alone.

The fact that immunization with TSA-1-expressing plasmid DNA vaccines efficiently elicited MHC class I-restricted CTL responses in B6 (H-2$^b$) and BALB/c (H-2$^d$) mice is notable, inasmuch as prior to these studies *T. cruzi*-specific CD8$^+$CTL had only been primed by parasite infection and TSA-1 had only been identified as a CTL target molecule of B6 mice. The demonstration in B6 mice that TSA-1 DNA vaccination and *T. cruzi* infection were able to prime CD8$^+$ CTL populations with specificity for the same protective H-2K$^b$-restricted TSA-1$_{515-522}$ epitope indicated that similar immunogenic peptides are generated when a cell is transiently transfected in vivo or when it is expressed by an infected cell. In agreement with other studies where DNA immunization has been found to elicit long-lasting CTL responses, TSA-1$_{515-522}$-specific CTL were still detected 7 months after administering the last dose of the TSA-1-encoding DNA. The longevity of the response may be explained by the persistence of the plasmid vaccine in vivo, or to recent reports which indicate that CTL memory does not require antigen persistence or CD4 T cell help. Regardless of the mechanisms involved, the ability of genetic immunization to maintain a long-lasting response to protective *T. cruzi* CTL epitopes may have significant potential for the development of DNA vaccines capable of preventing or treating an established *T. cruzi* infection.

While the presence of class I-restricted CTL to *T. cruzi*-infected cells has been demonstrated in BALB/c mice, the identification of their target antigens has not been. Hence, in the absence of known TSA-1-derived H-2$^d$-restricted CTL peptide epitopes, two alternative strategies were used to determine that TSA-1-expressing DNA vaccines had successfully primed parasite antigen specific CTL responses. In the first strategy where the CTL assay was performed on immune SC without in vitro stimulation significant genetically restricted CTL reactivity was detected against *T. cruzi*-infected target cells. These results suggest the priming of a substantial number of TSA-1-specific CTL precursors of which a large population remain in a state of activation that allows for their direct detection two weeks after the last dose of the DNA vaccine. Similar findings on the detection of CTL activity using unstimulated SC from mice immunized with DNA vaccines have been reported for the Vif and Nef proteins of HIV-1 and for the SV40 T antigen. In the second strategy, the stimulating and targeting activities of *T. cruzi*-infected cells were used to confirm the specificity and MHC class I-restricted lytic activity displayed by in vitro expanded CTL precursors. These findings and the fact that the lytic activity was CD8$^+$ T cell-dependent indicate that the observed response was T cell- and not NK cell-mediated and attest to the value of this method of immunization for priming potent MHC class I-restricted CTL responses in vivo.

Perhaps the most significant finding of these studies was that vaccination with TSA-1-expressing plasmid DNA afforded B6 and BALB/c mice significant levels of protection against lethal *T. cruzi* challenge infection. Overall survival rates in B6 mice vaccinated with VR1012 TSA1.7 or VR1012 TSA2.1 were 73 and 55%, respectively. The same constructs furnished BALB/c mice with nearly complete protection as 91 and 86% of vaccinated animals survived *T. cruzi* infection. These results are in sharp contrast to the 9% survival observed in animals immunized with the unmodified VR1012 plasmid for both strains of mice. It should be noted, though, that immunization with the TSA-1-encoding vectors did not prevent recipient mice from getting infected, and DNA-vaccinated mice from both strains developed parasitemias, albeit at different levels. In B6 mice, the number of circulating parasites in test animals was lower than that observed for recipients of the control DNA vaccine, whereas in BALB/c mice, parasitemias were frequently similar in both groups of animals.

Example II

Genetic Immunization Elicits Antigen-Specific Protective Immune Responses and Decreases Disease Severity in *Trypanosoma Cruzi* Infection Mice and parasites. Six- to 8 week old female C57BL/6J ("B6") (Jackson Laboratory, Bar Harbor, Me.) were used in all experiments. The Brazil strain of *T. cruzi* was maintained in vivo by serial biweekly passage of 10$^3$ blood-form trypomastigotes (BFT) in C3H/HeSnJ mice and by continuous in vitro passages of tissue culture-derived trypomastigotes in monolayers of Vero cells, according to standard parasitology techniques.

Cell lines and culture reagents. Vero (African Green monkey kidney cells, ATCC CCL 81, Rockville, Md.) and RMA-S cells (an immuno-selected variant of the RBL-5 lymphoma that is deficient in the expression of class I MHC molecules due to a mutation in the TAP-2 peptide transporter, a gift from Dr. M. B. Oldstone, Scripps Research Institute, La Jolla, Calif.) were maintained in complete RPMI-1640 medium (Mediatech, Herndon, Va.) containing 10% heat-inactivated fetal bovine serum (HyClone, Logan, Utah), 20 mM HEPES, 2 mM L-glutamine, 1 mM sodium pyruvate, and 50 µg/ml gentamicin (all from Gibco BRL, Gaithersburg, Md.). COS7 cells (SV40 transformed African Green monkey kidney cells; ATCC CRL 1651) were grown in similarly supplemented Dulbecco's modified Eagle's medium (DMEM) (Mediatech, Herndon, Va.). T cell medium (TCM) was prepared by supplementing RPMI-10% FBS with 50 µM 2-mercaptoethanol and 0.1 mM non-essential amino acids (Gibco BRL).

Peptides. Peptides were synthesized using Fmoc-based solid phase chemistry on an ACT MPS 350 peptide synthesizer (Advanced Chem Tech, Louisville, Ky.) by the Molecular and Genetic Instrumentation Facility (MGIF) at the University of Georgia. The synthetic peptides pep77.2 (TSA-1$_{515-522}$; VDYNFTIV (SEQ ID NO:6)) (B. Wizel et al., *J. Immunol.* 159:6120-30 (1997); M. Santos et al., *Mol. Biochem. Parasitol.* 86:1-11 (1997)), PA8 (ASP-2$_{552-559}$; VNHRFTLV (SEQ ID NO:7)) and PA14 (ASP-1$_{509-516}$; VNHDFTVV (SEQ ID NO:8)) (H. Low et al., *J. Immunol.* 160:1817-1823 (1998)) represent H-2K$^b$ restricted CTL epitopes from *T. cruzi* proteins TSA-1, ASP-2 and ASP-1, respectively. The H-2K$^b$-restricted chicken ovalbumin CTL epitope OVA$_{257-264}$ (SIINFEKL; SEQ ID NO:9) was used as a control peptide (O. Rotzschke et al., *Eur. J. Immunol.* 21:2891-4 (1991)). Lyophilized peptides were dissolved at 5 mM concentration in sterile phosphate buffer saline (PBS, 10 mM Na$_2$HPO$_4$, 2 mM KH$_2$PO$_4$, 137 mM NaCl, 8 mM KCl, pH 7.4) and stored at −20° C.

Plasmid construction. The cDNA fragment of TSA-1, ASP-1 and ASP-2 genes (D. Fouts et al., *Mol Biochem Parasitol.* 46:189-200 (1991); M. Santos et al., *Mol. Biochem.*

*Parasitol.* 86:1-11 (1997); H. Low et al., *Mol. Biochem. Parasitol.* 88:137-49 (1997)) encoding amino acid residues 78-652, 27-641, 61-705, respectively (excluding the N-terminal endoplasmic reticulum (ER) targeting signal sequence and the C-terminal GPI-anchor cleavage/attachment site and hydrophobic tail), were amplified by PCR. The recombinant pBluescript II SK+ vectors containing TSA-1 (a gift from Dr. David Fouts, University of California, Irvine, Calif.), ASP-1 and ASP-2 were used as template for PCR reactions. Forward and reverse oligonucleotides for amplification of TSA-1, ASP-1 and ASP-2 cDNA were designed to incorporate, respectively, BamHI and HindIII, BglII and XhoI, and BglII and SmaI restriction sites (underlined below) for directional cloning. Oligonucleotides were constructed on an Applied Biosystems 394 DNA/RNA synthesizer (Foster City, Calif.) at the MGIF. The forward and reverse oligonucleotides used for PCR amplification were 5'-A GGATCCATGATTGCATTTGTCGAAGGC-3' (SEQ ID NO:10) and 5'-A AAGCTTCATAGTTCACCGACACTCAGTGG-3' (SEQ ID NO:11) for TSA-1; 5'-A AGATCTTGTGGAAAGGAATTTGAGG-3' (SEQ ID NO:12) and 5'-A CTCGAGTCACAGTGGGCGGTTGTACAG-3' (SEQ ID NO:13) for ASP-1; and 5'-A AGATCTCTGTGAGGCTGCAGACGCTG-3' (SEQ ID NO:14) and 5'-A CCCGGGTTATTGGTCGCCACCGTTTCC-3 (SEQ ID NO:15) for ASP-2. The amplification products containing the A overhangs generated by Taq DNA polymerase during the PCR reaction were cloned in pUC19(T) vector.

Figure 6:
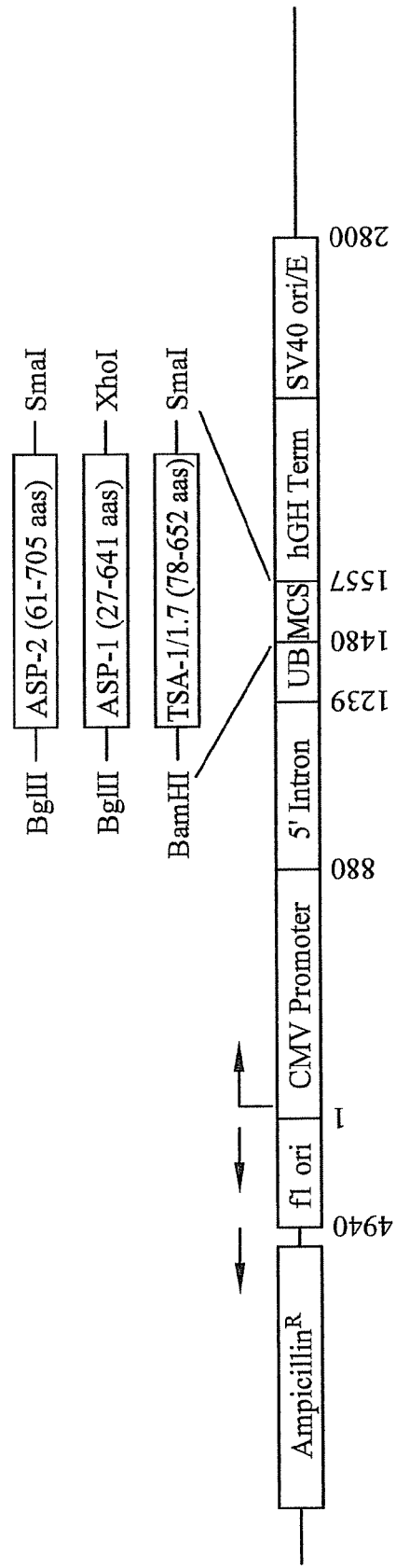
FIG. 6 is a schematic of plasmid pCMVI.UBF3/2 engineered to contain TSA-1, ASP-1 or ASP-2.

For expression in mammalian cells, the inserts from recombinant pUC19(T) plasmids were excised and cloned in the pCMVI.UBF3/2 plasmid (provided by Drs. Kathryn Sykes and Stephan A. Johnston, University of Texas Southwestern Medical Center, TX) (FIG. 6). To construct pCMVI.UBF3/2.TSA-1, pUC19(T)TSA-1 was digested with BamHI and HindIII, and the 1.7 kb TSA-1 fragment was cloned in pCMVI.UBF3/2 at similar restriction sites. To construct pCMVI.UBF3/2.ASP-1, pUC19(T)ASP-1 was digested with BglII and XhoI, and the 1.8 kb ASP-1 fragment was cloned in pCMVI.UBF3/2 at BglII and SalI sites. pCMVI.UBF3/2.ASP-2 was constructed by cloning at BglII and SmaI sites the 1.8 kb ASP-2 fragment derived from pUC19(T)ASP-2 after digestion with similar restriction enzymes. The eukaryotic expression vectors encoding murine cytokine IL-12 (pcDNA3.msp35 and pcDNA3.msp40) and murine GM-CSF (pCMVI.GM-CSF) were provided by Dr. S. A. Johnston. Recombinant plasmids were transformed into *E. coli* DH5-alpha competent cells, grown in L-broth containing 100 µg/ml ampicillin, and purified by anion exchange chromatography using the Qiagen maxi prep kit (Qiagen, Chatsworth, Calif.) according to manufacturer's specifications.

Gene expression. Expression of the ASP-1, ASP-2 and TSA-1 was assessed by transient transfection of COS7 cells with pCMVI.UBF3/2.ASP-1, pCMVI.UBF3/2.ASP-2 and pCMVI.UBF3/2.TSA-1, respectively substantially as described in Example I. Briefly, COS7 cells seeded in 6-well plates ($1\times10^5$ cells/well) were transfected with 5 µg of each plasmid DNA using Lipofectin (Gibco BRL). After 48 hours of incubation, cells were transferred to 8-well Lab Tek chamber slides (Nunc Inc., Naperville, Ill.) at $1\times10^4$ cells/well, and incubated for an additional 24 hours. Cells were fixed with ice cold methanol, and blocked with 1% bovine serum albumin (BSA) in PBS. After blocking, COS7 cells transfected with pCMVI.UBF3/2.TSA-1 or pCMVI.UBF3/2.ASP-1 were incubated with polyclonal anti-*T. cruzi* serum (1:200 dilution in PBS-1% BSA) obtained from acutely or chronically infected mice, respectively. Cells transfected with pCMVI.UBF3/2.ASP-2 were incubated with rabbit anti-ASP-2 polyclonal antiserum (1:200 dilution in PBS-1% BSA). Cells incubated with normal mouse or rabbit serum were used as negative controls. Cells were then stained with fluorescence isothiocyanate (FITC)-labeled F(ab')$_2$ goat anti-mouse or anti-rabbit IgG (1:50 dilution in PBS-1% BSA, Southern Biotech., Birmingham, Ala.) (10). Slides were mounted in 10% glycerol, 0.1 M sodium bicarbonate (pH 9), 2.5% 1,4-diazobicyclo-(2,2,2) octane, and visualized by laser scanning confocal microscopy (MRC-600, Bio-Rad Laboratories, Hercules, Calif.).

DNA immunization and infection. Female C57BL/6 mice (6 per group) were injected in the quadriceps muscles either with individual plasmid (pCMVI.UBF3/2.ASP-1, pCMVI.UBF3/2.ASP-2 or pCMVI.UBF3/2.TSA-1, 100 µg DNA/mouse) or with a mixture of ASP-1, ASP-2 and TSA-1-encoding vectors (33 µg of each plasmid/mouse). In some experiments, an additional 100 of cytokine encoding DNA (pcDNA3.msp35, pcDNA3.msp40 [IL-12] and pCMVI.GM-CSF, 33 µg each) was injected along with the antigen-encoding DNA. Mice were boosted 6 weeks after the primary immunization with an identical dose of plasmid DNA. Two weeks after the second immunization, mice were infected by intra-peritoneal injection of lethal dose of *T. cruzi* blood-form trypomastigotes ($10^5$/mouse, 5 mice per group). Parasitemia were monitored using hemacytometer counts of 10 µl tail-vein blood. Mortality was recorded daily.

Measurement of antibody responses. Cell lysates obtained from culture-derived *T. cruzi* (70% amastigotes and 30% trypomastigotes, $1.0\times10^9$ parasites/ml) was used as a source of *T. cruzi* soluble antigens for capturing serum antibodies. Pooled serum samples from immunized mice collected 2 weeks after the first and second immunization were stored at −20° C. until assayed for anti-*T. cruzi* antibodies by enzyme-linked Immunosorbant assay (ELISA) substantially as described in Example I. Briefly, flexible U bottom (96 well) polyvinyl chloride plates (Becton Dickinson & Co., Oxnard, Calif.) were coated overnight at 4° C. with 100 µl/well of *T. cruzi* soluble antigen ($5\times10^5$ parasite equivalent/well). Plates were blocked for 2 h at 37° C. with 200 µl/well of 1% non-fat dry milk (NFDM) in PBS. After washing with PBS-0.05% Tween-20 (PBST) and PBS, plates were incubated for 2 hours with test sera (100 µl/well) added in two-fold dilutions in triplicate. Plates were then incubated at room temperature for 30 minutes with 100 µl/well of horseradish peroxidase-labeled goat anti-mouse immunoglobulin (IgG+M, 1:2000 dilution in PBST-1% NFDM, Cappel, West Chester, Pa.). Color was developed with 100 µl/well of ABTS (2,2'-azino-di-(3-ethyl-benzthiazoline sulfonate) and the optical density was read at 405 nm using an automated ELISA microplate reader (Bio-Tek Instruments, Winooski, Vt.).

To determine the sub-class of antibodies generated in response to genetic immunization, plates coated with *T. cruzi* lysate were incubated first with test sera (1:200) for 2 hours at 37° C. and then with biotin-labeled goat anti-mouse-IgM, -IgG2a, -IgG2b or -IgG1 (1:1000 dilution in PBST-1% NFDM, Southern Biotech. Birmingham, Ala.) for 1 hour at 37° C. After washing with PBS-T and PBS, plates were incubated with streptavidin-conjugated horseradish peroxidase (1:2000 dilution in PBS-T, Cappel, Cochranville, Pa.). Color was developed and measured as above. Standard deviation was derived from an average of 3 replicates.

Measurement of interferon-γ (IFN-γ). Serum samples pooled from 6 mice in each group were obtained 2 weeks after the second immunization and analyzed for the IFN-γ level by specific ELISA substantially as described in G. Nabors et al. (*J. Immunol.* 146:3591-8 (1991)). Briefly, 96 well polystyrene plates were coated overnight at 4° C. with 100 µl of rat anti-mouse IFN-g Ab (R4-6A2, 4 µg/ml in PBS). After blocking for 2 hours at 37° C. with PBST-1% BSA, serum samples were added in triplicate in several two fold dilutions and incubated for 2 hours at 37° C. For detection of the IFN-γ protein, plates were incubated for 1 hour with rabbit anti-mouse IFN-γ antibody (1:1000 dilution in PBST-1% BSA). After Incubation with horseradish peroxidase-labeled goat anti-rabbit IgG (1:1000 dilution in PBST-1% BSA, Southern Biotech.), color was developed as above. Recombinant mouse IFN-γ was used to generate a standard curve.

Cytotoxic T cell activity. Cytotoxic T cell activity (CTL) activity of effector T cells obtained from plasmid DNA immunized C57BL/6 mice was measured 2 weeks after the second immunization. Effector cells were generated by incubating $5 \times 10^6$ immune spleen cells ($2.5 \times 10^6$ cells/ml TCM, 2 ml/well in 24 well plates) with 1 µM immunogenic peptide. Following 2 days of culture at 37° C. in 6% $CO_2$, the culture medium was supplemented with 5% Rat T-STIM without Con A (Collaborative Biomedical Products, Bedford, Mass.) and incubated for 4 additional days. For targets, RMA-S(H-$2K^b$) cells pre-incubated for 24 h at 29° C., 6% $CO_2$ were seeded into 24-well plates (Costar, Cambridge, Mass.) at $10^6$ cells/well in 2 ml RPMI-10% FBS. Cells were incubated overnight at 37° C. in the presence of 100 µCi of $Na_2{}^{51}CrO_4$ (Amersham, Arlington Heights, Ill.) and 1 µM of PA14 (ASP-$1_{509-516}$), PA8 (ASP-$2_{552-559}$) or pep77.2 (TSA-$1_{515-522}$) peptide, or $OVA_{257-264}$ negative control peptide. Cytolytic activity of effectors against targets was measured by the $^{51}Cr$ release assay, as previously described (H. Low et al., *J. Immunol.* 160:1817-1823 (1998); B. Wizel et al., *J. Clin. Invest.* 102:1062-71 (1998)).

Treatment of mice with neutralizing antibodies. In some experiments, mice immunized with genetic vaccines were depleted of specific T cell populations by treatment with anti-CD8 (H35.17.2, a gift from Dr. Richard Titus, Colorado State University, Fort Collins) or anti-CD4 (GK1.5, American type culture collection, Rockville, Md.) antibodies substantially as described in R. Tarleton (*J. Immunol.* 144:717 (1990)). Antibody treatment of mice started the day of infection and the specific depletion of lymphocytes was confirmed by flow cytometric analysis of splenocytes.

Histology. Some mice were sacrificed during the acute (30-45 days post-infection) or chronic (85-240 days post-infection) phase of *T. cruzi* infection for histological examination of heart and skeletal muscle tissue. Heart and skeletal muscle tissue was removed and fixed in 10% buffered formalin for 24 hours, dehydrated in absolute ethanol, cleared in xylene and embedded in paraffin. Sections (5 µm) were stained with hematoxylin and eosin and evaluated by light microscopy. Tissue parasite burden was quantitated based upon the number of parasitic pseudocysts present in sections of heart and skeletal muscles obtained from immunized/infected mice. Tissue sections were screened in >50 microscopic fields (mfs) to assess the parasite load. Tissues were also scored according to extent of inflammation.

Results

In vitro expression of *T. cruzi* proteins. *T. cruzi* genes encoding ASP-1 (amino acids 27-641), ASP-2 (amino acids 61-705), and TSA-1 (amino acids 78-652) were cloned in CMVI.UBF3/2 mammalian expression vector containing the cytomegalovirus (CMV) immediate-early gene promoter, a synthetic intron and a modified 3' UR. (untranslated region) from the human growth hormone (HGH) (FIG. 6). The cloned genes were fused to a ubiquitin encoding gene at the 5' end (FIG. 6) to promote targeting of the expressed protein to the proteosome and entry into the MHC class I pathway of antigen presentation. The expression of ASP-1, ASP-2 and TSA-1 was determined by antibody staining of COS7 cells transiently transfected with CMVI.UBF3/2.ASP-1, CMVI-UBF3/2.ASP-2 or CMVIUBF3/2.TSA-1, respectively. The intense immunofluorescent staining with a polyclonal anti-*T. cruzi* serum of COS7 cells transiently transfected with CMVIUBF3/2.ASP-1 or CMVIUBF3/2.TSA-1 confirmed the cytoplasmic expression of ASP-1 and TSA-1, respectively. The cytoplasmic expression of ASP-2 in CMVIUBF3/2-ASP-2 transfected COS7 cells was confirmed by immunofluorescent staining with a rabbit anti-ASP-2 polyclonal antiserum. In contrast, no fluorescence was detected when transfected COS7 cells were stained with normal mouse or rabbit serum, nor using either sera in cells transfected with the vector DNA alone.

Induction of *T. cruzi* specific humoral and cellular immune responses by DNA immunization. The induction of *T. cruzi*-specific antibodies following intramuscular immunization of mice with DNA vaccines was determined by ELISA. *T. cruzi*-specific antibodies were not detectable in sera collected after the first immunization. The presence of parasite specific antibodies in sera of immunized mice was assessed two weeks after the second immunization by ELISA. Sera from normal mice (NMS) and mice chronically infected with *T. cruzi* (CMS) were used as negative and positive controls, respectively. Moderate levels of parasite-specific antibodies were detected in the sera of mice immunized with CMVIUBF3/2.ASP-2 (FIG. 7A), but remained below the limit of detection in sera from mice immunized with CMVIUBF3/2.ASP-1 or CMVIUBF3/2.TSA-1. Likewise, control mice immunized with vector DNA alone or cytokine vectors only exhibited no parasite-specific antibodies in the sera.

ASP-1, ASP-2 and TSA-1, all contain $H-2K^b$-restricted epitopes that are recognized by CTLs induced in *T. cruzi* infected C57BL/6 mice (B. Wizel et al., *J. Immunol.* 159: 6120-30 (1997); H. Low et al., *J. Immunol.* 160:1817-1823 (1998)). We determined whether antigen-specific CTLs were induced in mice following immunization with the ASP-1, ASP-2 or TSA-1 encoding plasmid DNA constructs. Two weeks after second immunization, splenocytes from one mouse in each group were harvested and stimulated in vitro with ASP-1, ASP-2 or TSA-1 derived $H-2K^b$ restricted CTL epitope peptides (PA14, PA8 and pep77.2 respectively, 1 µM). The effectors derived from these cultures were tested for their ability to lyse $^{51}Cr$ labeled RMA-S cells pulsed with homologous peptide(s) or the irrelevant peptide $OVA_{257-264}$. Moderate levels of peptide-specific lytic activity were evident in mice immunized with CMVI.UBF3/2.ASP-1, CMVI.UBF3/2.ASP-2 or CMVI.UBF3/2.TSA-1 (FIG. 8A). Splenocytes from mice immunized with vector DNA did not show CTL activity against any of the peptide-sensitized target cells (FIG. 8A).

Enhancement of *T. cruzi* specific immune responses by co-delivery of cytokine adjuvants. IL-12 and GM-CSF have shown utility as genetic adjuvants, and in addition have been shown to be very important in controlling the disease outcome to *T. cruzi* infection (E. Olivares Fontt et al., *Parasite Immunol.* 17:135-41 (1995); E. Olivares Fontt et al., *Infect. Immun.* 64:3429-34 (1996); I. Abrahamsohn, *Braz. J. Med. Biol. Res.* 31:117-21 (1998); J. Silva et al., *Braz. J. Med. Biol. Res.* 31:111-5 (1998)). We determined whether the immune response to *T. cruzi* genetic vaccines is enhanced by co-administration of DNA expression constructs encoding IL-12 and GM-CSF. Immunization of mice with cytokine adjuvants and antigen-encoding plasmid(s) resulted in splenomegaly, an indicator of increased B and T cell proliferation. In addition, a significant increase in the level of parasite specific humoral and cellular immune responses was observed in mice immunized with cytokine adjuvants and the antigen-encoding vector(s) relative to mice immunized with antigen-encoding vector alone (FIGS. 7 and 8).

Figure 7A:
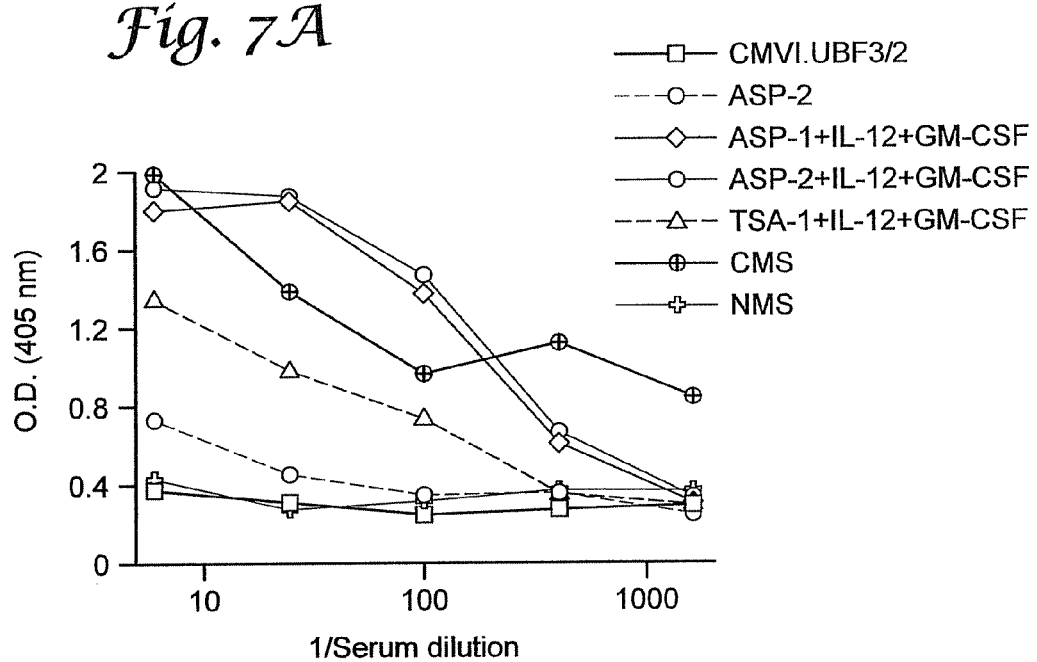
FIG. 7 shows that humoral immunity induced by intramuscular immunization of B6 mice with *T. cruzi* antigen-encoding plasmids is enhanced by cytokine adjuvants; (A) *T. cruzi* specific antibody levels; (B) Antibody sub-types in mice immunized with genetic vaccines.
Figure 7B:
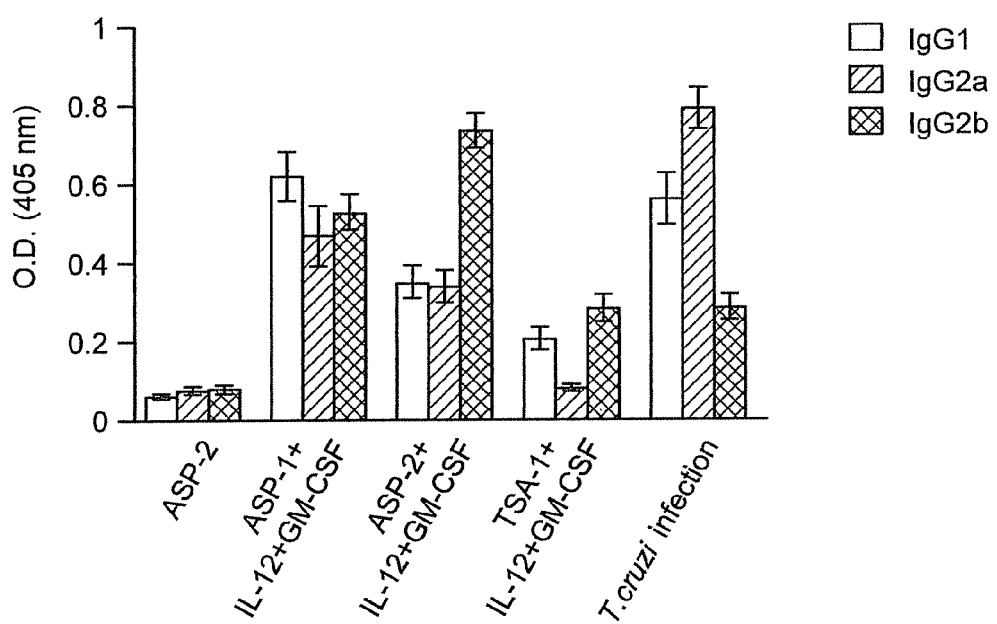

The antibody levels in sera of mice injected with cytokine-expression constructs and CMVI.UBF3/2.ASP-1 or CMVI.UBF3/2.ASP-2 were comparable to that of mice chronically infected with *T. cruzi* (FIG. 7A). Mice immunized with pCMVI.UBF3/2.TSA-1 and cytokine-encoding plasmids also exhibited a significant level of serum antibodies (FIG. 7A). Mouse sera pooled from individual tail blood samples two weeks after the second immunization were tested for the presence of parasite specific antibody sub-types by ELISA. The increase in antibody response in mice immunized with cytokine-encoding plasmids and CMVI.UBF3/2.ASP-1, CMVI.UBF3/2.ASP-2 or CMVI.UBF3/2.TSA-1 was evident in IgG1, IgG2a and IgG2b antibody subclass (FIG. 7B).

Delivery of cytokine-encoding vectors with the antigen-encoding plasmids significantly enhanced the activation of antigen-specific CTLs (compare FIGS. 8A and B). Splenocytes obtained 2 weeks after second immunization were stimulated in vitro with antigen-specific peptides. In comparison to splenocytes obtained from mice immunized with CMVI.UBF3/2.ASP-1, CMVI.UBF3/2.ASP-2 or CMVI.UBF3/2.TSA-1, spleen cells from mice co-immunized with cytokine adjuvants and antigen-encoding vector(s) exhibited a 2-4 fold increase in antigen-specific cytolytic activity (FIGS. 8A & B, 40:1 E:T ratio). In addition, IFN-γ in sera pooled from individual tail blood samples 2 weeks after the second immunization was assessed by ELISA. Serum IFN-γ level in mice immunized with CMVI.UBF3/2, CMVI.UBF3/2.ASP-1, CMVI.UBF3/2.TSA-1, or cytokine adjuvants was ~0.05-0.25 ng/ml. Serum levels of IFN-γ were increased by >4-fold when mice were immunized with cytokine-expressing plasmids plus CMVI.UBF3/2.ASP-1, CMVI.UBF3/2.ASP-2 or CMVI.UBF3/2.TSA-1 as compared to mice immunized with antigen-encoding vector(s) only (FIG. 8C). These results demonstrate that the *T. cruzi*-specific immune responses elicited by DNA vaccines can be enhanced by co-administration of cytokine adjuvants.

Protection from lethal *T. cruzi* infection. We next determined whether the immune responses elicited in mice upon immunization with ASP-1, ASP-2 or TSA-1-encoding constructs were protective against *T. cruzi* infection. Two weeks after the second immunization, mice were challenged with a lethal dose of *T. cruzi* ($10^5$ BFT/mouse) and blood parasite levels and mortality was monitored.

Figure 9A:
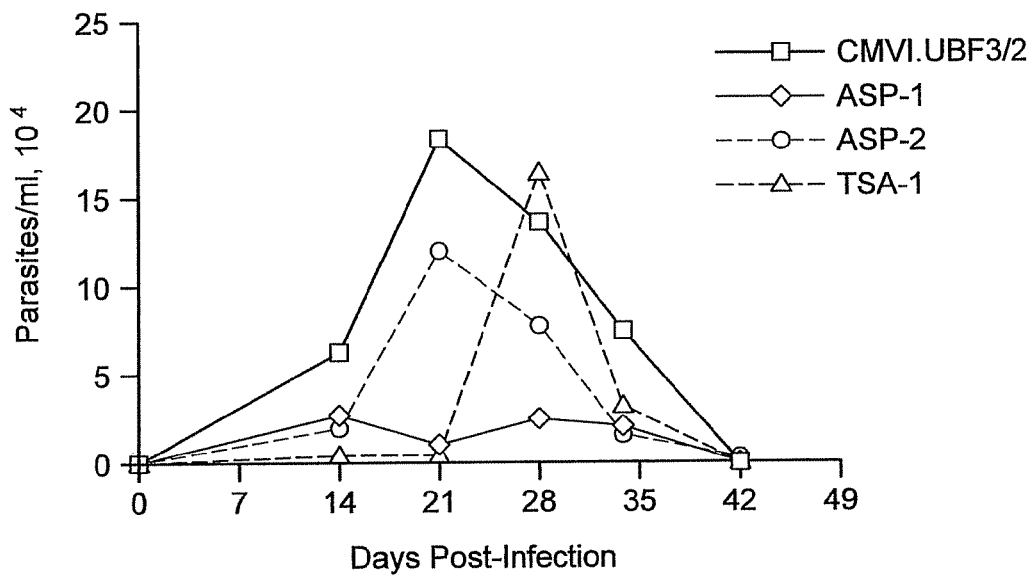
FIG. 9 shows (A, C) parasitemia and (B, D) mortality in mice immunized with DNA vaccine containing plasmid CMVI.UBF3/2 encoding ASP-1, ASP-2 or TSA-1 (C, D) with or (A, B) without cytokine adjuvants.
Figure 9B:
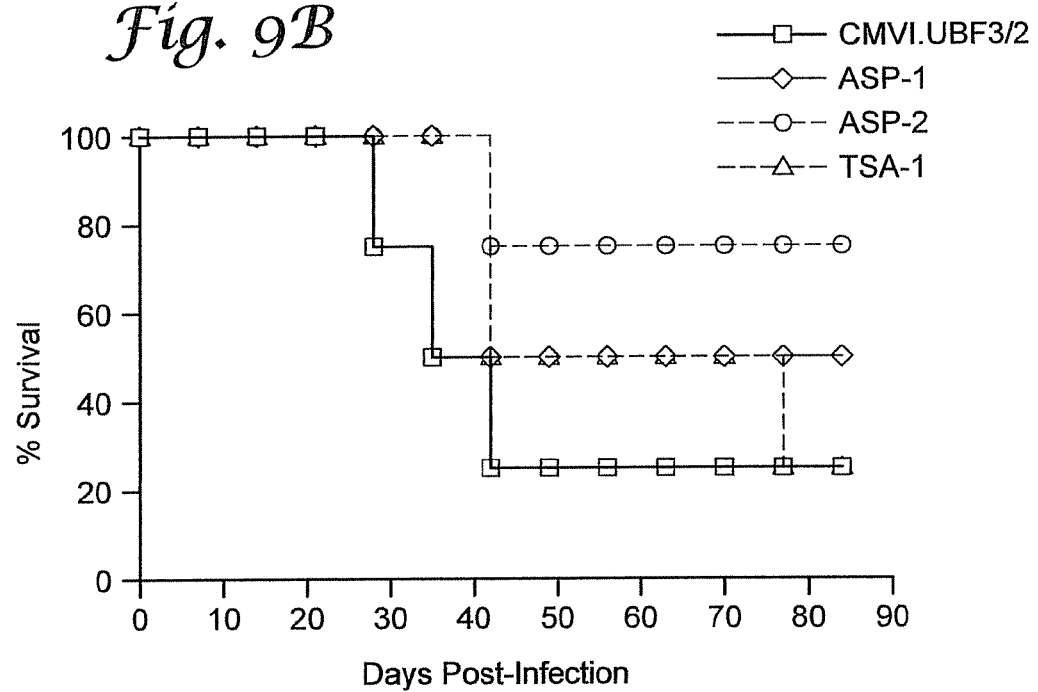

All mice injected with ASP-1 DNA vaccine exhibited lower parasitemia levels as compared to either ASP-2 or TSA-1 immunized mice, or control mice injected with vector DNA (FIG. 9A). As shown in FIG. 9B, 75% of mice immunized with the CMVI.UBF3/2 encoding ASP-1, ASP-2 or TSA-1 survived a minimum of 42 days post-infection (dpi), while 75% mice injected with the control vector DNA succumbed to *T. cruzi* infection by 42 dpi. In pooled results from 4 experiments, 40% (4/10) of mice immunized with CMVI.UBF3/2.ASP-1, 66% (10/15) of mice immunized with CMVI.UBF3/2.ASP-2 and 30% (3/10) of mice immunized with CMVI.UBF3/2.TSA-1 were protected from challenge *T. cruzi* infection while 90% (18/20) of mice immunized with CMVI.UBF3/2 succumbed to infection.

Figure 9C:
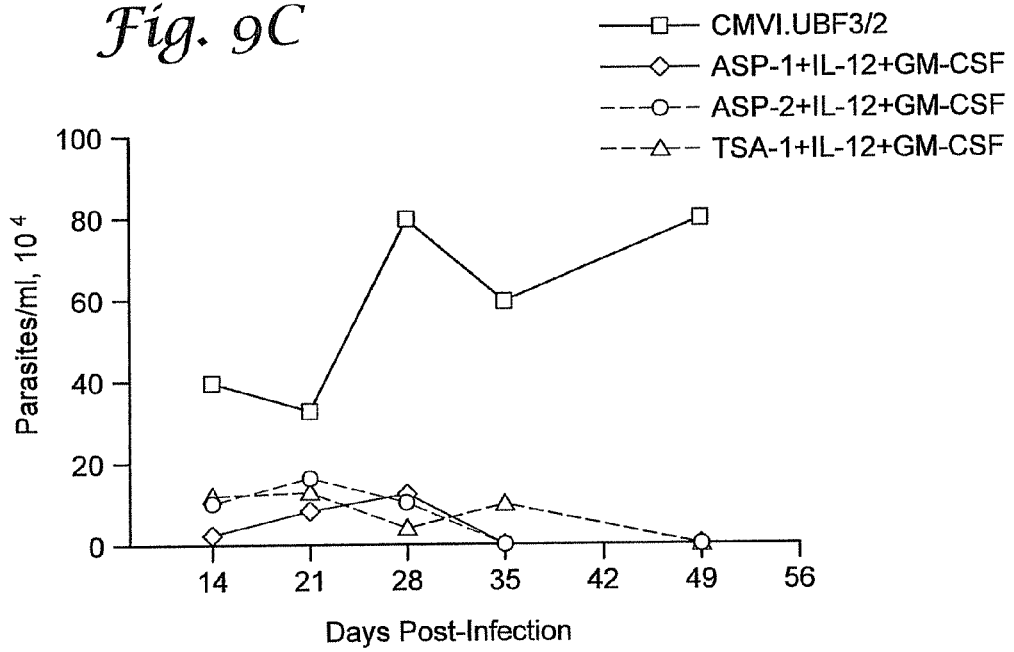
Figure 9D:
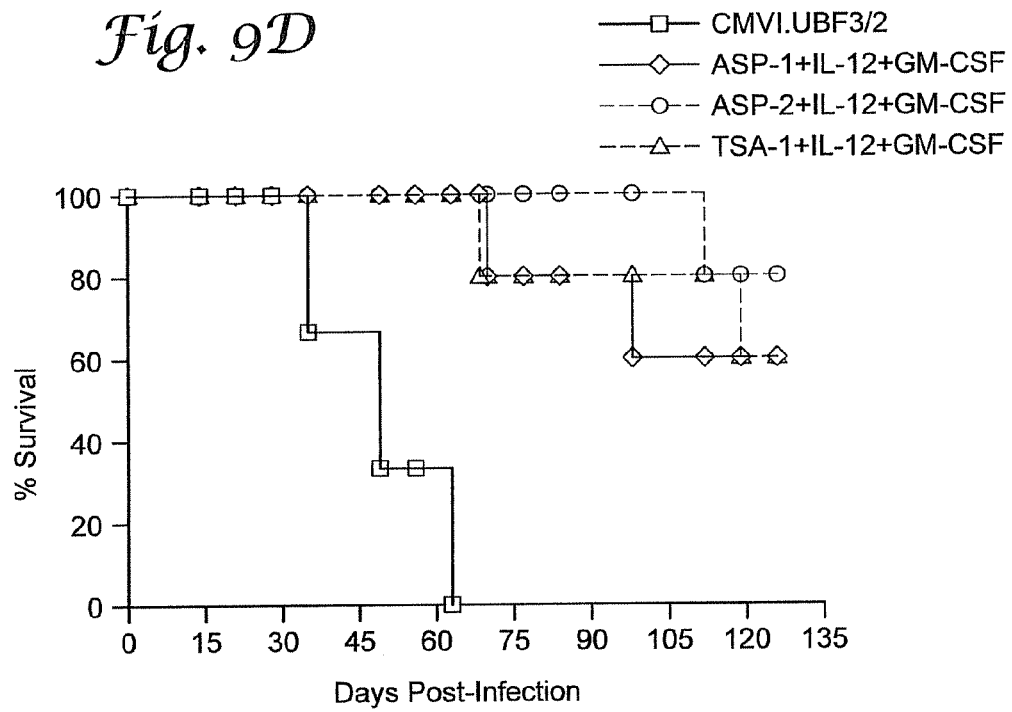

The enhanced activation of humoral and cellular immune responses in mice receiving the combination of antigen-encoding plasmids and cytokine-expression constructs was associated with increased resistance to *T. cruzi* infection. All mice vaccinated with cytokine-expressing plasmids and CMVI.UBF3/2.ASP-1, CMVI.UBF3/2.ASP-2 or CMVI.UBF3/2.TSA-1 efficiently controlled the acute infection; parasitemias became undetectable 35 days post-infection (FIG. 9C), and all mice survived at least 70 days post-infection (FIG. 9D). In comparison, all mice injected with vector DNA alone exhibited high blood parasite levels and succumbed to *T. cruzi* infection by 62 days post-infection (FIGS. 9C and D).

Figure 10A:
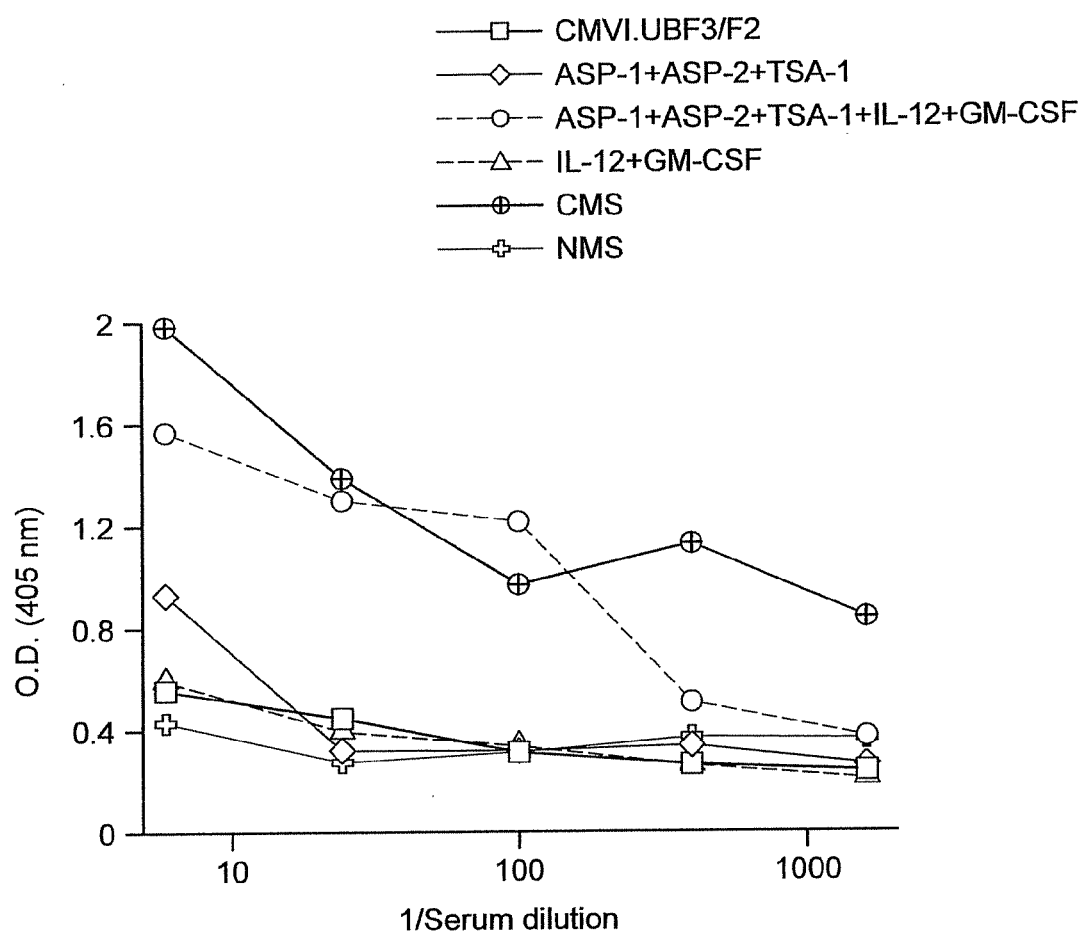
FIG. 10 shows that elicitation of protective immune responses by multi-component nucleic acid vaccine can be augmented by cytokines. Two weeks after the second immunization, measurements of (A) serum antibody levels (using ELISA) and (B-E) CTL activity were made. For quantitation of CTL activity, splenocytes from immunized mice were stimulated in vitro with antigen-specific peptide (B) PA8, (C) PA14, (D) pep77.2 or (E) a mixture of PA8+PA14+pep77.2 (E). Effectors generated from these splenocytes were then tested in a 5 hour $^{51}$Cr release assay against RMA-S target cells sensitized with either the homologous peptide (PA14, PA8 or pep77.2, open symbols) or pulsed with non-specific peptide (OVA$_{257-264}$, filled symbols).

Co-immunization with multiple antigen-encoding expression vectors induces resistance to *T. cruzi* infection and Chagas disease. In an attempt to maximize the protective capacity of genetic immunization for *T. cruzi* infection, C57BL/6 mice were immunized with a mixture of ASP-1, ASP-2 and TSA-1 encoding vectors, with or without cytokine-expressing plasmids. Mice injected with vector DNA or cytokine-encoding plasmids only were used as controls. Serum antibody levels were measured using ELISA two weeks after the second immunization. As expected, mice immunized with antigen (ASP-1+ASP-2+TSA-1)-encoding vectors with or without cytokine-expression constructs showed parasite-specific antibody responses and CTL activity (FIG. 10). Mice vaccinated with CMVI.UBF3/2 encoding ASP-1, ASP-2 and TSA-1 plus cytokine adjuvants (IL-12+GM-CSF) exhibited a 1.5-3-fold increase in parasite-specific serum antibodies (FIG. 10A) and IFN-γ, and an overall increase in antigen-specific CTL activity in comparison to mice immunized with a mixture of antigen-encoding constructs alone (FIGS. 10B-E). An inhibitory or additive effect on elicitation of antigen-specific immune responses was not observed in mice immunized with the combination of three antigen-encoding vectors.

Figure 11A:
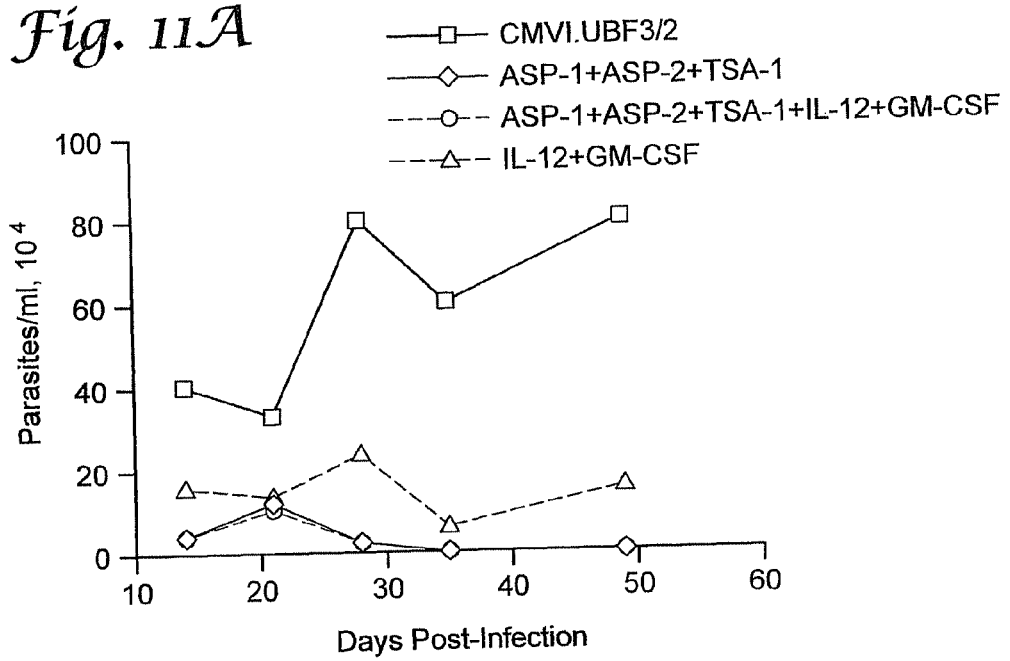
FIG. 11 shows (A) parasitemia and (B) mortality in mice immunized with multi-component nucleic acid vaccine and infected with *T. cruzi*.
Figure 11B:
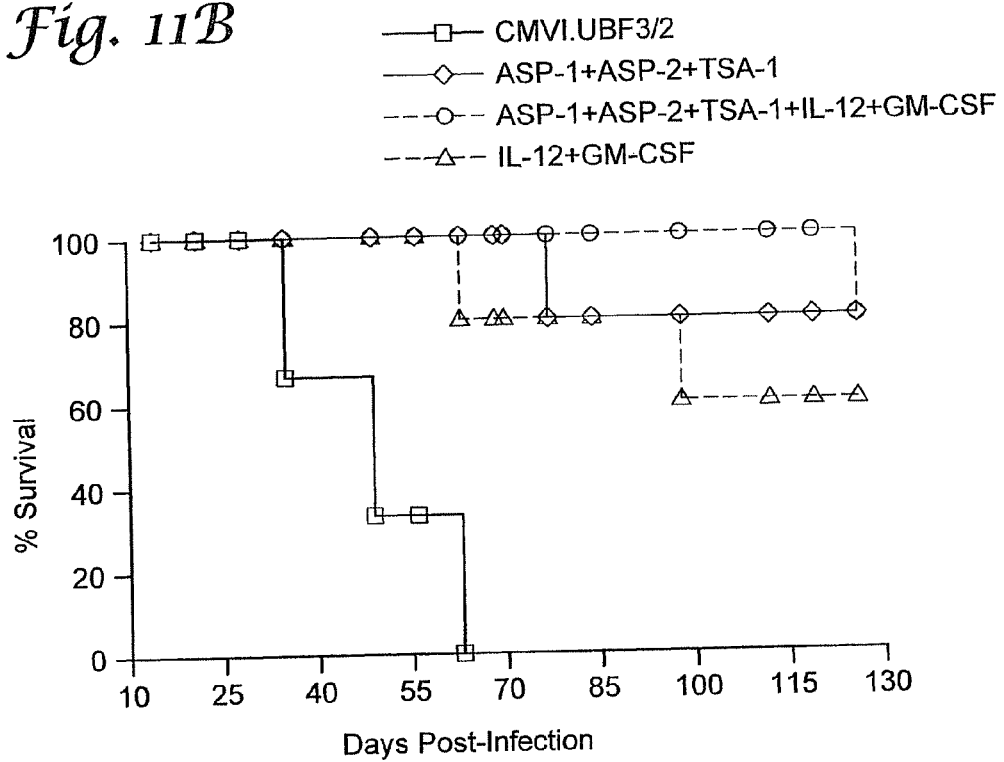

Immunization of mice was followed 2 weeks later by intraperitoneal infection with blood-form trypomastigotes ($10^5$/mouse). Immunization of mice with multiple antigen-encoding plasmids with or without cytokine-expression plasmids induced resistance to *T. cruzi* infection, although not at a level that was significantly better than that induced with single antigen-encoding plasmid (FIG. 11). In pooled results from 2 experiments, 58% (7/12) mice immunized with the three antigen-encoding vectors and >80% (10/12) mice immunized with antigen-encoding vectors plus cytokine-expression plasmids were protected from challenge *T. cruzi* infection. Interestingly, mice vaccinated with cytokine (IL-12+GM-CSF) adjuvants only exhibited better control of blood parasite burden and delayed time to death compared to control mice which consistently showed an increase in blood parasite level (FIG. 11A) and succumbed to infection (FIG. 11B).

Histopathological analysis. The above results suggested that genetic immunization can be used to generate and modulate the immune responses that assure survival from challenge *T. cruzi* infection. However, survival from *T. cruzi* infection does not affirm the absence of Chagas' disease. We therefore determined if generation of effector immune responses by genetic immunization would result in decreased severity of disease during the chronic stage of *T. cruzi* infection. For this analysis, sections from heart and skeletal muscle of mice immunized and challenged with $10^5$ BFT were assessed at various time intervals for tissue parasite burden and inflammation. Mice were infected two weeks after second immunization with a lethal dose of *T. cruzi* BFT ($10^5$/mouse). Irrespective of the immunization conditions, mice in all groups exhibited moderate to high inflammatory responses in skeletal muscles and heart during acute phase of infection (45 dpi) (FIG. 12, Table 2). However, the extent of tissue parasitism varied depending upon the immunization conditions. Mice immunized with a mixture of antigen-encoding vectors plus cytokine-expression constructs exhibited the lowest level of tissue parasite burden (0-2 parasite pseudocysts per microscopic field (mf), FIG. 12D, Table 2).

TABLE 2

Histopathological analysis of the skeletal muscle from DNA immunized mice upon infection with *T. cruzi*[a]

| DNA Immunization | IL-12 + GM-CSF[b] | Inflammation[c] | | Pseudocysts/filed[d] |
|---|---|---|---|---|
| | | Acute phase[d] | Chronic phase[e] | |
| CMVLUBF3/2 | − | ++++ | +++ | 8-10 |
| CMVLUBF3/2 | + | ++++ | +++ | 2-6 |
| ASP-1 | − | + | +++ | 7-10 |
| ASP-1 | + | +++ | ++ | 2-5 |
| ASP-2 | − | +++ | ++ | 3-8 |
| ASP-2 | + | ++ | + | 1-4 |
| TSA-1 | − | ++/+++ | ++ | 2-8 |
| TSA-1 | + | +++/++++ | +/++ | 2-5 |
| ASP-1 + ASP-2 + TSA-1 | − | ++++ | + | 5-9 |
| ASP-1 + ASP-2 + TSA-1 | + | ++++ | +/− | 0-2 |

[a]Results are from a mean of 2-3 experiments.
[b]When indicated, IL-12 and GM-CSF encoding plasmids (33 μg each/mouse) were administered with 100 μg total of antigen-encoding DNA.
[c]Scores for degree of inflammation were obtained as described in Materials and Methods.
[d]Tissue were collected for histopathological analysis and quantitation of the parasitic pseudocysis on 45 dpi.
[e]Tissues were collected for histopathological analysis during chronic phase of infection 80-240 dpi.

Figure 12A:
FIG. 12 shows hematoxylin and eosin stained tissue sections from skeletal muscles of DNA immunized mice during acute phase of *T. cruzi* infection. C57BL/6 mice were immunized with (A) vector DNA, (B) cytokine plasmids, (C) antigen-encoding vectors, and (D) a mixture of ASP-1, ASP-2, TSA-1 expression constructs+cytokine expressing plasmid twice at 6-week intervals. Tissue sections for histological analysis were obtained 45 dpi. Parasite infected cells are indicated by arrows. Original magnification 200×.
Figure 12B:
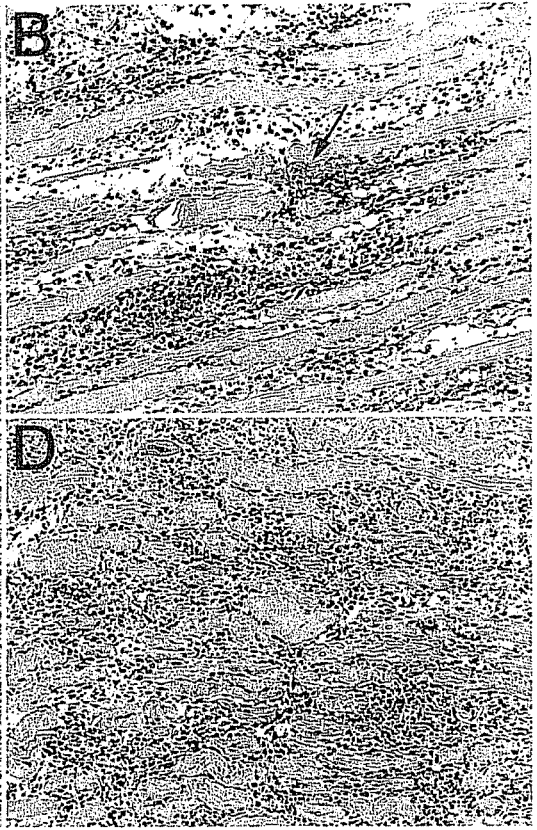
Figure 12C:
Figure 12D:

In comparison, mice injected with ASP-1, ASP-2 or TSA-1-encoding vector (individually) plus cytokine-expression plasmids (1-5 parasite nests/mf) or mice that received the antigen-encoding vector(s) (individually or in combination), cytokine plasmids only, or empty plasmid alone (2-10 parasite nests/mf) exhibited moderate to high tissue parasites (FIGS. 12A-C, Table 2)

Figure 13A:
FIG. 13 shows control of tissue inflammation and parasite burden by prophylactic DNA immunization. Histological analysis of skeletal muscles of mice immunized with (A) vector alone, (B) cytokine-expressing plasmids, (C) ASP-1, ASP-2 and TSA-1-encoding plasmids, or (D) a mixture of antigen-encoding constructs plus cytokine adjuvants.
Figure 13B:
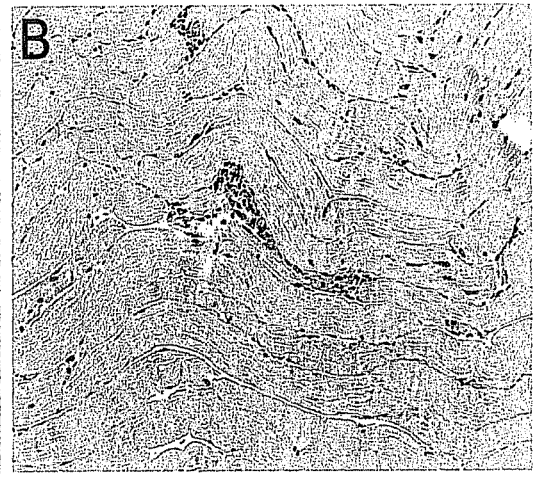
Figure 13C:
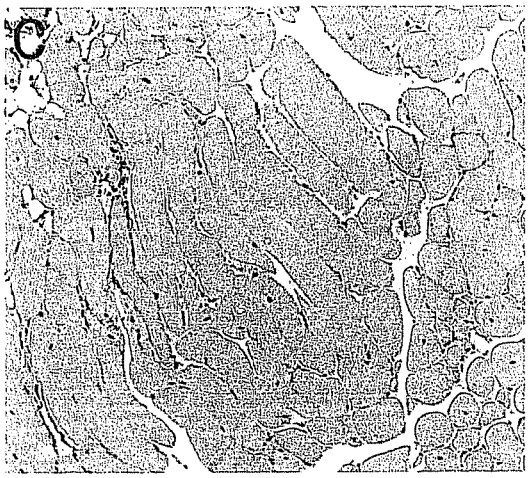
Figure 13D:
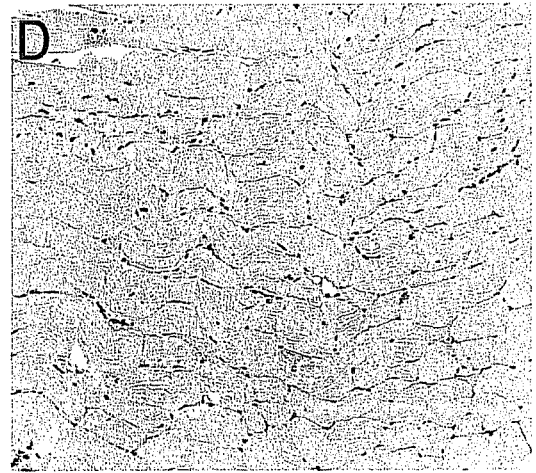

Tissues were collected 150 days post-infection. The extent of inflammation and associated tissue damage in heart tissue and skeletal muscle during the chronic phase of infection was remarkably reduced in mice immunized with a mixture of *T. cruzi* antigen-encoding constructs with or without cytokine-expression constructs (FIG. 13D). Although a majority of the animals in the control group (>90%) died due to high blood and tissue parasite burden during the acute phase of *T. cruzi* infection, a few animals that did survive to chronic phase of infection showed extensive skeletal muscle inflammation and tissue necrosis (FIG. 13A, Table 2), the hallmarks of Chagas' disease development. In sharp contrast, mice surviving infection following immunization with cytokine genes alone, the mixture of antigen-encoding plasmids, or ASP-1, ASP-2 or TSA-1-encoding plasmid plus cytokine-expression vectors; all exhibited moderate inflammatory response up to day 240 post-infection (time point after which experiments were terminated). These results demonstrate that the DNA vaccines used in this study are effective in controlling the tissue parasite burden and consequently the associated symptoms of chronic Chagas' disease.

Depletion of CD4+ or CD8+ T cells and loss of resistance to *T. cruzi* infection. We next determined whether vaccination with ASP-1, ASP-2 or TSA-1 genes provided protection from *T. cruzi* infection through CD4+ and/or CD8+ T cell dependent immune mechanisms. C57BL/6 female mice were immunized twice with vector DNA or a mixture of antigen-encoding plasmids plus cytokine-expressing plasmids, and challenged with 1×10$^5$/mouse BFT. During the course of infection, some mice (as indicated) were treated with the anti-CD8 or anti-CD4 antibody at weekly intervals. As determined by flow cytometric analysis, treatment with H35.17.2 or GK1.5 antibodies resulted in specific depletion of >95% CD8+ or CD4+ T cells, respectively.

Figure 14A:
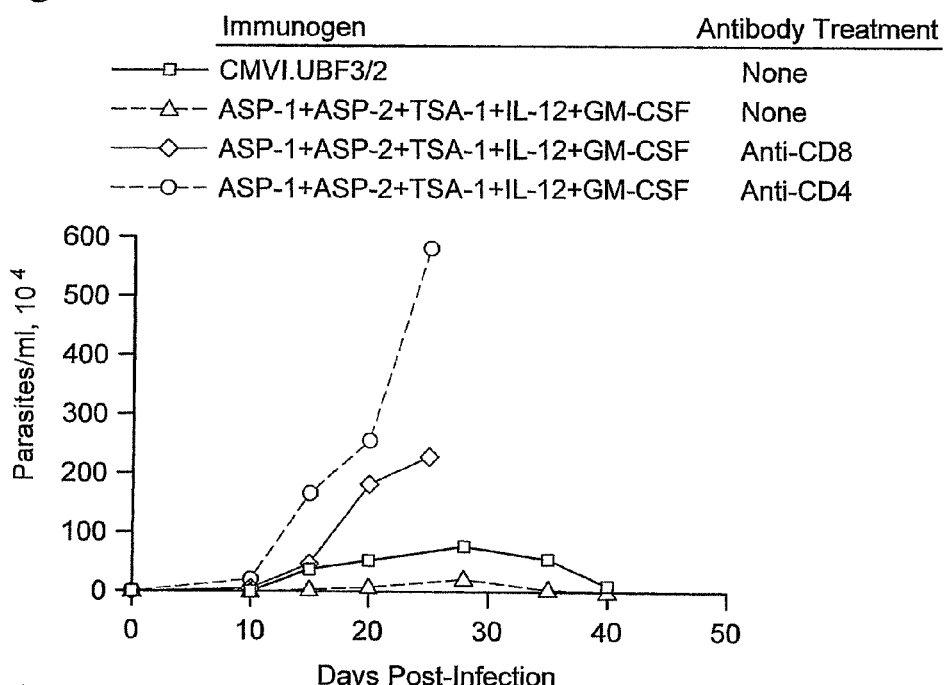
FIG. 14 shows the effect of depletion of T cell population on protective efficacy of DNA vaccines against *T. cruzi* infection; (A) parasitemia; (B) mortality.
Figure 14B:
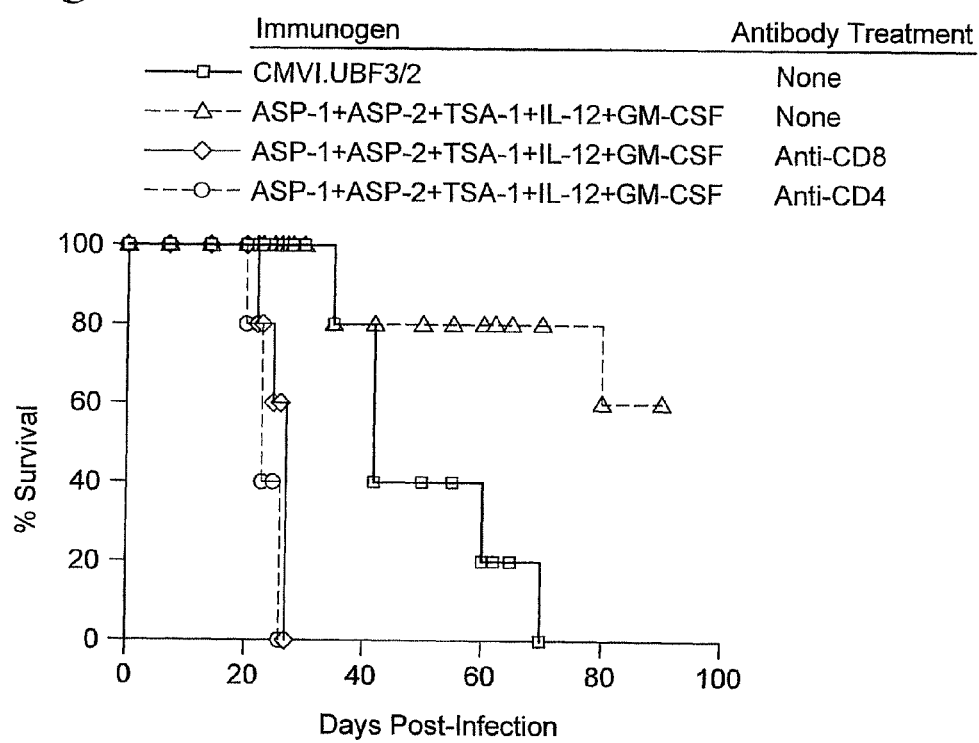
Figure 15A:
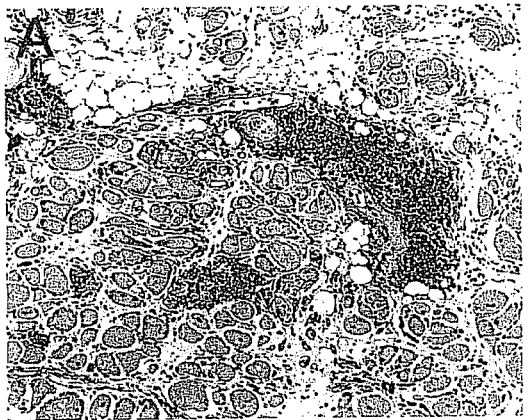
FIG. 15 shows control of tissue inflammation and parasite burden by therapeutic DNA immunization. Histological analysis of skeletal muscles of mice immunized with (A) vector alone, (B) cytokine-expressing plasmids, (C) ASP-1, ASP-2 and TSA-1-encoding plasmids, or (D) a mixture of antigen-encoding constructs plus cytokine adjuvants.
Figure 15B:
Figure 15C:
Figure 15D:

Depletion of either of the T cell population resulted in a decreased ability of immunized mice to control *T. cruzi* infection. As compared to untreated mice, depletion of either of the CD4+ or CD8+ T cells in mice treated with GK1.5 or H35.17.2 antibodies resulted in a substantial increase in blood parasite burden (FIG. 14A). All mice in the treated groups depleted of either of the T cell population died before day 30 of infection. These results suggest that both CD4+ and CD8+ T cells are required for the elicitation of effective immune responses and protection from *T. cruzi* infection in DNA immunized mice.

Discussion

In this study, we have determined the utility of *T. cruzi* genes encoding for ASP-1, ASP-2 and TSA-1 as genetic vaccine(s) for control of *T. cruzi* infection and treatment of Chagas disease in a murine model system. All three antigens (ASP-1, ASP-2 and TSA-1) are expressed as GPI-anchored proteins by infective or intracellular stages of *T. cruzi*, and have previously been shown to be recognized by CTLs from chronically infected mice and humans (H. Low et al., *J. Immunol.* 160:1817-1823 (1998); B. Wizel et al., *J. Clin. Invest.* 102:1062-1071 (1998); B. Wizel et al., *J. Immunol.* 159:6120-30 (1997)). In addition, ASP-1, ASP-2 and TSA-1 elicit strong antibody responses in *T. cruzi* infected mice (R. Wrightsman et al., *J. Immunol.* 153:3148-3154 (1994); M. Santos et al., *Mol. Biochem. Parasitol.* 86:1-11 (1997); A. Pan et al., *J. Immunol.* 143:1001 (1989)).

We found that intramuscular immunization of mice with ASP-1, ASP-2 or TSA-1 encoding plasmids (individually or in combination) resulted in elicitation of moderate antigen-specific CTL activity, and marginal to no Ab responses. The restricted induction of antibodies upon delivery of DNA vaccines via intramuscular route has previously been reported by other labs (M. Barry et al., *Vaccine* 15:788-91 (1997)). Nevertheless, mice immunized with ASP-1, ASP-2 or TSA-1 encoding vectors exhibited a degree of protection from *T. cruzi* infection as evidenced by decrease in blood parasite burden and longevity, and control of Chagas' disease during the chronic phase of *T. cruzi* infection.

To maximize the protective capacity of DNA vaccines to *T. cruzi* infection, we refined our immunization strategies to enhance the magnitude of the immune responses by co-delivery of immunologic adjuvants along with the antigen-encoding vector(s). IL-12 and GM-CSF were selected for co-immunization with antigen-encoding vectors. The importance of IL-12 and GM-CSF in immune control of *T. cruzi* has been shown by the fact that treatment of mice with IL-12 or GM-CSF neutralizing antibodies results in increased susceptibility to *T. cruzi* infection, while in vivo delivery of rIL-12 or rGM-CSF enhances resistance to *T. cruzi* infection. In addition, we and others have shown by infection studies in knock-out mice deficient in various immune functions that immunity to *T. cruzi* requires the induction of antibodies, CTLs and Th1 type cytokines. Immunization of mice with GM-CSF and IL-12-encoding plasmid DNA along with *T. cruzi* antigen-encoding vectors was expected to elicit more efficient humoral and cellular immune responses and to direct the host immune activity towards a type1 cytokine response.

Several immunologic effects of co-administration of cytokines with DNA vaccines were observed. First, co-delivery of cytokines resulted in splenomegaly, an indicator of increase in B and/or T cells number and enhanced immune reactivity. In addition, we observed an increase in the induction of antigen-specific cellular and humoral immune responses and secretion of Th1 cytokines by co-administration of IL-12 and GM-CSF. We detected moderate to no *T. cruzi*-specific antibodies upon immunization of mice with *T. cruzi* gene(s), but a significantly increased antibody response was detected when DNA immunogen(s) were delivered with cytokine-expressing plasmids. The local presence of GM-CSF at the site of antigen expression might have helped either by increased proliferation of antigen presenting cells or by increasing the MHC-associated antigen presentation, leading to more effective, antigen-specific B cell activation and antibody production. Enhancement of antibody responses to viral antigens by co-inoculation of DNA encoding GM-CSF has been previously shown (J. Sin et al., *Eur. J. Immunol.* 28:3530-4038 (1998); J. Kim et al., *J. Interferon Cytokine Res.* 19:77-84 (1999)).

The consistent and dramatic increase in antigen-specific CTL activity in mice co-immunized with cytokine adjuvants and *T. cruzi* antigen-encoding vectors (individually or in combination) could also be in part attributed to the local presence of IL-12, a key cytokine involved in $CD8^+$ T cell activation and proliferation. The lytic activity of effectors generated from immunized mice against target cells pulsed with non-specific peptides was statistically insignificant, suggesting that the increase in cytotoxic response by co-administration of cytokines (IL-12) was the result of the activation of antigen-specific T lymphocytes, not due to non-specific lytic activity of NK cells. As the peptides used in CTL assays were MHC class I-restricted, we conclude that the CTL activity induced by genetic immunization is MHC class I-restricted and $CD8^+$ T cell dependent.

In addition to CTL activity, we also observed an increase in IFN-γ secretion and IgG2a type antibody in mice co-immunized with cytokine adjuvants and antigen-encoding DNA. However, increase in IFN-g production in mice receiving cytokine adjuvant was also associated with consistent increase in IgG1 and IgG2b antibodies. Previous studies have indicated the increase in IgG1 in immunized mice that exhibit increased IFN-γ production upon treatment with TL-12 (J. Bliss et al., *J. Immunol.* 156:887-94 (1996)). The co-delivery of IL-12 (and GM-CSF) with antigen-encoding vectors was expected to enhance the type 1 immune response; however, the vaccine cocktail used in the present study was not designed to block the production of type 2 cytokines. Therefore the failure to polarize the T cells completely towards type 1, the inability to generate threshold level of IFN-g required for antibody switch to IgG2a, or the production of substantial level of type 2 cytokines (e.g. IL-4) in mice immunized with antigen-encoding plasmid plus cytokine adjuvants might have contributed to the induction of both type 1 and type 2 antibody subtypes.

Mice immunized with ASP-1, ASP-2 or TSA-1 encoding vectors with or without cytokine expressing plasmids exhibited a variable degree of protection from *T. cruzi* infection. The protection was related to the prior induction of immune responses, mice immunized with CMVI.UBF3/2.ASP-2 or the mixture of antigen-encoding vectors plus cytokine adjuvants mounted the maximal immune responses in terms of anti-*T. cruzi* antibodies, CTL activity and type 1 cytokines and were most resistant to *T. cruzi* infection as evidenced by decreased blood parasitemia and longevity. The loss of resistance in vaccinated mice depleted of either of the T cell population supports the conclusion that ASP-1, ASP-2 and TSA-1 encoding DNA vaccines conferred protection from *T. cruzi* infection through the participation of $CD4^+$ and $CD8^+$ T cells. In this regard, previous reports from ours and other labs have demonstrated that both $CD4^+$ and $CD8^+$ T cells play an important role in determining the disease outcome in murine model of *T. cruzi* infection. It is intriguing that mice immunized with cytokine adjuvants were better equipped to control blood and tissue parasites, and inflammation than mice injected with vector alone. We consider that the presence of IL-12 and GM-CSF at the time of infection (2 weeks following the second immunization) might have augmented the parasite-specific responses induced by the challenge infection.

The most striking observation in this study is perhaps the demonstration that the prior induction of systemic immunity by DNA vaccines reduced the severity of Chagas disease during chronic phase of *T. cruzi* infection. The infection experiments in this study were designed such that the efficacy of DNA vaccine(s) was determined based upon survival from *T. cruzi* infection. Therefore, mice were infected with a high dose of BFT ($1\times10^5$) that was sufficient to kill a majority of the control animals during the acute phase of infection, long before the development of chronic chagasic symptoms. Under such conditions, mice immunized with antigen-encoding vector(s) and cytokine adjuvants not only survived the challenge *T. cruzi* infection, but also controlled the blood and tissue parasite burden and exhibited a dramatic reduction in skeletal and heart muscle inflammation and necrosis during the chronic phase of *T. cruzi* infection. It is likely that effective control of parasites early during the acute phase of infection resulted in the control of tissue parasite load and associated Chagas' disease development. Regardless of the mechanism, our results provide the first evidence that DNA vaccination is a viable approach to reduce the severity of chronic *T. cruzi* infection. Additional experiments using appropriate mouse-*T. cruzi* combinations so that control animals survive and develop chronic phase of Chagas' disease are in progress for the comparative analysis and the quantification of effectiveness of DNA vaccines for the prevention of Chagas disease in a variety of models.

In conclusion, we have demonstrated that (i) genetic vaccines constituted by ASP-1, ASP-2, TSA-1 are useful for the induction of immunity to *T. cruzi* infection and the prevention of Chagas disease (ii) individual or multiple antigens can be delivered for the elicitation of antigen-specific immune responses, (iii) the quality and the quantity of immune responses elicited by *T. cruzi* DNA vaccine(s) can be enhanced by co-delivery of cytokine expression plasmids, (iv) the stimulation and maintenance of antigen-specific $CD4^+$ and $CD8^+$ T cells is essential for efficient control of *T. cruzi* infection by genetic immunization. Although the three genes tested in this study failed to prevent *T. cruzi* infection or eliminate the parasites from infected animals, they did control infection and Chagas' disease.

Example III

Therapeutic Genetic Immunization of Mice Infected with *T. cruzi* Reduces Disease Severity The protocol and genes used here were the same as with the prophylactic immunization described in Example II. Mice were infected with 1000 blood-faun trypomastigotes of the Brazil strain of *T. cruzi* and then 4.5 months later, immunized with 33 ug each of the TSA-1, ASP-1 and ASP-2 plasmids in combination with the IL-12 and GM-CSF-containing plasmids as in Example H. Approximately one year later, these mice were sacrificed and the skeletal and heart muscle subjected to standard histopathological analysis. Mice which received the empty plasmid or cytokine genes alone showed extensive inflammation and tissue scarring characteristic of Chagas' disease. Mice receiving the plasmids containing the *T. cruzi* genes or the combination of *T. cruzi* genes and cytokine plasmids were essentially free of inflammation and disease (FIG. 15).

Example IV

Comparison of Protective Cellular and Humoral Immune Responses to *Trypanosoma Cruzi* Infection in B6 and C3H Mice Using DNA Vaccines Methods. Truncated version of the genes encoding trans-sialidase super-family members ASP-1 (amino acids 27-641), ASP-2 (amino acids 61-705) and TSA-1 (amino acids 78-652) were cloned in eukaryotic genetic expression vector CMVI.UBF3/2 as in Example II.

C57BL/6 (B6, H-$2^b$) mice ("B6 mice") are described in Example II. B6 mice (5/group) were immunized twice at an interval of six weeks with antigen (ASP-1, ASP-2 and TSA-1, 1 µg each) encoding vectors with or without IL-12 and GM-CSF expression constructs (33 µg each). Two weeks after the second immunization, mice were challenged with BFT (Brazil strain, 1×$10^5$/mouse) and mortality was recorded daily.

C3H/HeSnJ (C3H, H-$2^k$) mice ("C3H mice") were obtained from Jackson Laboratories (Bar Harbor, Me.) at 6-8 weeks of age. C3H mice (5/group) were injected with CMVI.UBF3/2 containing ASP-1, ASP-2 and TSA-1 with or without cytokines encoding plasmids (33 µg each) as above. The presence of parasite-specific antibodies was assessed by ELISA using sera pooled from individual tail blood samples (5 mice per group) collected 2 weeks after the second immunization. Negative and positive controls were sera from normal mice (NMS) and from mice chronically infected with *T. cruzi* (CMS), respectively. Two weeks after second immunization, animals were infected by intraperitoneal injection with $10^3$ *T. cruzi* BFT. Blood parasite levels were monitored using hemacytometer counts of 10 µl tail-vein blood.

Figure 16A:
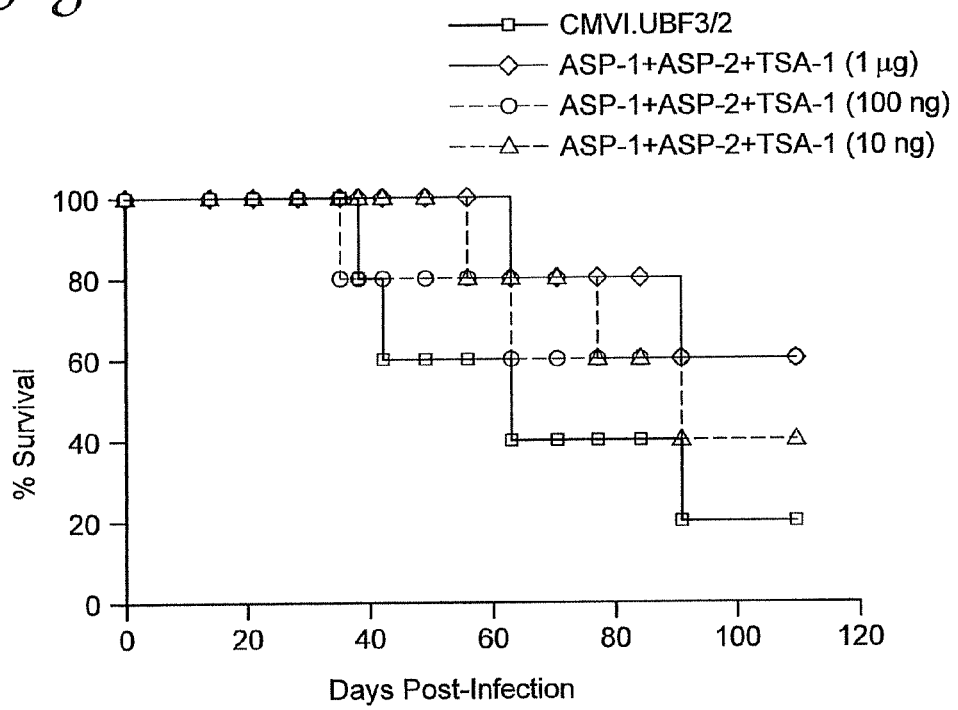
FIG. 16 shows mortality for B6 mice vaccinated with antigen (ASP-1, ASP-2 and TSA-1) encoding vectors (B) with or (A) without cytokines (IL-12 and GM-CSF) expression constructs as a function of days post-infection (dpi).
Figure 16B:
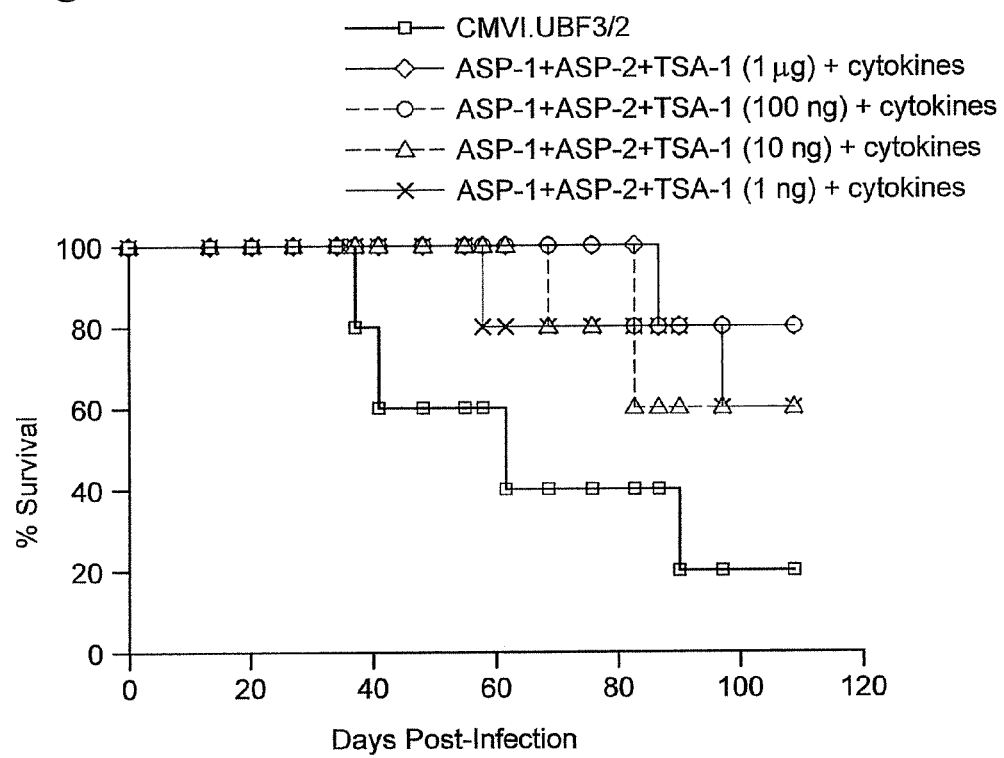
Figure 18:
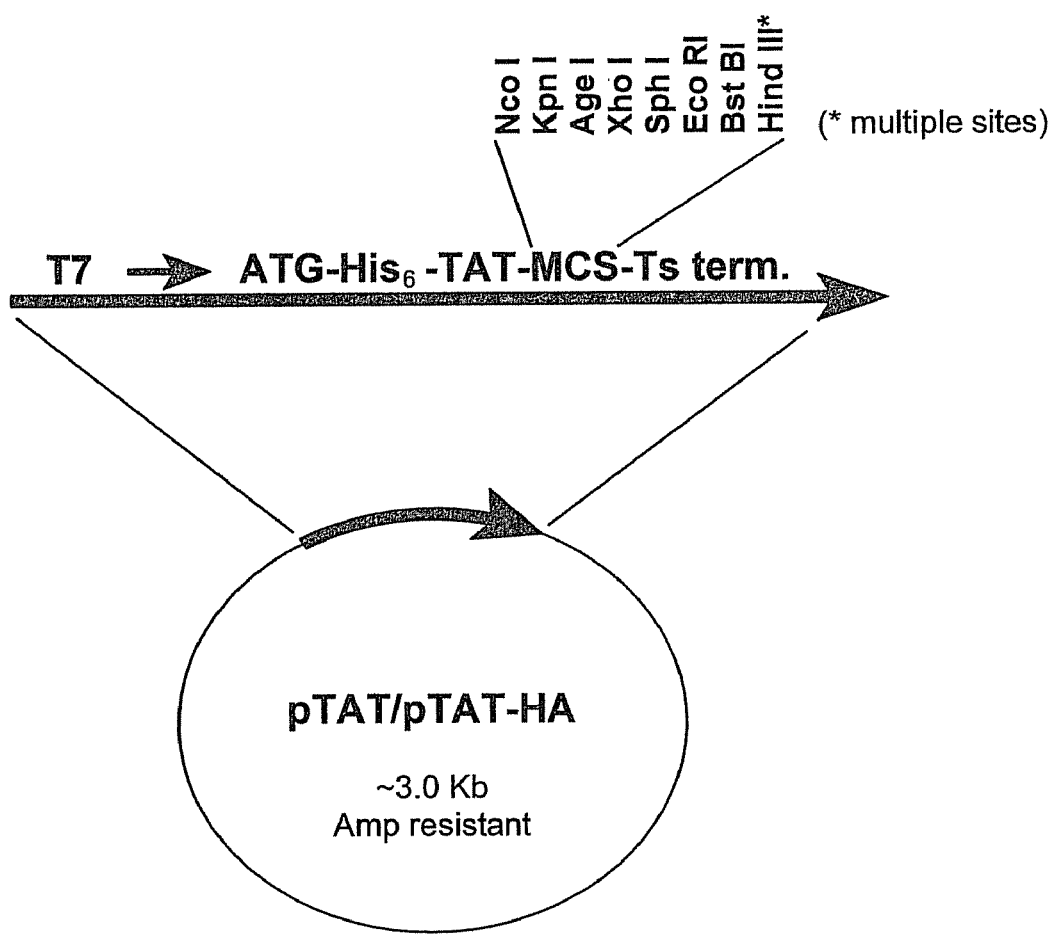
FIG. 18 is a schematic of plasmid pTAT/pTAT-HA used produce polypeptides capable of translocating across mammalian plasma membranes.

Multicomponent vaccine in B6 mice. As described in Example II, B6 mice immunized with CMVI.UBF3/2 containing ASP-1, ASP-2 and TSA-1 genes exhibited moderate levels of *T. cruzi* specific antibodies and antigen-specific CTL activity. When challenged with a lethal dose ($10^5$/mouse) of *T. cruzi* trypomastigotes, all mice immunized with ASP-1, ASP-2 and TSA-1 encoding genes exhibited lower parasitemia levels, and 60% of the mice survived the challenge infection. Of the mice injected with the control vector DNA, 80% succumbed to *T. cruzi* infection (FIG. 16A). However, like immunization with TSA-1 alone (Example I), the three genes together also failed to provide complete protection from *T. cruzi* infection. Immunized mice which survived the challenge infection exhibited varying degrees of inflammation in the heart and/or skeletal muscles, indicative of the persistent infection.

Multicomponent vaccine with cytokine in B6 mice. IL-12 and GM-CSF have shown utility as vaccine adjuvants, and in addition have been shown to be important in controlling disease outcome to *T. cruzi* infection (E. Fontt et al., *Infect Immun.* 66:2722-2727 (1998)), C. Meyer zum Buschenfelde et al., *Clin. Exp. Immunol.* 110:378-385 (1997)). IL-12 and GM-CSF have been reported to enhance both humoral and cellular immune responses (Y. Chow et al., *J. Immunol.* 160:1320-1329 (1998); M. Geissler et al., *J. Immunol.* 158:1231-1237 (1997); K. Irvine et al., *J. Immunol.* 156:238-245 (1996); J. Kim et al., *J. Immunol.* 158:816-826 (1997); Z. Xiang et al., *Immunity* 2:129-135 (1995)). As described in Example II, mice vaccinated with ASP-1, ASP-2 and TSA-1 DNA plus the IL-12 and GM-CSF expression constructs exhibited significantly higher levels of *T. cruzi* specific antibodies and CTL activity compared to mice immunized with antigen encoding expression constructs alone. The enhancement in activation of both humoral and cellular responses by co-injection of cytokines encoding vectors correlated with increased resistance to *T. cruzi* infection, as evidenced by the reduction in blood parasites, tissue parasites and inflammation and increased survival (FIGS. 16A & B).

C3H mice. The ability of genetic vaccines to provide protection from *T. cruzi* infection in another inbred mouse strain (C3H mice) which is more susceptible than the B6 mouse strain to infection with Brazil strain of *T. cruzi* was examined. Immunization of C3H mice with antigen encoding vectors and cytokine expression plasmids resulted in induction of significant levels of anti-parasite antibodies (FIG. 17A). However, when challenged with a lethal dose of BFT (1000/mouse), C3H mice immunized with ASP-1+ASP-2+TSA-1 encoding plasmids with or without IL-12+GM-CSF expression constructs exhibited high parasitemia similar to control mice injected with vector alone (FIG. 17B). All mice succumbed to infection irrespective of vaccination by 39 days post-infection (FIG. 17C).

Summary. Following intramuscular immunization with ASP-1, ASP-2 and TSA-1 expression plasmids, C57BL/6 (B6, H-$2^b$) mice exhibited moderate level of immunity to *T. cruzi* infection, which was significantly enhanced by co-delivery of IL-12 and GM-CSF encoding plasmids. The level of protection correlated with the amount of antigen encoding vectors used for immunization. Despite the successful vaccination of B6 mice, immunization of C3H/HeSnJ (C3H, H-$2^k$) mice with plasmid DNAs expressing ASP-1, ASP-2, TSA-1 with or without IL-12, GM-CSF failed to generate significant protective immunity. It should be noted, however, that C3H mice are extremely susceptible to infection with *T. cruzi* (typically 100% mortality is observed upon initial infection) and thus would have been expected to respond differently. These results do demonstrate that multicomponent genetic vaccines constituted by ASP-1, ASP-2 and TSA-1 are useful for the induction of partial immunity to *T. cruzi* infection, and the minimal amount of each DNA required for elicitation of protection from *T. cruzi* infection is in the range of 0.1-1 µg. The quality and the quantity of immune responses can be enhanced by co-delivery of cytokine expression plasmids. The immune response generated by the three genes in B6 mice was significant, although not sufficient to prevent *T. cruzi* infection or to prevent death from infection in 100% of vaccinated animals.

Example V

Determination of Minimal Plasmid DNA Sufficient to Elicit Immunity

To determine the minimal amount of plasmid DNA sufficient to elicit immunity to *T. cruzi*, mice were immunized with various dilutions of each of CMVI.UBF3/2-ASP-1, -ASP-2 or -TSA-1 genes, (0.001-33 µg/mouse). Co-immunization with up to 10 ng of each gene provided the similar levels of resistance as provided by 33 µg of each gene, though detectable level of CTL responses were generated only in mice immunized with 33 µg of each DNA vaccine. None of these groups of mice exhibited detectable antibody responses. When *T. cruzi* genes were co-delivered with cytokine adjuvants, as little as 1 ng of vaccine DNA resulted in activation of *T. cruzi* specific, MHC class I restricted T cells capable of cytolytic activity, while 10 ng of each DNA was needed to induce the production of moderate levels of antibodies. The degree of reduction in tissue and blood parasite load, the intensity of inflammatory infiltrate in myocardial tissue and the level of resistance to *T. cruzi* infection correlated with the amount of DNA delivered, with the maximum protection being observed with 0.1-33 µg of each vaccine DNA and cytokines. All the mice immunized with 1-33 µg of DNA along with cytokine adjuvants survived a minimum of 90 days post-infection (dpi), in comparison to controls which succumbed to infection as early as 35 dpi.

Example VI

Identification of Immunogenic Polypeptides Using Expression Library Immunization (ELI)

ELI is unbiased with respect to antigen type by putting no constraints on nor making any predictions about antigens which should be good vaccines. ELI is also unbiased with respect to the immune effector mechanism that should be induced to get good protection—DNA vaccines generally elicit both cellular (including CD8$^+$-dependent) and humoral responses and can be designed or delivered to emphasize either or both.

Efficacy of vector pORF.GFP for the selection of ORF-genes. Although we have already constructed a small library of *T. cruzi* genomic DNA in pcDNA3, we are in the process of constructing an ORF library of up to 50,000 clones in ORF-.GFP vector. Screening of the *T. cruzi* genome for protective genes by ELI would be greatly facilitated by the generation of an ORF-library. pORF.GFP has been designed by Johnston et al. (Texas Southwestern Medical Center, TX) for the selection of inserts with long ORF in *E. coli*. An *E. coli* optimized green fluorescent protein (GFP) encoding gene is inserted in pCMVI, 3' to the unique restriction site to be used for cloning of random genomic inserts. A T7 promoter and ATG codon along with Shine-Delgarno sequence is positioned upstream of BamHI site, and a T7 termination sequence is provided downstream of GFP. *E. coli* HMS174 cells which contain T7 polymerase under the control of isopropyl β-D thiogalactopyranoside (IPTG) inducible LacZ promoter are transformed with the recombinant plasmids. T7 polymerase mediates transcription and translation from the insert-GFP fusion genes if insert DNA is present as a continuous open reading frame in fusion with the GFP encoding gene. Inserts which are out of frame or are oriented in reverse and therefore likely to contain stop codons (considering all codons are utilized at equal frequency, 15 stop codons/kb of non-coding DNA can occur) would not read through and express GFP. Two versions of ORF.GFP plasmid that will be used for cloning of the *T. cruzi* genomic DNA are ORF.PA.GFP and ORF.PNA.GFP. Both plasmids contain PacI and AscI restrictions sites surrounding the unique BamH1 (In ORF.PBA.GFP or NarI (In ORF.PNA.GFP) restriction sites for cloning of the random genomic inserts. Genomic DNA digested with Sau3A enzymes can be cloned in pORF.PBA.GFP at the BamH1 site while genomic DNA digested with HpaII, Taq1 or HinPII can be cloned in pORF.PNA.GFP at the NarI.

The fluorescent signal obtained with illumination of GFP expressing bacteria under uv light provides an easy tool for sorting of the recombinants containing ORF-genes. The efficacy of the pORF.PBA.GFP plasmid to provide selection for ORF-genes has been determined by Johnston et al. For this, the bacteria transformed with a yeast or *T. cruzi* genomic library constructed in pORF.PBA.GFP plasmid were induced for GFP expression on LB-agar plates containing 40 μM IPTG and incubated at 30° C. for 2 days. Recombinants which expressed GFP were manually picked by visualization of fluorescent signal obtained upon illumination with long wave uv transilluminator. Sequencing of 50 randomly picked GFP-positive clones from the yeast library and 30 clones from the *T. cruzi* library suggested the presence of ORF in all of the sequenced clones and unbiased representation of the genome (GFP expression was not based upon the insertion of specific group of genes or sequences). Sequencing of these clones also confirmed the incorporation of single insert/clone and the absence of chimeric fusion genes. Thus, we expect that selection of bacteria expressing high levels of inducible GFP-based fluorescence from the library generated with *T. cruzi* genomic DNA in the pORF.GFP vector will provide a representative ORF-library containing most *T. cruzi* genes.

Generation of a *T. cruzi* ORF-library in a eukaryotic expression vector. The ORF.GFP library clones from each 96-well plate are pooled together. Plasmid DNA isolated from the plate pools is digested with PacI and AscI restriction enzymes, separated on 1% agarose gels.0.2 to 1 kB *T. cruzi* genomic DNA fragments are purified and ligated in CMV.UB.PBA vector digested with similar enzymes. The CMV.UB.PBA vector is designed such that the *T. cruzi* genomic DNA inserts are transcribed through strong cytomegalovirus promoter and the translation initiates with a ubiquitin terminal fusion. This vector when used for genetic immunization allows high level production of the fusion protein, and the antigenic protein is targeted to the proteosome for efficient processing and presentation. The *T. cruzi* genomic library in eukaryotic expression vector CMV.UB-.PBA is then screened using the ELI approach for the isolation of individual protective genes.

Generation of "repeat-less" ORF-library. Although high copy, related gene families are in general present in kinetoplastids, the *T. cruzi* genome is especially rich in repeat gene families. The presence of these gene families (e.g. trans-sialidases (TS), mucins, cruzipains, L1Tc repeats etc.) which contain 100 s-1000 s of members sharing high homology could be of particular concern when screening the *T. cruzi* genome for protective genes. If the majority of members of these gene families exhibit protective capability, and are distributed randomly in the 96-well plates containing ORF-library, then we may end up identifying TS or other family members only as protective genes during library screening by ELI. We have already demonstrated that a significant level of protection from *T. cruzi* infection can be generated by immunization with three members (TSA-1, ASP-1, ASP-2) of the TS-gene family (Preliminary Studies). However, 1000 s of trans-sialidase family members, which are not known to have any functional significance are considered to be more susceptible to variation in epitopes and loss among different strains of *T. cruzi* than the house-keeping genes which are evolutionarily more conserved. Therefore, a vaccine constituted of repeat genes may not prove to be as effective against different strains of *T. cruzi* as a vaccine made of low copy, essential conserved genes.

If the presence of repeat genes inhibits our attempts to identify low copy protective genes, we will use a "repeat-less" ORF library (devoid of genes belonging to large gene-families) for screening by ELI. For this, ORF-library clones from 96-well plates will be transferred to nitrocellulose filters, uv cross linked, and hybridized at low stringency with radioactive probes derived from TS family genes (ASP-1, ASP-2 and TSA-1), cruzipain repeats containing conserved sequences, mucin family members containing highly conserved N and C-terminal domains and L1 Tc repeats. Clones identified as members of the large gene families by dot-blot hybridization then will not be included during pooling of clones from ORF-library and "repeatless" ORF-library will be screened by ELI for protective genes.

Evaluation of libraries. The pcDNA3/*T. cruzi* library clones were analyzed for random and complete representation of the *T. cruzi* genome by sequencing 30 random clones. Approximately 40% of the sequences are expected to match the sequences of trypanosomatids or other organisms already in the public databases. Sequence analysis was performed, and suggests that this library does not consist of selective gene family members only, and that non-family members that are present at low copy number in *T. cruzi* genome are represented at the desired frequency. The randomness of the library will be further confirmed by screening ~2000 randomly chosen clones in the library (20×96-well plates) by dot blot hybridization using radio-labeled transialidases, mucins, sires, E1-3 repeats and mini/maxi circles probes. The randomness of the library can be assessed based upon the probability of presence of these genes in *T. cruzi* genome compared to what is found in the library. To determine that majority of the pcDNA3/*T. cruzi* library clones stored in the library contained inserts, 100 clones were analyzed by restriction digestion and PCR amplification. These experiments suggest that ~70-80% clones in the library contain inserts of various sizes (in the range of 200-500 bp).

The ORF-library will likewise be evaluated for representation of the *T. cruzi* genome. 5' and 3' ends of the inserts from 100 randomly picked ORF-clones will be sequenced. Representation of the genome in the ORF-library will also be confirmed by hybridization mapping with $^{32}P$ labeled *T. cruzi* high copy number genes (genes encoding trans-sialidase family proteins, mucins, amastins, tubulins and cruzipain). Hybridization of the ORF-library with low copy number genes (gp72, one copy, glyceraldehyde phosphate dehydrogenase, 2 copies) will confirm the presence of a majority of *T. cruzi* genes in ORF-library. To confirm that the genes cloned in pORF.GFP are expressed in mammalian cells, some of the randomly picked plasmid preparations from individual and mixtures of clones will be transiently transfected in COST cells and the transfectants tested for the expression by immunofluorescent staining with polyclonal anti-*T. cruzi* serum. The lack of GFP expression in mammalian cells will confirm that fusion proteins are not made in eukaryotic cells. This technique has been previously used in our lab to demonstrate the expression of TSA-1, ASP-1 and ASP-2 encoding genes cloned in genetic immunization vectors.

Effect of genetic vaccines on protection and survival from *T. cruzi* infection. The determination of relative efficiency of each sub-library, plate-pool or sets of genes to elicit immune responses and provide protection from *T. cruzi* infection is estimated based upon the quantitation of blood and tissue parasites in the acute phase and survival from infection.

C57/BL6 mice were immunized twice at an interval of 6 weeks with pcDNA3 vector only, or with a plate pool of pcDNA3/*T. cruzi* library clones (96 clones, ~1 μg each) with/or without IL-12 and GM-CSF cytokine adjuvants (10 μg each). Mice immunized with ASP-1+ASP-2+TSA-1 (1 μg each)+IL-12+GM-CSF (10 μg each) were used as positive control. Mice were challenged with 100,000 BFT of *T. cruzi* (Brazil) two weeks post-immunization, and observed for survival from infection. It was observed that 60% of the mice (3 out of 5) immunized with pcDNA3 library pool with or without cytokine adjuvants, and 80% mice (4 out of 5) immunized with a mixture of ASP-1+ASP-2+TSA-1 (1 μg each)+IL-12+GM-CSF survived *T. cruzi* infection at least 80 days post-infection while all mice injected with control vector (pcDNA3 only) succumbed to *T. cruzi* infection by 65 days post-infection. These results suggest that elicitation of protective immune responses by immunization of mice with pools of 96 clones is feasible.

The Brazil strain of *T. cruzi* is used for infection studies because the infection and disease development in various mouse strains this strain is well characterized. Screening of SylvioX10/7 ORF-library for protective genes using Brazil strain for infection will also provide evidence for cross-strain protection. To analyze the ORF.GFP vector library, BALB/cByJ mice (Jackson laboratories) will be used for these studies. These mice exhibit an intermediate resistance to *T. cruzi* (Brazil strain) depending upon the number of infectious trypomastigotes of the Brazil strain injected. 80-100% mice infected with $5\times10^4-1\times10^5$ blood-form trypomastigotes succumb to infection within 30-50 days post-infection.

Bacterial clones obtained from subcloning of pools of inserts into CMV.UB.PBA vector will be amplified on LB-agar plates overnight at 37° C. This will assure the growth of slow growing bacterial clones which are overtaken by fast growing clones when cultured together. Bacterial cultures from each agar plate will then be harvested in a total of 15 mL LB and plasmids purified using EndoFree Plasmid Maxi Kit (Qiagen) and Procipitate (LigoChem Inc). DNA will be injected in the quadriceps muscle of mice (6/group). Use of endotoxin-free plasmid DNA will ensure that immune responses are not induced due to injection of bacterial lipopolysaccharides (potent inflammatory agents). Mice will be immunized twice at a 45 day interval (we have found this interval to be optimum for induction of immune responses and protection from *T. cruzi* infection in previous studies. Mice injected with the vector alone or CMVI.UBF3/2.ASP-2 will be used as negative and positive controls, respectively.

Two weeks following the second immunization, mice will be challenged with a lethal dose ($10^5$/mouse) of BFT of the Brazil strain of *T. cruzi* by intraperitoneal injection. The efficacy of each pool of genes to provide protection from *T. cruzi* infection will be evaluated by the following parameters:

(i) Parasitemia: Parasitemias in tail vein blood will be monitored at weekly intervals by microscopic counting of trypomastigotes present in blood and/or estimating the luciferase activity in transfectant *T. cruzi* in blood using standard techniques. The parasite counting technique is time consuming and is also limiting in sensitivity and accuracy because it often misses significant numbers of amastigotes that are present in circulation. Because of these drawbacks, we have recently developed the *T. cruzi* transfectants expressing fire-fly luciferase and have adapted methods for the rapid detection of luciferase activity and thus parasite number in blood.

Luciferase expressing Brazil strain transfectants were generated by the introduction of the firefly luciferase reporter vector pHD421 Bner into epimastigotes of *T. cruzi* Brazil strain by electroporation. pHD421Bner is a derivative of the trypanosome expression vector pHD421 in which the *T. brucei* tubulin sequences were replaced with the *T. cruzi* beta tubulin sequences to allow targeted integration into the *T. cruzi* genome by homologous recombination. Additionally, the native 5' UR. of the luciferase gene was replaced with the expression enhancer sequence ner-ACC (1) at the −1 position. Transfectant epimastigotes were selected in the presence of hygromycin (1 mg/ml) and luciferase activity is estimated using Promega's Luciferase Assay System and a Tropix Luminometer.

(ii) Histological detection of tissue parasites: Although parasitemia provides a quick and relatively easy measure of resistance to infection, parasite level is not a good prediction of survival. To obtain a second measure of parasite control, quantitation of the parasite load in various tissues of immunized/infected mice during the acute phase of infection (30-50 days post-infection) will be used to determine the ability of genetic immunization to control the infection. For this, one mouse from each group will be sacrificed 30 days post-infection, and heart, liver, kidney, spleen and skeletal muscle tissue will be collected. Tissues will be fixed with 10% formalin, dehydrated in absolute ethanol, cleared in xylene and embedded in paraffin. Five micron thick sections will be cut and stained with hematoxylin & eosin and analyzed using light microscopy. Tissue sections will be examined in a blinded fashion and scored according to extent of tissue parasitism.

(iii) Survival from infection: Mortality will be recorded daily.

We believe that evaluation of infected mice to control the *T. cruzi* infection based upon the above parameters will provide a relatively easy and quick estimation of the efficacy of genetic vaccines.

Characterization of inserts mediating protection. We are aiming at identification of 20-50 protective genes by screening of ORF-library by ELI. Though full characterization of these genes during the course of this project will not be possible, attempts will be made to determine the function of these genes based upon following parameters:

(i) End sequencing: The genes identified based upon their capability to generate protection from *T. cruzi* infection will be sequenced at the 5' and 3' ends using vector specific oligonucleotide primers. Based upon results from the sequencing of trypanosomatid genes, we expect to find homologues for ~40% of the inserts present in sequenced plasmids. We will fully sequence those genes for which no homology is found among sequences in the public databases. The presence of the N-terminal signal sequence, COOH-terminal cleavage and GPI-anchor addition signal sequence, hydrophobic regions or other motifs will be used to help determine the identification, function and localization of these gene products.

(ii) Cloning of complete gene: It is likely that many of the protective ORF-clones will not contain complete genes. Because we plan to identify 20-50 genes, attempts to recover full genes will be done for very few of the protective inserts. Those for which full genes might be sought would include inserts in plasmids that yield very high levels of protection but which appear from sequence information to be incomplete and for which the available sequence provide no clue as to the identity or function of the encoded gene products. Under these situations, we would use gene splicing by overlapping extension (SOE) PCR (successfully used by us to obtain the full sequence of ASP-2 gene) for identification and cloning of the complete gene.

(iii) Functional characterization: Functional analysis will be done for only a few of highly protective ORF-clones for which complete genes are identified. To produce the antibodies against these selected gene products, mice (3/gene) will be immunized with the genetic vaccine along with the GM-CSF encoding plasmid (33 μg each DNA/mouse) twice at an interval of 45 days. We have successfully used this protocol to produce anti-ASP-I, ASP-2 and TSA-1 antibodies. Staining of the permeabilized and unpermeabilized parasites (epimastigotes, trypomastigotes and amastigotes) with antibody and visualization by confocal microscopy will determine the stage of expression as well as localization of the protein. Western blotting of the cell lysate from three developmental stages of *T. cruzi* with the antibodies will also confirm the stage of expression and size of the proteins encoded by those genes. Scanning of the microarrays for genes upregulated in different developmental stages might provide some information about stage specific expression of some of the protective genes identified by ELI.

Effect of genetic immunization on parasite burden during the chronic phase of *T. cruzi* infection. To determine if genetic immunization decreases the disease severity in chronic stage of infected mice, mice which survive infection following genetic immunization will be examined for tissue parasite load and for the presence of inflammation. Surviving mice at >120 days post-infection will be compared to control mice injected with empty vector DNA alone, and challenged with 1000 trypomastigotes (a majority of the control mice infected with this low dose of *T. cruzi* will be able to control the acute infection and survive into the chronic phase of chagasic myocardiomyopathy). Mice will be sacrificed during chronic phase of *T. cruzi* infection and analyzed for parasite load and for the severity of disease.

These experiments will assess the effect of immunization on blood parasite load. However, the level of parasites in the blood does not always correlate with the tissue parasite load. Also, once the chronic phase of infection is reached, detection of parasites by standard histological approaches is very difficult. Therefore, the effect of immunization on the parasite burden in the heart and skeletal muscles of mice will be assessed by more sensitive techniques and compared to parasite load in unvaccinated/infected control group mice.

(i) Enzymatic estimation of luciferase activity in various tissues: The *T. cruzi* Brazil strain parasites to be used for challenge infection in these studies is transfected with a gene encoding cytoplasmic luciferase (LUC). These transfectants express a very high level of luciferase activity which can be estimated by fairly easy and standard methods (described above). We are already using these transfectants for sensitive and accurate determination of parasite levels as compared to microscopy counting in vitro infection studies. To determine the effect of immunization with pools from ORF-library on the parasite burden in heart and skeletal muscles of infected mice, one mouse from each surviving group will be sacrificed and proteins from heart tissue and skeletal muscles will be extracted and quantitated for luciferase activity using kits supplied by Promega. Comparison of the specific enzyme activity from immunized/infected mice to control infected mice will then determine the effect of immunization in controlling the tissue parasite burden. Number of parasites in a specific tissue will be calculated by reference to a standard curve.

(ii) Competitive PCR: To quantitate the effect of immunization on tissue parasite load, total DNA isolated from various organs of the infected mice will be used as template for competitive PCR. PCR will be carried out using *T. cruzi* kDNA specific oligonucleotides 5'-GGTTCGATTGGGGTTGGTGTAATATA-3' (SEQ ID NO:16) and 5'-AAATAATGTACGGGT/GGAGATGCATGA-3' (SEQ ID NO:17) as forward and reverse primers respectively to amplify a 330 bp fragment. Plasmid pBSKILL containing 442 bp fragment of IL-2 gene (57-497 bp) as stuffer fragment flanked by kDNA specific sequences will be used as competitor for performance of quantitation by competitive PCR.

(iii) Detection of *T. cruzi* by in situ PCR: In situ PCR amplification of *T. cruzi* minicircle kinetoplast DNA (kDNA) has been used to detect parasites or parasite derived DNA in infected tissue. The high sensitivity of this procedure is enhanced by the fact that each parasite has 5-10,000 copies of minicircles, and each minicircle has 4 copies of conserved regions, which are to be used as targets for PCR amplification of kDNA. If parasites can not be detected in immunized mice by enzymatic and competitive PCR techniques, then further confirmation of clearance of parasites and cure from disease will be done by monitoring the presence of parasites in tissues of the mice by in situ PCR. Tissues from the heart or skeletal muscle of infected mice will be processed, sectioned and fixed as previously described (60). kDNA-specific oligonucleotides 5'-GGTTCGATTGGGGTTGGTGTAATATA-3' (SEQ ID NO:18) and biotin-labeled 5'-AAATAATG-TACGGGT/GGAGATGCATGA-3' (SEQ ID NO:19) as forward and reverse primers will be used for amplification by PCR. PCR products will be detected with avidin-peroxidase and color developed with 3',3'-diaminobenzidine tetrahydrochloride. Sections will be counter-stained with hematoxylin and visualized by light microscopy. At least 200-microscopic fields from different sections of the heart and skeletal muscles tissue of mice will be screened for the presence of parasites. Comparison of the number of parasitic foci in tissue from immunized/infected mice to control infected mice will determine the effect of immunization in controlling the tissue parasite burden.

Effect of genetic immunization on disease severity. Based upon our previous studies, we expect that a reduction in acute phase parasitization and chronic parasite load will correlate with a reduction in inflammatory disease. To determine the quantitative effect of immunization with pools or sets of genes from ORF-library on disease severity in chronically infected mice, techniques well standardized in our laboratory will be used. Heart and skeletal muscle tissue from immunized/challenged mice will be fixed, embedded in paraffin, and five micron sections stained with hematoxylin and eosin will be analyzed using light microscopy. Tissue sections from mice infected without vaccination will be used as control. Tissue sections will be scored from 0 to 4 in blind studies according to the extent of tissue damage from normal to total wall involvement.

Example VII

Identification of Immunogenic Polypeptides Using DNA Microarray Technology

DNA microarrays provide the means to monitor the expression of many or all genes in a genome, under different growth conditions, during different developmental stages, or in different tissues. This technology will be used to identify genes whose expression is upregulated in *T. cruzi* during the intracellular amastigote stage of the infectious cycle, soon after infection of the host cell. This focus is based upon the reasoning that the protein products of such genes would be among the first to reach the class I MHC processing and presentation pathway and thus would serve as early indicators to the immune system of the infection status of host cells. We believe that amastigote target antigens are part of the "missing link" for vaccine development in *T. cruzi*. We showed in Example II that the $CD8^+$ T cell population, the primary role of which is to recognize and kill host cells harboring intracellular pathogens, is very important for immune control of *T. cruzi*. Furthermore, we showed that transfer of *T. cruzi*-specific $CD8^+$ T cell lines, or immunizations which induce parasite-specific $CD8^+$ T cell responses to amastigote-expressed proteins, are protective in murine models of *T. cruzi* infection.

Scanning and arraying equipment. An microarrayer based on the design, plans, and software made available by the Pat Brown lab group at Stanford University (http://cmgm.stanford.edu/pbrown/) will be constructed, and a scanner from Genetic Microsystems will be purchased. Arrays are hybridized with fluorophore-labeled cDNA as described below, scanned, and the data from a complete scan is reconstructed to yield a pseudoimage (usually a TIFF image).

Production of DNA for arraying. The 20,000 member clonal ORF library obtained as described in Example VI will be used to prepare the DNA to be arrayed. PCR products from various DNAs can be spotted onto slides. Alternatively, whole plasmid DNA purified from the 20,000 clones can be used directly for the production of microarrays, thus saving the considerable time and expense of the 20,000 PCR reactions. Each microarray will contain a number of positive and negative controls. Positive controls will include genes known to be developmentally regulated in *T. cruzi*, including amastin, porin and gp72 to represent amastigote, trypomastigote and epimastigote expressed genes, respectively. *T. cruzi* genes for which we expect a relatively stable level of expression in the different life cycle stages include actin, tubulin, and GAPDH. The pORF.GFP vector without inserts and murine cDNA encoding cytokine genes will also be included as negative controls. The control DNAs to be included in the arrays will be produced by PCR using sequence specific primers and genomic or plasmid DNA as template.

Spotting of DNAs in microarrays. Detailed protocols for most steps in the process are readily available in the literature (J. DeRisi et al., *Nat. Genet.* 14:457-460 (1996); J. DeRisi et al., *Science* 278:680-686 (1997)). Slides are normally prepared using silanization or by coating with poly-L-lysine. The arrays will be probed with cDNAs isolated from *T. cruzi* at different stages of development.

Sources of cDNA for screening. Synchronized cultures of parasites at different time points during conversion from trypomastigotes to amastigotes will be obtained by acid induction of conversion of freshly derived trypomastigotes or by harvesting Vero cells to which freshly isolated trypomastigotes have been added for various periods of time. Initially, we will isolate mRNA from parasites or parasite-infected host cells at one or two time points in the infection/conversion process, time 0 (immediately upon addition of trypomastigotes to host cells or just prior to exposure to acid in the case of the acid-conversion protocol), 12 hours and 24 hours post-infection/induction. Infective trypomastigotes not more than 2 hours post-release from heavily infected Vero cells cultured in T-75 flasks will be collected as "synchronized" trypomastigotes.

Production of labeled cDNAs. Brazil strain *T. cruzi* trypomastigotes from monolayers of Vero cells at 37° C. in a 5% $CO_2$ atmosphere will be harvested by centrifugation of culture supernatants at 1,500×g for 10 minutes at room temperature. Fresh T500 flasks containing semi-confluent monolayers of Vero cells will be infected with 20 trypomastigotes per cell (approximately $2.3\times10^8$ parasites) and total RNA isolated immediately (to provide the baseline mRNA expression levels) or the cultures rinsed after 2 hours to remove non-infecting parasites and the mRNA isolated at 12 or 24 hours post infection. Alternatively, amastigotes will be obtained by acid treatment of trypomastigotes: freshly harvested cell culture trypomastigotes are resuspended at $5\times10^6$/ml in DMEM containing 0.4% BSA (DMEM-BSA) buffered with 20 mM MES, pH 5 and incubated at 37° C. in 5% $CO_2$ for 0 (and harvested for baseline mRNA) or after 4 hours, centrifuged and resuspended in bicarbonate-buffered DMEM-BSA, pH 7.5 and incubated for another 8 or 16 hours at 37° C. in 5% $CO_2$.

Total RNA is isolated by adding 5 mL of Ultraspec™ II RNA reagent (Biotecx Laboratories, Inc. Houston, Tex.) directly to each washed flask and the resulting lysate is passed repeatedly through a pipette before being transferred to a 10 ml polypropylene tube. The homogenate is held on ice for 5 minutes to allow the dissociation of ribonucleoprotein complexes. Total RNA is extracted by the addition of 1 ml chlorofolin. After vortexing for 15 sec, the sample is centrifuged at 12,000×g for 15 minutes at 4° C. The aqueous phase (2.5-3.0 ml) is transferred to 1.5 ml polypropylene microcentrifuge tubes, 0.5 vol of isopropanol is added, and the tubes are vortexed. To bind the RNA, 0.05 vol of RNATack™ resin (Biotecx Laboratories) is added and mixed by vortexing for 30 sec. The tubes are spun for 1 minute in a microcentrifuge. The supernatant fluid is discarded and the pellet is washed twice with 75% ethanol. The pellet is dried briefly under vacuum to remove any traces of ethanol and resuspended in 0.1 vol of diethylpyrocarbonate (DEPC) treated water. After a brief spin to pellet the resin, the supernatant RNA is transferred to a fresh tube and quantitated by UV spectrophotometry. Approximately 300-400 ug of total RNA is obtained from one T500 flask. The method of total RNA isolation from axenically induced amastigote forms is essentially the same except that the parasites are harvested by centrifugation and the pellet is resuspended directly in Ultraspec™ reagent at a density of $1 \times 10^8$ cells per ml.

Labeled first strand cDNA is synthesized from the total RNA samples using Superscript™ II reverse transcriptase (BRL Life Technologies) and CyDye labeled fluorescent nucleotides (Cy3-dUTP and Cy5-dUTP, Amersham Corp.). In a sterile 0.5 ml microfuge tube first strand buffer, oligo d(T)12-18, 10× low T dNTP mix, Cy3 or Cy5-dUTP (1 uM), DTT, Rnasin, and total RNA are added. The tube is incubated at 65° C. for 5 minutes and cooled to 42° C. Two microliters (400U) of Superscript™ II enzyme are added and the reaction is held at 42° C. for 25 min. Another 2 ul of enzyme are added, and the reaction is incubated for 35 minutes at 42° C. The reaction is stopped by the addition of 5 ul of 500 mM EDTA. To hydrolyze residual RNA, 10 ul of 1 M NaOH are added and the sample is incubated at 65° C. for 1 hour. The sample is cooled to 25° C. and 25 ul of 1 M TrisHCl, pH 7.5 are added to neutralize the NaOH. The entire labeled sample is transferred to a Microcon-30 microconcentrator (Amicon) and centrifuged at 14,000 rpm in a microfuge until the volume is reduced to 20 ul.

Hybridization of arrays. Hybridization of the labeled cDNAs with the microarrays is done in custom-made hybridization chambers (design and CAD drawings available from the Brown web page or completed units can be purchased from TeleChem). The chambers are loaded with 5.0 µl of hybridization buffer (to maintain conditions of 100% humidity in the cassette chamber thus preventing evaporation of the hybridization solution) prior to addition of the array slide. Approximately 10 µl of hybridization solution containing the fluorophore-labeled cDNAs are added to the array on the slide and a coverslip placed. Standard hybridization buffers for microarray experiments contain 5×SSC and 0.2% SDS. The hybridization chamber is then sealed and immersed in a hot water bath (37° C.-70° C.) for 2-24 hours, depending on the specific application. Long hybridization times and low incubation temperatures under high salt conditions are used to favor the annealing of low copy number sequences. Following the hybridization, the slides are removed from the hybridization cassette and rinsed in 0.2×SSC with and then in 0.2× SSC without SDS, dried and scanned.

Data interpretation. To determine the genes that are upregulated during the conversion of trypomastigotes to amastigotes, we will cohybridize an array with Cy3-labeled trypomastigote-derived cDNA and Cy5-labeled amastigote-derived cDNA. The relative green/red signal for each gene will then be determined for each spot on the array and the spots showing a relative increase in the Cy5 (red) over Cy3 (green) identified. In this case, we would expect the majority of spots in the array to exhibit a 1:1 ratio of red:green, indicating a stable level of expression in the two life cycle stages. Spots showing a significant change from this ratio (>2:1) indicate upregulation in the amastigote stage relative to the trypomastigote stage and will be selected for further study. This level of sensitivity of change in expression level has been achieved in multiple other studies using equipment and conditions similar to those described herein. To assure that the change in expression level observed in the initial analysis is real, the hybridization will be repeated with the dyes "switched" on the two cDNA probes (i.e. Cy3-labeled amastigote-derived cDNA and Cy5-labeled trypomastigote cDNA). The change in expression on stage conversion will also be monitored by comparison of the 12 hour and 24 hour amastigote samples.

Clone sequencing and gene identification. Clones identified as being upregulated in the amastigote stage of the *T. cruzi* life cycle will be identified, and those with the greatest relative increase in expression selected as described above for further study. Up to 200 of the most highly upregulated clones will be end-sequenced (at the UGA Molecular Genetics Instrumentation Facility) for gene identification purposes. Clones containing ORFs for which no homologues can be identified based on the clone-end sequencing will be fully sequenced. Using the complete sequence information we will then conduct additional homology searches in an attempt to establish the identity or putative function of the gene products. We will attempt a reasonably exhaustive electronic analysis of each protein sequence, following a standard set of protocols (e.g., identification of repeats, signal sequences, GPI anchor addition sites or transmembrane regions, domains, cluster analysis of homologues, etc. Based on the results of these determinations, a subset of these clones will be further investigated for protective function. Novel genes of unknown function or with probable function which is consistent with service as good vaccine candidates will be tested individually for the ability to confer resistance to infection in a murine model of *T. cruzi* infection, as described in previous Examples. This work will be facilitated by the fact that the genes will already be in a vector appropriate for DNA vaccination and thus no recloning of the inserts will be required.

Example VIII

Production of a Targeted Polypeptide for Use in Protein Vaccine Against *T. cruzi* Infection and Disease In this experiment, proteins are transduced at high efficiency into cells. For efficient transduction, the transducing substrates are processed such that they are capable of unfolding to traverse the bilipid membrane as a linear protein, in accordance with the method of S. Schwarze et al. (*Science* 285:1569-1572 (1999); H. Nagahara et al., *Nature Med.* 4:1449-1452 (1998)). For example, Schwarze et al. report the delivery of biologically active TAT fusion protein to a mouse (*Science* 285:1569-1572 (1999)). Thus, proteins capable of highly efficient transduction are characterized as being unstable (high free energy, ΔG), misfolded and aqueous soluble. In many cases, shock folding from urea to aqueous on the ionic exchange column increases biological effect of some/most proteins 5-10 fold vs. dialysis. Dialysis, however, can be used as an alternative if desired or necessary.

The pTAT-produced proteins are typically completely insoluble (>99%) and are therefore stored in the inclusion bodies. This not only leads to high yields but safekeeping of the fusion proteins from the host proteases. Shock-misfolding of the protein preferably takes place on the Mono-Q/S and only requires the presence of TAT on the surface of the protein, not on a correctly folded protein. TAT proteins are thought to transduce into cells in a linear array and then are likely refolded and/or degraded by Hsp90 once inside the cell.

Buffers. Buffer Z=8 M urea/100 mM NaCl/20 mM HEPES (pH 8.0); Buffer A=50 mM NaCl/20 mM HEPES (pH 8.0) or (pH 6.5); Buffer B=1 M NaCl/20 mM HEPES (8.0) or (pH 6.5).

Cloning into pTAT. cDNA encoding *T. cruzi* Lyt1 (porin; FIG. 19; SEQ ID NO:20) and TSA-1 was cloned into a polylinker of pTAT or pTAT-HA (obtained from S. F. Dowdy, Washington University) via restriction enzymes or PCR. The TAT protein of HIV is known to cross cell membranes. The plasmid pTAT contains the TAT protein transduction domain and is used to produce urea-denatured genetic in-frame TAT fusion proteins (H. Nagahara et al., *Nature Med.* 4:1449-1452 (1998)). pTAT is an N' terminal fusion so translation terminations in the 5' UTR of cDNA were removed. The ATG in the NcoI site is in-frame.

pTAT Linker:

```
     NcoI        KpnI AgeI
TCC ACC ATG GCC GGT ACC GGT CTC      (SEQ ID NO: 21)
 G   S   T   M   A   G   T   G   L   (SEQ ID NO: 22)

SphI      Eco    BstBI HindIII
GAG GTG CAT GCG GTG AAT TCG AAG CTT
 E   V   H   A   V   N   S   K   L
``` followed by 20 amino acids to TAA Ts termination codon.

pTAT-HA Linker:

The HA tag (underlined), flanked by glycine residues, was inserted into the NcoI site of pTAT. The N' NcoI site has been inactivated.

```
CC ATG TCC GGC TAT CCA TAT GAC GTC   (SEQ ID NO: 23)
    M   S   G   Y   P   Y   D   V    (SEQ ID NO: 24)

CCA GAC TAT GCT GGC TCC ATG-
GCC . . .
 P   D   Y   A   G   S   M   A
```

The ligated plasmid was transformed into a high copy number *E. coli* strain BL21. Supercoiled pTAT-cDNA "X" was transformed into BL21(DE3)LysS strain (Novagen). Six to ten colonies were pulled for 1 ml overnight culture and IPTG was added. Bacteria were centrifuged at 5000×g for 5 minutes at room temperature, the resuspended into approximately 300 ul 2×SDS sample buffer. The mixture was boiled and loaded onto two SDS-PAGE gels along with a negative control strain. After electrophoresis, one gel was stained with Coomassie Blue and transferred, while the other was probed with anti-HA or cDNA-specific antibody. Although the pTAT leader is approximately 3.5 kD, proteins typically migrate 5-10 kDa larger than their predicted fusion protein size on SDS-PAGE. High producing bacterial clones were identified, and glycerol stocks of the clones were made.

pTAT protein purification. 1 L of media was inoculated with 100-200 ml overnight culture of BL21 cells containing the pTAT-cDNA "X" plasmid of interest, and IPTG was added. The culture was rotated for about 4-6 hours at 37° C. Cells were centrifuged at 5000×g for 5 minutes, the cell pellet was washed with ~50 ml PBS(−) and centrifuged again. The pellet was resuspended in 10 ml of buffer Z (8 M urea/100 mM NaCl/20 mM HEPES [pH 8.0]), then sonicated on ice 3×15 second pulses or until turbid. The mixture was clarified by centrifugation at 12,000×g for 10 minutes at 4° C. The supernatant brought to about 10-20 mM imidazole and added at room temperature to a pre-equilibrated 3-10 ml Ni-NTA (Qiagen) column in buffer Z plus 10-20 mM imidazole. The flow was allowed to proceed by gravity or slight air pressure was applied via syringe as required. The flow-through (FT) was collected. The column was then washed with approximately 50 ml buffer Z plus 10-20 mM imidazole. The His-TAT-X protein was eluted by step-wise addition of 5-10 ml each 100, 250, 500, 1 M imidazole steps in buffer Z. Fractions containing the protein were identified via SDS-PAGE or immunoblot using the 12CA5 antibody (anti-HA; Babco) and pooled. Proteins that did not bind at 10-20 mM imidazole, were passed through a second time at 5, 2 or 1 mM imidazole.

Ion exchange chromatography. Ion exchange chromatography was carried out on a 30 micron 10-40 ml ionic exchange column was packed with Resource Q resin (Pharmacia). The HIS-TAT-X protein was loaded onto the column by syringe injection. The column was washed with approximately 40 ml buffer A, and the protein was eluted with a single step of 1 M NaCl. Fractions containing the protein were pooled and desalted on a PD-10 disposable G-25 Sephadex gravity column (Pharmacia) in HEPES (7.2) or PBS(+).

Basic proteins require a Mono S column compared with acidic proteins outlined above. The leader sequence confers a more basic nature to the fusion proteins. The amount of protein purified will dictate the column size required. Further, if the protein binds the Q resin at 8.0 but does not release with 1 M NaCl, the pH is reduced by 0.5 units until it still binds and is not present in the flow through and elutes with a high yield. In some cases proteins bind a Q resin at pH 6.5 and 7.0. Alternatively, one can start with an S resin at pH 6.5 and move up 0.5 pH units as required.

Whether purified by dialysis or ionic exchange chromatography, aliquots of ~250 ul were flash frozen in 10-15% glycerol on dry ice/liquid. $N_2$ and store at −80° C.

Cellular analyses. About ~5-25 ug of protein was labeled with FITC (Molecular Probes cat. #F-1906) in 300 ul, 2 hour, room temperature in the dark, following manufacturer's instructions. The labeled protein was then injected into a gel filtration column (S-12, S-6, S-200) in PBS or a PD-10 column (Pharmacia). Fractions containing purified labeled protein were collected and pooled. About 100-400 ul of purified TAT-FITC fusion protein was added to ~1×10$^6$ cells in media/ FBS (nonadherent cells are best experimentally), and transduction was evaluated at t=0', 15', 30', 45', 60' on FACS (FL-1). The cells were analyzed directly in media or fix in 4% paraformaldehyde. The fixed cells are used for microscopy. Essentially 100% of the cells demonstrated intracellular localization of the protein.

The complete disclosures of all patents, patent applications including provisional patent applications, and publications, and electronically available material (e.g., GenBank amino acid and nucleotide sequence deposits) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

What is claimed is:

1. A multicomponent vaccine comprising a plurality of isolated polypeptides, wherein each polypeptide is a *Trypanosoma* polypeptide comprising a glycosylphosphatidylinositol anchor attachment site, or an immunogenic fragment of said *Trypanosoma* polypeptide; wherein administration of the vaccine is effective to treat or prevent *Trypanosoma* infection in a mammal.

2. The multicomponent vaccine of claim 1 wherein the *Trypanosoma* is *T. cruzi*.

3. The multicomponent vaccine of claim 1 wherein the polypeptide is a member of the trans-sialidase family of proteins.

4. The multicomponent vaccine of claim 2 wherein the polypeptide is expressed in a *T. cruzi* amastigote.

5. The multicomponent vaccine of claim 4 wherein the polypeptide is selected from the group consisting of TSA-1, ASP-1 and ASP-2.

6. The multicomponent vaccine of claim 1 comprising at least ten polypeptides.

7. The multicomponent vaccine of claim 1 which stimulates at least one immune response in a mammalian host selected from the group consisting of an antibody response and a cell-mediated immune response.

8. The multicomponent vaccine of claim 7 which stimulates at least one of a Th1-biased $CD4^+$ T cell response or a $CD8^+$ T cell response.

9. The multicomponent vaccine of claim 8 which stimulates a $CD8^+$ T cell response.

10. The multicomponent vaccine of claim 7 which stimulates an antibody response, a Th1-biased $CD4^+$ T cell response and a $CD8^+$ T cell response.

11. The multicomponent vaccine of claim 1 wherein the polypeptide comprises a membrane translocating sequence.

12. The multicomponent vaccine of claim 11 wherein the membrane translocating sequence is derived from HIV TAT protein.

13. The multicomponent vaccine of claim 1 further comprising a pharmaceutically acceptable carrier.

* * * * *

SEQUENCE LISTING

<160> NUMBER OF SEQ ID NOS: 24

<210> SEQ ID NO 1
<211> LENGTH: 8
<212> TYPE: PRT
<213> ORGANISM: Trypanosoma cruzi

<400> SEQUENCE: 1

Val Asp Tyr Asn Phe Thr Ile Val
1               5

<210> SEQ ID NO 2
<211> LENGTH: 8
<212> TYPE: PRT
<213> ORGANISM: Gallus gallus

<400> SEQUENCE: 2

Ser Ile Ile Asn Phe Glu Lys Leu
1               5

<210> SEQ ID NO 3
<211> LENGTH: 34
<212> TYPE: DNA
<213> ORGANISM: Artificial Sequence
<220> FEATURE:
<223> OTHER INFORMATION: forward primer

<400> SEQUENCE: 3
agtcgacgga tccatgattg catttgtcga aggc                               34

<210> SEQ ID NO 4
<211> LENGTH: 35
<212> TYPE: DNA
<213> ORGANISM: Artificial Sequence
<220> FEATURE:
<223> OTHER INFORMATION: reverse primer

<400> SEQUENCE: 4
atctagaagc ttcatagttc accgacactc agtgg                              35

<210> SEQ ID NO 5
<211> LENGTH: 35
<212> TYPE: DNA
<213> ORGANISM: Artificial Sequence
<220> FEATURE:
<223> OTHER INFORMATION: reverse primer

<400> SEQUENCE: 5
atctagaagc ttcatgccgc agcatttgct ccccc                              35

<210> SEQ ID NO 6
<211> LENGTH:
<212> TYPE:
<213> ORGANISM:

<400> SEQUENCE: 6

000

<210> SEQ ID NO 7
<211> LENGTH: 8
<212> TYPE: PRT
<213> ORGANISM: Trypanosoma cruzi

<400> SEQUENCE: 7

```
Val Asn His Arg Phe Thr Leu Val
1               5

<210> SEQ ID NO 8
<211> LENGTH: 8
<212> TYPE: PRT
<213> ORGANISM: Trypanosoma cruzi

<400> SEQUENCE: 8

Val Asn His Asp Phe Thr Val Val
1               5

<210> SEQ ID NO 9
<211> LENGTH:
<212> TYPE:
<213> ORGANISM:

<400> SEQUENCE: 9

000

<210> SEQ ID NO 10
<211> LENGTH: 28
<212> TYPE: DNA
<213> ORGANISM: Artificial Sequence
<220> FEATURE:
<223> OTHER INFORMATION: forward primer

<400> SEQUENCE: 10
aggatccatg attgcatttg tcgaaggc                                     28

<210> SEQ ID NO 11
<211> LENGTH: 30
<212> TYPE: DNA
<213> ORGANISM: Artificial Sequence
<220> FEATURE:
<223> OTHER INFORMATION: reverse primer

<400> SEQUENCE: 11
aaagcttcat agttcaccga cactcagtgg                                   30

<210> SEQ ID NO 12
<211> LENGTH: 26
<212> TYPE: DNA
<213> ORGANISM: Artificial Sequence
<220> FEATURE:
<223> OTHER INFORMATION: forward primer

<400> SEQUENCE: 12
aagatcttgt ggaaaggaat ttgagg                                       26

<210> SEQ ID NO 13
<211> LENGTH: 28
<212> TYPE: DNA
<213> ORGANISM: Artificial Sequence
<220> FEATURE:
<223> OTHER INFORMATION: reverse primer

<400> SEQUENCE: 13
actcgagtca cagtgggcgg ttgtacag                                     28

<210> SEQ ID NO 14
<211> LENGTH: 27
<212> TYPE: DNA
<213> ORGANISM: Artificial Sequence
<220> FEATURE:
```

<223> OTHER INFORMATION: forward primer

<400> SEQUENCE: 14
aagatctctg tgaggctgca gacgctg                                27

<210> SEQ ID NO 15
<211> LENGTH: 28
<212> TYPE: DNA
<213> ORGANISM: Artificial Sequence
<220> FEATURE:
<223> OTHER INFORMATION: reverse primer

<400> SEQUENCE: 15
acccgggtta ttggtcgcca ccgtttcc                               28

<210> SEQ ID NO 16
<211> LENGTH: 26
<212> TYPE: DNA
<213> ORGANISM: Artificial Sequence
<220> FEATURE:
<223> OTHER INFORMATION: forward primer

<400> SEQUENCE: 16
ggttcgattg gggttggtgt aatata                                 26

<210> SEQ ID NO 17
<211> LENGTH: 26
<212> TYPE: DNA
<213> ORGANISM: Artificial Sequence
<220> FEATURE:
<223> OTHER INFORMATION: reverse primer

<400> SEQUENCE: 17
aaataatgta cgggkgagat gcatga                                 26

<210> SEQ ID NO 18
<211> LENGTH:
<212> TYPE:
<213> ORGANISM:

<400> SEQUENCE: 18

000

<210> SEQ ID NO 19
<211> LENGTH:
<212> TYPE:
<213> ORGANISM:

<400> SEQUENCE: 19

000

<210> SEQ ID NO 20
<211> LENGTH: 1656
<212> TYPE: DNA
<213> ORGANISM: Trypanosoma cruzi

<400> SEQUENCE: 20
atgcggaaga aagccgcagc attagcagcg cccacagcag acacacggcc gacgtgccgc     60
ggggctgcca ttgccaataa atttatggaa cgtgccggcc cccgtgaggg cgttgggaga    120
tcaacggaga tgccggctgc tggaccgacg gggtctcaaa gaactcaaac gcaacgggag    180
gtgaaagcgt cacaagacgc cgacgcgccg gccattagta gttatttcca gtccgaattg    240
gtgacatctc agtcgcacga gggtgtgtct cctctggcaa agactagggc caacgaacgg    300

```
cggaacgggg agcaggagcg ggagaaggaa ctgccggcgg ttggtggcgc cgttccaact    360
gggaagggga cggaccccaa acagcgagtg ctgcaggatt tgccagcgat gcacgcggag    420
ggacaaaacc agcacggtag agagggtgac aagggtgttt ccgtgaagat ggactcccct    480
ggtcgcgtac aggtgctgga gcaaatgttg ctacacctgg ctgcattgaa cagacagcta    540
gaattagaac ttatagaaac gcgacgggaa ctgacgatgt acaagcagct tttacctgat    600
gtgcagcgcc agaccgaggc ccatgctttg tctcaggagc atcacaaagc gaatagtgct    660
gctccgccac tgatgtcaga tgagaggcga cgacagatgc tctttacagg caacaacaa    720 caacagcaac aagtggaaga tctgcatggc ggtattagcg ggtgggaaac ggcagcgagg    780
agaatgcgct atggttacga ggaggggag agggacgccc tttcagatgg tgagggccgt    840
ccacgttgcg caggtcgtat gggctccccg aagagattcc tttcaacaca accgcctcga    900
agcagcagga accatcggaa ccctcacgct gctaacggga caaatggcaa tagtcatgtt    960
ccccattcgt ccagacaaaa aagtcacccg acaagaggag ctgctgtaac ttccgtaccg    1020
ttggcggcgt ccgcaaccaa tcgccgaggt cgttccatgc gacaacatac ccgaccccgc    1080
ggaccttctt atcttttcga acgcctcgac gctgaggatg caattgatat gctggagacg    1140
ctgaagcgct ctctcatgta tcgctgcaac cactcgcatc atcgatcaac agaaggagat    1200
gttgtgcggc cgccgcgaaa gccccggaaa ggcacgcggt ctgttccacc accaccgcca    1260
ccaccgccca tgtcatcatc gtcacaaaga aagcttgccg ccgcagttgc tggagcgccg    1320
gcatgcagcg tctcagcacg acacggaagg aaccatggcg tttctgcggt gggagatccg    1380
tcaaggggca atcgagtttc agaaacagct cgcatagctc atgctccttc ttttgggggg    1440
aagaaatgcg cgccgggcct aacccaactc catttctctt ccccttccag aagggctacg    1500
ccgatgaaaa aagacacgcc attgtcacgt ggtcaagcgg ctggagtagc agcagtagcg    1560
gtgggcggtg acgggcagct agaggcactg cagaggcgtt actgggaaca gtcccgtgcg    1620
atattggagc agcttgaaaa catgctggca gctgat                             1656
```

<210> SEQ ID NO 21
<211> LENGTH: 39
<212> TYPE: DNA
<213> ORGANISM: Artificial Sequence
<220> FEATURE:
<223> OTHER INFORMATION: pTAT linker

<400> SEQUENCE: 21
tccaccatgg ccggtaccgg tctcgaggtg catgcggtg                              39

<210> SEQ ID NO 22
<211> LENGTH: 14
<212> TYPE: PRT
<213> ORGANISM: Artificial Sequence
<220> FEATURE:
<223> OTHER INFORMATION: pTAT linker

<400> SEQUENCE: 22

Gly Ser Thr Met Ala Gly Thr Gly Leu Glu Val His Ala Val
1               5                   10

<210> SEQ ID NO 23
<211> LENGTH: 41
<212> TYPE: DNA
<213> ORGANISM: Artificial Sequence
<220> FEATURE:
<223> OTHER INFORMATION: pTAT-HA linker

```
<400> SEQUENCE: 23
ccatgtccgg ctatccatat gacgtcccag actatgctgg c                41

<210> SEQ ID NO 24
<211> LENGTH: 13
<212> TYPE: PRT
<213> ORGANISM: Artificial Sequence
<220> FEATURE:
<223> OTHER INFORMATION: pTAT-HA linker

<400> SEQUENCE: 24

Met Ser Gly Tyr Pro Tyr Asp Val Pro Asp Tyr Ala Gly
1               5                   10
```